US007135311B1

(12) United States Patent
David et al.

(10) Patent No.: US 7,135,311 B1
(45) Date of Patent: Nov. 14, 2006

(54) MEANS FOR DETECTING AND TREATING PATHOLOGIES LINKED TO FGFR3

(75) Inventors: Cappellen David, Merville-Franceville (FR); Chopin Dominique, Créteil (FR); Radvanyi Francois, Fontenay-aux-Roses (FR); Ricol David, Paris (FR); Thiery Jean-Paul, Paris (FR)

(73) Assignees: Institut Curie, Paris Cedex (FR); Centre National de la Recherche Scientifique (CNRS), Paris Cedex (FR)

( * ) Notice: Subject to any disclaimer, the term of this patent is extended or adjusted under 35 U.S.C. 154(b) by 0 days.

(21) Appl. No.: 09/959,747

(22) PCT Filed: May 4, 2000

(86) PCT No.: PCT/EP00/04591

§ 371 (c)(1),
(2), (4) Date: Jan. 16, 2002

(87) PCT Pub. No.: WO00/68424

PCT Pub. Date: Nov. 16, 2000

Related U.S. Application Data

(60) Provisional application No. 60/132,705, filed on May 5, 1999.

(51) Int. Cl.
*C12P 19/34* (2006.01)
*G01N 33/53* (2006.01)
(52) U.S. Cl. .................. 435/91.2; 435/7.23; 435/6; 436/518; 436/501

(58) Field of Classification Search .................. 435/6, 435/7.23
See application file for complete search history.

(56) References Cited

OTHER PUBLICATIONS

Karoui et al., (2001, Oncogene, vol. 20, pp. 5059-5061).*
Chesi, M et al; "Frequent Translocation t(4;14)(p16.3;q32.3) in Multiple Myeloma is Associated with Increased Exxpression and Activating Mutations of Fibroblast Growth Factor Receptor 3"; Nature Genetics, vol. 15, No. 3; 1997; pp. 260-264; XP001030990.
Webster, M. K. et al; "Enhanced Signaling and Morphological Transformation by a Membrane-Localized Derivative of the Fibroblast Growth Factor Receptor 3 Kinase Domain"; Mol. Cell Biol.; vol. 17, No. 10; 1997; pp. 5739-5747; XP002181674.
Li, Z.H. et al; "An Activating Mutation of the Myeloma Associated Ontogene Fibroblast Growth Factor Receptor 3 (FGFR3) has Hematopoietic Transforming Potential in Mice"; Blood; vol. 92, No. 10; Suppl. 1 (Part 1 of 2); Nov. 15, 1998; p. 383A; XP001030987.
Plowright, E.E. et al; "An Activating Mutation of the Myeloma Associated Oncogene Fibroblast Growth Factor Receptor 3 (FGFR3) Promotes Interleukin-6 (IL-6) Independence and Upregulation of bcl-xL"; Blood; vol. 92, No. 10, Suppl 1 (Part 1 of 2); Nov. 15, 1998; p. 383A; XP002181675.
Cappellen, D. et al; "Frequent Activating Mutations of FGFR3 in Human Bladder and Cervix Carcinomas" Nature Genetics; vol. 23; Sep. 1999; pp. 18-20; XP002181676.

* cited by examiner

*Primary Examiner*—Misook Yu
(74) *Attorney, Agent, or Firm*—Nixon & Vanderhye P.C.

(57) ABSTRACT

The invention relates to a method for detecting carcinomas in a biological sample, comprising identifying FGFR3 mutations.

17 Claims, 22 Drawing Sheets

Figure 2A

Figure 1:
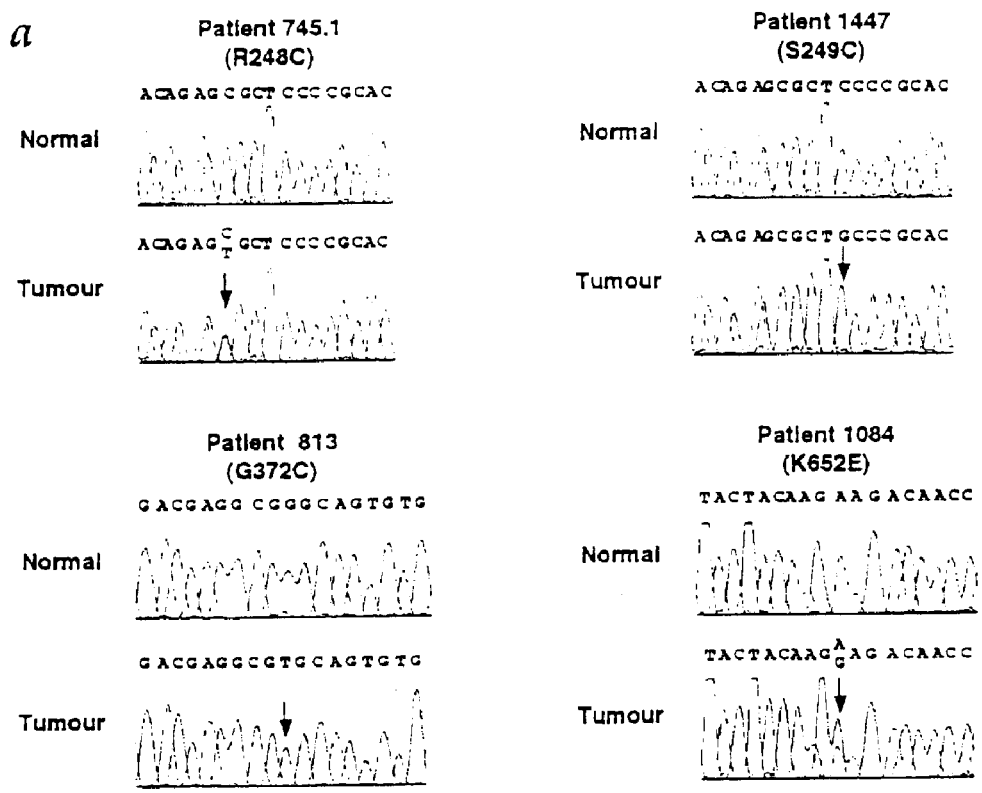
Figure 1:
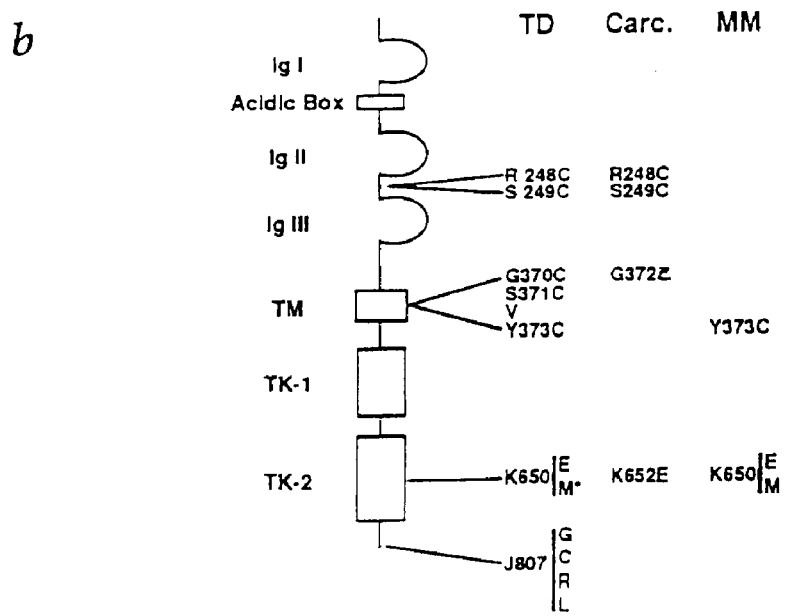

Wild Type FGFR3-IIIb:

```
ATGGGCGCCCCTGCCTGCGCCCTCGCGCTCTGCGTGGCCGTGGCCATCGTGGCCGGCGCCTCCTCGGAGTCCTTGGGGAC
GGAGCAGCGCGTCGTGGGGCGAGCGGCAGAAGTCCCGGGCCCAGAGCCCGGCCAGCAGGAGCAGTTGGTCTTCGGCAGCG
GGGATGCTGTGGAGCTGAGCTGTCCCCCGCCCGGGGGTGGTCCCATGGGCCCACTGTCTGGGTCAAGGATGGCACAGGG
CTGGTGCCCTCGGAGCGTGTCCTGGTGGGGCCCCAGCGGCTGCAGGTGCTGAATGCCTCCCACGAGGACTCCGGGGCCTA
CAGCTGCCGGCAGCGGCTCACGCAGCGCGTACTGTGCCACTTCAGTGTGCGGGTGACAGACGCTCCATCCTCGGGAGATG
ACGAAGACGGGGAGGACGAGGCTGAGGACACAGGTGTGGACACAGGGGCCCCTTACTGGACACGGCCCGAGCGGATGGAC
AAGAAGCTGCTGGCCGTGCCGGCCGCCAACACCGTCCGCTTCCGCTGCCCAGCCGCTGGCAACCCCACTCCCTCCATCTC
CTGGCTGAAGAACGGCAGGGAGTTCCGCGGCGAGCACCGCATTGGAGGCATCAAGCTGCGGCATCAGCAGTGGAGCCTGG
TCATGGAAAGCGTGGTGCCCTCGGACCGCGGCAACTACACCTGCGTCGTGGAGAACAAGTTTGGCAGCATCCGGCAGACG
TACACGCTGGACGTGCTGGAGCGCTCCCCGCACCGGCCCATCCTGCAGGCGGGGCTGCCGGCCAACCAGACGGCGGTGCT
GGGCAGCGACGTGGAGTTCCACTGCAAGGTGTACAGTGACGCACAGCCCCACATCCAGTGGCTCAAGCACGTGGAGGTGA
ACGGCAGCAAGGTGGGCCCGGACGGCACACCCTACGTTACCGTGCTCAAGTCCTGGATCAGTGAGAGTGTGGAGGCCGAC
GTGCGCCTCCGCCTGGCCAATGTGTCGGAGCGGGACGGGGGCGAGTACCTCTGTCGAGCCACCAATTTCATAGGCGTGGC
CGAGAAGGCCTTTTGGCTGAGCGTTCACGGGCCCCGAGCAGCCGAGGAGGAGCTGGTGGAGGCTGACGAGGCGGGCAGTG
TGTATGCAGGCATCCTCAGCTACGGGGTGGGCTTCTTCCTGTTCATCCTGGTGGTGGCGGCTGTGACGCTCTGCCGCCTG
CGCAGCCCCCCCAAGAAAGGCCTGGGCTCCCCCACCGTGCACAAGATCTCCCGCTTCCCGCTCAAGCGACAGGTGTCCCT
GGAGTCCAACGCGTCCATGAGCTCCAACACACCACTGGTGCGCATCGCAAGGCTGTCCTCAGGGGAGGGCCCCACGCTGG
CCAATGTCTCCGAGCTCGAGCTGCCTGCCGACCCCAAATGGGAGCTGTCTCGGGCCCGGCTGACCCTGGGCAAGCCCCTT
GGGGAGGGCTGCTTCGGCCAGGTGGTCATGGCGGAGGCCATCGGCATTGACAAGGACCGGGCCGCCAAGCCTGTCACCGT
AGCCGTGAAGATGCTGAAAGACGATGCCACTGACAAGGACCTGTCGGACCTGGTGTCTGAGATGGAGATGATGAAGATGA
TCGGGAAACACAAAAACATCATCAACCTGCTGGGCGCCTGCACGCAGGGCGGGCCCCTGTACGTGCTGGTGGAGTACGCG
GCCAAGGGTAACCTGCGGGAGTTTCTGCGGGCGCGGCGGCCCCCGGGCCTGGACTACTCCTTCGACACCTGCAAGCCGCC
CGAGGAGCAGCTCACCTTCAAGGACCTGGTGTCCTGTGCCTACCAGGTGGCCCGGGGCATGGAGTACTTGGCCTCCCAGA
AGTGCATCCACAGGGACCTGGCTGCCCGCAATGTGCTGGTGACCGAGGACAACGTGATGAAGATCGCAGACTTCGGGCTG
GCCCGGGACGTGCACAACCTCGACTACTACAAGAAGACAACCAACGGCCGGCTGCCCGTGAAGTGGATGGCGCCTGAGGC
CTTGTTTGACCGAGTCTACACTCACCAGAGTGACGTCTGGTCCTTTGGGGTCCTGCTCTGGGAGATCTTCACGCTGGGGG
GCTCCCCGTACCCCGGCATCCCTGTGGAGGAGCTCTTCAAGCTGCTGAAGGAGGGCCACCGCATGGACAAGCCCGCCAAC
TGCACACACGACCTGTACATGATCATGCGGGAGTGCTGGCATGCCGCGCCCTCCCAGAGGCCCACCTTCAAGCAGCTGGT
GGAGGACCTGGACCGTGTCCTTACCGTGACGTCCACCGACGAGTACCTGGACCTGTCGGCGCCTTTCGAGCAGTACTCCC
CGGGTGGCCAGGACACCCCCAGCTCCAGCTCCTCAGGGGACGACTCCGTGTTTGCCCACGACCTGCTGCCCCCGGCCCCA
CCCAGCAGTGGGGCTCGCGGACGTGA
```

Figure 2B

Mutant R248C FGFR3-IIIb:

ATGGGCGCCCCTGCCTGCGCCCTCGCGCTCTGCGTGGCCGTGGCCATCGTGGCCGGCGCCTCCTCGGAGTCCTTGGGGAC
GGAGCAGCGCGTCGTGGGGCGAGCGGCAGAAGTCCCGGGCCCAGAGCCCGGCCAGCAGGAGCAGTTGGTCTTCGGCAGCG
GGGATGCTGTGGAGCTGAGCTGTCCCCCGCCCGGGGGTGGTCCCATGGGGCCCACTGTCTGGGTCAAGGATGGCACAGGG
CTGGTGCCCTCGGAGCGTGTCCTGGTGGGGCCCCAGCGGCTGCAGGTGCTGAATGCCTCCCACGAGGACTCCGGGGCCTA
CAGCTGCCGGCAGCGGCTCACGCAGCGCGTACTGTGCCACTTCAGTGTGCGGGTGACAGACGCTCCATCCTCGGGAGATG
ACGAAGACGGGGAGGACGAGGCTGAGGACACAGGTGTGGACACAGGGGCCCCTTACTGGACACGGCCCGAGCGGATGGAC
AAGAAGCTGCTGGCCGTGCCGGCCGCCAACACCGTCCGCTTCCGCTGCCCAGCCGCTGGCAACCCCACTCCCTCCATCTC
CTGGCTGAAGAACGGCAGGGAGTTCCGCGGCGAGCACCGCATTGGAGGCATCAAGCTGCGGCATCAGCAGTGGAGCCTGG
TCATGGAAAGCGTGGTGCCCTCGGACCGCGGCAACTACACCTGCGTCGTGGAGAACAAGTTTGGCAGCATCCGGCAGACG
TACACGCTGGACGTGCTGGAGTGCTCCCCGCACCGGCCCATCCTGCAGGCGGGGCTGCCGGCCAACCAGACGGCGGTGCT
GGGCAGCGACGTGGAGTTCCACTGCAAGGTGTACAGTGACGCACAGCCCCACATCCAGTGGCTCAAGCACGTGGAGGTGA
ACGGCAGCAAGGTGGGCCCGGACGGCACACCCTACGTTACCGTGCTCAAGTCCTGGATCAGTGAGAGTGTGGAGGCCGAC
GTGCGCCTCCGCCTGGCCAATGTGTCGGAGCGGGACGGGGGCGAGTACCTCTGTCGAGCCACCAATTTCATAGGCGTGGC
CGAGAAGGCCTTTTGGCTGAGCGTTCACGGGCCCCGAGCAGCCGAGGAGGAGCTGGTGGAGGCTGACGAGGCGGGCAGTG
TGTATGCAGGCATCCTCAGCTACGGGGTGGGCTTCTTCCTGTTCATCCTGGTGGTGGCGGCTGTGACGCTCTGCCGCCTG
CGCAGCCCCCCCAAGAAAGGCCTGGGCTCCCCCACCGTGCACAAGATCTCCCGCTTCCCGCTCAAGCGACAGGTGTCCCT
GGAGTCCAACGCGTCCATGAGCTCCAACACACCACTGGTGCGCATCGCAAGGCTGTCCTCAGGGGAGGGCCCCACGCTGG
CCAATGTCTCCGAGCTCGAGCTGCCTGCCGACCCCAAATGGGAGCTGTCTCGGGCCCGGCTGACCCTGGGCAAGCCCCTT
GGGGAGGGCTGCTTCGGCCAGGTGGTCATGGCGGAGGCCATCGGCATTGACAAGGACCGGGCCGCCAAGCCTGTCACCGT
AGCCGTGAAGATGCTGAAAGACGATGCCACTGACAAGGACCTGTCGGACCTGGTGTCTGAGATGGAGATGATGAAGATGA
TCGGGAAACACAAAAACATCATCAACCTGCTGGGCGCCTGCACGCAGGGCGGGCCCCTGTACGTGCTGGTGGAGTACGCG
GCCAAGGGTAACCTGCGGGAGTTTCTGCGGGCGCGGCGGCCCCCGGGCCTGGACTACTCCTTCGACACCTGCAAGCCGCC
CGAGGAGCAGCTCACCTTCAAGGACCTGGTGTCCTGTGCCTACCAGGTGGCCCGGGGCATGGAGTACTTGGCCTCCCAGA
AGTGCATCCACAGGGACCTGGCTGCCCGCAATGTGCTGGTGACCGAGGACAACGTGATGAAGATCGCAGACTTCGGGCTG
GCCCGGGACGTGCACAACCTCGACTACTACAAGAAGACAACCAACGGCCGGCTGCCCGTGAAGTGGATGGCGCCTGAGGC
CTTGTTTGACCGAGTCTACACTCACCAGAGTGACGTCTGGTCCTTTGGGGTCCTGCTCTGGGAGATCTTCACGCTGGGGG
GCTCCCCGTACCCCGGCATCCCTGTGGAGGAGCTCTTCAAGCTGCTGAAGGAGGGCCACCGCATGGACAAGCCCGCCAAC
TGCACACACGACCTGTACATGATCATGCGGGAGTGCTGGCATGCCGCGCCCTCCCAGAGGCCCACCTTCAAGCAGCTGGT
GGAGGACCTGGACCGTGTCCTTACCGTGACGTCCACCGACGAGTACCTGGACCTGTCGGCGCCTTTCGAGCAGTACTCCC
CGGGTGGCCAGGACACCCCCAGCTCCAGCTCCTCAGGGGACGACTCCGTGTTTGCCCACGACCTGCTGCCCCCGGCCCCA
CCCAGCAGTGGGGGCTCGCGGACGTGA

Figure 2C

Mutant S249C FGFR3-IIIb:

```
ATGGGCGCCCCTGCCTGCGCCCTCGCGCTCTGCGTGGCCGTGGCCATCGTGGCCGGCGCCTCCTCGGAGTCCTTGGGGAC
GGAGCAGCGCGTCGTGGGGCGAGCGGCAGAAGTCCCGGGCCCAGAGCCCGGCCAGCAGGAGCAGTTGGTCTTCGGCAGCG
GGGATGCTGTGGAGCTGAGCTGTCCCCCGCCCGGGGGTGGTCCCATGGGGCCCACTGTCTGGGTCAAGGATGGCACAGGG
CTGGTGCCCTCGGAGCGTGTCCTGGTGGGGCCCCAGCGGCTGCAGGTGCTGAATGCCTCCCACGAGGACTCCGGGGCCTA
CAGCTGCCGGCAGCGGCTCACGCAGCGCGTACTGTGCCACTTCAGTGTGCGGGTGACAGACGCTCCATCCTCGGGAGATG
ACGAAGACGGGGAGGACGAGGCTGAGGACACAGGTGTGGACACAGGGGCCCCTTACTGGACACGGCCCGAGCGGATGGAC
AAGAAGCTGCTGGCCGTGCCGGCCGCCAACACCGTCCGCTTCCGCTGCCCAGCCGCTGGCAACCCCACTCCCTCCATCTC
CTGGCTGAAGAACGGCAGGGAGTTCCGCGGCGAGCACCGCATTGGAGGCATCAAGCTGCGGCATCAGCAGTGGAGCCTGG
TCATGGAAAGCGTGGTGCCCTCGGACCGCGGCAACTACACCTGCGTCGTGGAGAACAAGTTTGGCAGCATCCGGCAGACG
TACACGCTGGACGTGCTGGAGCGCTGCCCGCACCGGCCCATCCTGCAGGCGGGGCTGCCGGCCAACCAGACGGCGGTGCT
GGGCAGCGACGTGGAGTTCCACTGCAAGGTGTACAGTGACGCACAGCCCCACATCCAGTGGCTCAAGCACGTGGAGGTGA
ACGGCAGCAAGGTGGGCCCGGACGGCACACCCTACGTTACCGTGCTCAAGTCCTGGATCAGTGAGAGTGTGGAGGCCGAC
GTGCGCCTCCGCCTGGCCAATGTGTCGGAGCGGGACGGGGGCGAGTACCTCTGTCGAGCCACCAATTTCATAGGCGTGGC
CGAGAAGGCCTTTTGGCTGAGCGTTCACGGGCCCCGAGCAGCCGAGGAGGAGCTGGTGGAGGCTGACGAGGCGGGCAGTG
TGTATGCAGGCATCCTCAGCTACGGGGTGGGCTTCTTCCTGTTCATCCTGGTGGTGGCGGCTGTGACGCTCTGCCGCCTG
CGCAGCCCCCCCAAGAAAGGCCTGGGCTCCCCCACCGTGCACAAGATCTCCCGCTTCCCGCTCAAGCGACAGGTGTCCCT
GGAGTCCAACGCGTCCATGAGCTCCAACACACCACTGGTGCGCATCGCAAGGCTGTCCTCAGGGGAGGGCCCCACGCTGG
CCAATGTCTCCGAGCTCGAGCTGCCTGCCGACCCCAAATGGGAGCTGTCTCGGGCCCGGCTGACCCTGGGCAAGCCCCTT
GGGGAGGGCTGCTTCGGCCAGGTGGTCATGGCGGAGGCCATCGGCATTGACAAGGACCGGGCCGCCAAGCCTGTCACCGT
AGCCGTGAAGATGCTGAAAGACGATGCCACTGACAAGGACCTGTCGGACCTGGTGTCTGAGATGGAGATGATGAAGATGA
TCGGGAAACACAAAAACATCATCAACCTGCTGGGCGCCTGCACGCAGGGCGGGCCCCTGTACGTGCTGGTGGAGTACGCG
GCCAAGGGTAACCTGCGGGAGTTTCTGCGGGCGCGGCGGCCCCGGGCCTGGACTACTCCTTCGACACCTGCAAGCCGCC
CGAGGAGCAGCTCACCTTCAAGGACCTGGTGTCCTGTGCCTACCAGGTGGCCCGGGGCATGGAGTACTTGGCCTCCCAGA
AGTGCATCCACAGGGACCTGGCTGCCCGCAATGTGCTGGTGACCGAGGACAACGTGATGAAGATCGCAGACTTCGGGCTG
GCCCGGGACGTGCACAACCTCGACTACTACAAGAAGACAACCAACGGCCGGCTGCCCGTGAAGTGGATGGCGCCTGAGGC
CTTGTTTGACCGAGTCTACACTCACCAGAGTGACGTCTGGTCCTTTGGGGTCCTGCTCTGGGAGATCTTCACGCTGGGGG
GCTCCCCGTACCCCGGCATCCCTGTGGAGGAGCTCTTCAAGCTGCTGAAGGAGGGCCACCGCATGGACAAGCCCGCCAAC
TGCACACACGACCTGTACATGATCATGCGGGAGTGCTGGCATGCCGCGCCCTCCCAGAGGCCCACCTTCAAGCAGCTGGT
GGAGGACCTGGACCGTGTCCTTACCGTGACGTCCACCGACGAGTACCTGGACCTGTCGGCGCCTTTCGAGCAGTACTCCC
CGGGTGGCCAGGACACCCCCAGCTCCAGCTCCTCAGGGGACGACTCCGTGTTTGCCCACGACCTGCTGCCCCGGCCCCA
CCCAGCAGTGGGGCTCGCGGACGTGA
```

Figure 2D

Mutant G372C FGFR3-IIIb:

ATGGGCGCCCCTGCCTGCGCCCTCGCGCTCTGCGTGGCCGTGGCCATCGTGGCCGGCGCCTCCTCGGAGTCCTTGGGGAC
GGAGCAGCGCGTCGTGGGGCGAGCGGCAGAAGTCCCGGGCCCAGAGCCCGGCCAGCAGGAGCAGTTGGTCTTCGGCAGCG
GGGATGCTGTGGAGCTGAGCTGTCCCCCGCCCGGGGGTGGTCCCATGGGGCCCACTGTCTGGGTCAAGGATGGCACAGGG
CTGGTGCCCTCGGAGCGTGTCCTGGTGGGGCCCCAGCGGCTGCAGGTGCTGAATGCCTCCCACGAGGACTCCGGGGCCTA
CAGCTGCCGGCAGCGGCTCACGCAGCGCGTACTGTGCCACTTCAGTGTGCGGGTGACAGACGCTCCATCCTCGGGAGATG
ACGAAGACGGGGAGGACGAGGCTGAGGACACAGGTGTGGACACAGGGGCCCCTTACTGGACACGGCCCGAGCGGATGGAC
AAGAAGCTGCTGGCCGTGCCGGCCGCCAACACCGTCCGCTTCCGCTGCCCAGCCGCTGGCAACCCCACTCCCTCCATCTC
CTGGCTGAAGAACGGCAGGGAGTTCCGCGGCGAGCACCGCATTGGAGGCATCAAGCTGCGGCATCAGCAGTGGAGCCTGG
TCATGGAAAGCGTGGTGCCCTCGGACCGCGGCAACTACACCTGCGTCGTGGAGAACAAGTTTGGCAGCATCCGGCAGACG
TACACGCTGGACGTGCTGGAGCGCTCCCCGCACCGGCCCATCCTGCAGGCGGGGCTGCCGGCCAACCAGACGGCGGTGCT
GGGCAGCGACGTGGAGTTCCACTGCAAGGTGTACAGTGACGCACAGCCCCACATCCAGTGGCTCAAGCACGTGGAGGTGA
ACGGCAGCAAGGTGGGCCCGACGGCACACCCTACGTTACCGTGCTCAAGTCCTGGATCAGTGAGAGTGTGGAGGCCGAC
GTGCGCCTCCGCCTGGCCAATGTGTCGGAGCGGGACGGGGGCGAGTACCTCTGTCGAGCCACCAATTTCATAGGCGTGGC
CGAGAAGGCCTTTTGGCTGAGCGTTCACGGGCCCGAGCAGCCGAGGAGGAGCTGGTGGAGGCTGACGAGGCGTGCAGTG
TGTATGCAGGCATCCTCAGCTACGGGGTGGGCTTCTTCCTGTTCATCCTGGTGGTGGCGGCTGTGACGCTCTGCCGCCTG
CGCAGCCCCCCCAAGAAAGGCCTGGGCTCCCCCACCGTGCACAAGATCTCCCGCTTCCCGCTCAAGCGACAGGTGTCCCT
GGAGTCCAACGCGTCCATGAGCTCCAACACACCACTGGTGCGCATCGCAAGGCTGTCCTCAGGGGAGGGCCCCACGCTGG
CCAATGTCTCCGAGCTCGAGCTGCCTGCCGACCCCAAATGGGAGCTGTCTCGGGCCCGGCTGACCCTGGGCAAGCCCCTT
GGGGAGGGCTGCTTCGGCCAGGTGGTCATGGCGGAGGCCATCGGCATTGACAAGGACCGGGCCGCCAAGCCTGTCACCGT
AGCCGTGAAGATGCTGAAAGACGATGCCACTGACAAGGACCTGTCGGACCTGGTGTCTGAGATGGAGATGATGAAGATGA
TCGGGAAACACAAAAACATCATCAACCTGCTGGGCGCCTGCACGCAGGGCGGGCCCCTGTACGTGCTGGTGGAGTACGCG
GCCAAGGGTAACCTGCGGGAGTTTCTGCGGGCGCGGCGGCCCCGGGCCTGGACTACTCCTTCGACACCTGCAAGCCGCC
CGAGGAGCAGCTCACCTTCAAGGACCTGGTGTCCTGTGCCTACCAGGTGGCCCGGGGCATGGAGTACTTGGCCTCCCAGA
AGTGCATCCACAGGGACCTGGCTGCCCGCAATGTGCTGGTGACCGAGGACAACGTGATGAAGATCGCAGACTTCGGGCTG
GCCCGGGACGTGCACAACCTCGACTACTACAAGAAGACAACCAACGGCCGGCTGCCCGTGAAGTGGATGGCGCCTGAGGC
CTTGTTTGACCGAGTCTACACTCACCAGAGTGACGTCTGGTCCTTTGGGGTCCTGCTCTGGGAGATCTTCACGCTGGGGG
GCTCCCCGTACCCCGGCATCCCTGTGGAGGAGCTCTTCAAGCTGCTGAAGGAGGGCCACCGCATGGACAAGCCCGCCAAC
TGCACACACGACCTGTACATGATCATGCGGGAGTGCTGGCATGCCGCGCCCTCCCAGAGGCCCACCTTCAAGCAGCTGGT
GGAGGACCTGGACCGTGTCCTTACCGTGACGTCCACCGACGAGTACCTGGACCTGTCGGCGCCTTTCGAGCAGTACTCCC
CGGGTGGCCAGGACACCCCCAGCTCCAGCTCCTCAGGGGACGACTCCGTGTTTGCCCACGACCTGCTGCCCCCGGCCCCA
CCCAGCAGTGGGGGCTCGCGGACGTGA

Figure 2E

Mutant K652E FGFR3-IIIb:

ATGGGCGCCCCTGCCTGCGCCCTCGCGCTCTGCGTGGCCGTGGCCATCGTGGCCGGCGCCTCCTCGGAGTCCTTGGGGAC
GGAGCAGCGCGTCGTGGGGCGAGCGGCAGAAGTCCCGGGCCCAGAGCCCGGCCAGCAGGAGCAGTTGGTCTTCGGCAGCG
GGGATGCTGTGGAGCTGAGCTGTCCCCCGCCCGGGGGTGGTCCCATGGGCCCACTGTCTGGGTCAAGGATGGCACAGGG
CTGGTGCCCTCGGAGCGTGTCCTGGTGGGGCCCCAGCGGCTGCAGGTGCTGAATGCCTCCCACGAGGACTCCGGGGCCTA
CAGCTGCCGGCAGCGGCTCACGCAGCGCGTACTGTGCCACTTCAGTGTGCGGGTGACAGACGCTCCATCCTCGGGAGATG
ACGAAGACGGGGAGGACGAGGCTGAGGACACAGGTGTGGACACAGGGGCCCCTTACTGGACACGGCCCGAGCGGATGGAC
AAGAAGCTGCTGGCCGTGCCGGCCGCCAACACCGTCCGCTTCCGCTGCCCAGCCGCTGGCAACCCCACTCCCTCCATCTC
CTGGCTGAAGAACGGCAGGGAGTTCCGCGGCGAGCACCGCATTGGAGGCATCAAGCTGCGGCATCAGCAGTGGAGCCTGG
TCATGGAAAGCGTGGTGCCCTCGGACCGCGGCAACTACACCTGCGTCGTGGAGAACAAGTTTGGCAGCATCCGGCAGACG
TACACGCTGGACGTGCTGGAGCGCTCCCCGCACCGGCCCATCCTGCAGGCGGGGCTGCCGGCCAACCAGACGGCGGTGCT
GGGCAGCGACGTGGAGTTCCACTGCAAGGTGTACAGTGACGCACAGCCCCACATCCAGTGGCTCAAGCACGTGGAGGTGA
ACGGCAGCAAGGTGGGCCCGGACGGCACACCCTACGTTACCGTGCTCAAGTCCTGGATCAGTGAGAGTGTGGAGGCCGAC
GTGCGCCTCCGCCTGGCCAATGTGTCGGAGCGGGACGGGGGCGAGTACCTCTGTCGAGCCACCAATTTCATAGGCGTGGC
CGAGAAGGCCTTTTGGCTGAGCGTTCACGGGCCCCGAGCAGCCGAGGAGGAGCTGGTGGAGGCTGACGAGGCGGGCAGTG
TGTATGCAGGCATCCTCAGCTACGGGGTGGGCTTCTTCCTGTTCATCCTGGTGGTGGCGGCTGTGACGCTCTGCCGCCTG
CGCAGCCCCCCCAAGAAAGGCCTGGGCTCCCCCACCGTGCACAAGATCTCCCGCTTCCCGCTCAAGCGACAGGTGTCCCT
GGAGTCCAACGCGTCCATGAGCTCCAACACACCACTGGTGCGCATCGCAAGGCTGTCCTCAGGGGAGGGCCCCACGCTGG
CCAATGTCTCCGAGCTCGAGCTGCCTGCCGACCCCAAATGGGAGCTGTCTCGGGCCCGGCTGACCCTGGGCAAGCCCCTT
GGGGAGGGCTGCTTCGGCCAGGTGGTCATGGCGGAGGCCATCGGCATTGACAAGGACCGGGCCGCCAAGCCTGTCACCGT
AGCCGTGAAGATGCTGAAAGACGATGCCACTGACAAGGACCTGTCGGACCTGGTGTCTGAGATGGAGATGATGAAGATGA
TCGGGAAACACAAAAACATCATCAACCTGCTGGGCGCCTGCACGCAGGGCGGGCCCCTGTACGTGCTGGTGGAGTACGCG
GCCAAGGGTAACCTGCGGGAGTTTCTGCGGGCGCGGCGGCCCCCGGGCCTGGACTACTCCTTCGACACCTGCAAGCCGCC
CGAGGAGCAGCTCACCTTCAAGGACCTGGTGTCCTGTGCCTACCAGGTGGCCCGGGGCATGGAGTACTTGGCCTCCCAGA
AGTGCATCCACAGGGACCTGGCTGCCCGCAATGTGCTGGTGACCGAGGACAACGTGATGAAGATCGCAGACTTCGGGCTG
GCCCGGGACGTGCACAACCTCGACTACTACAAGGAGACAACCAACGGCCGGCTGCCCGTGAAGTGGATGGCGCCTGAGGC
CTTGTTTGACCGAGTCTACACTCACCAGAGTGACGTCTGGTCCTTTGGGGTCCTGCTCTGGGAGATCTTCACGCTGGGGG
GCTCCCCGTACCCCGGCATCCCTGTGGAGGAGCTCTTCAAGCTGCTGAAGGAGGGCCACCGCATGGACAAGCCCGCCAAC
TGCACACACGACCTGTACATGATCATGCGGGAGTGCTGGCATGCCGCGCCCTCCCAGAGGCCCACCTTCAAGCAGCTGGT
GGAGGACCTGGACCGTGTCCTTACCGTGACGTCCACCGACGAGTACCTGGACCTGTCGGCGCCTTTCGAGCAGTACTCCC
CGGGTGGCCAGGACACCCCCAGCTCCAGCTCCTCAGGGGACGACTCCGTGTTTGCCCACGACCTGCTGCCCCCGGCCCCA
CCCAGCAGTGGGGGCTCGCGGACGTGA

Figure 2F

Mutant S373C FGFR3-IIIb:

```
ATGGGCGCCCCTGCCTGCGCCCTCGCGCTCTGCGTGGCCGTGGCCATCGTGGCCGGCGCCTCCTCGGAGTCCTTGGGGAC
GGAGCAGCGCGTCGTGGGGCGAGCGGCAGAAGTCCCGGGCCCAGAGCCCGGCCAGCAGGAGCAGTTGGTCTTCGGCAGCG
GGGATGCTGTGGAGCTGAGCTGTCCCCCGCCCGGGGGTGGTCCCATGGGCCCACTGTCTGGGTCAAGGATGGCACAGGG
CTGGTGCCCTCGGAGCGTGTCCTGGTGGGGCCCCAGCGGCTGCAGGTGCTGAATGCCTCCCACGAGGACTCCGGGGCCTA
CAGCTGCCGGCAGCGGCTCACGCAGCGCGTACTGTGCCACTTCAGTGTGCGGGTGACAGACGCTCCATCCTCGGGAGATG
ACGAAGACGGGGAGGACGAGGCTGAGGACACAGGTGTGGACACAGGGGCCCCTTACTGGACACGGCCCGAGCGGATGGAC
AAGAAGCTGCTGGCCGTGCCGGCCGCCAACACCGTCCGCTTCCGCTGCCCAGCCGCTGGCAACCCCACTCCCTCCATCTC
CTGGCTGAAGAACGGCAGGGAGTTCCGCGGCGAGCACCGCATTGGAGGCATCAAGCTGCGGCATCAGCAGTGGAGCCTGG
TCATGGAAAGCGTGGTGCCCTCGGACCGCGGCAACTACACCTGCGTCGTGGAGAACAAGTTTGGCAGCATCCGGCAGACG
TACACGCTGGACGTGCTGGAGCGCTCCCCGCACCGGCCCATCCTGCAGGCGGGGCTGCCGGCCAACCAGACGGCGGTGCT
GGGCAGCGACGTGGAGTTCCACTGCAAGGTGTACAGTGACGCACAGCCCCACATCCAGTGGCTCAAGCACGTGGAGGTGA
ACGGCAGCAAGGTGGGCCCGGACGGCACACCCTACGTTACCGTGCTCAAGTCCTGGATCAGTGAGAGTGTGGAGGCCGAC
GTGCGCCTCCGCCTGGCCAATGTGTCGGAGCGGGACGGGGGCGAGTACCTCTGTCGAGCCACCAATTTCATAGGCGTGGC
CGAGAAGGCCTTTTGGCTGAGCGTTCACGGGCCCCGAGCAGCCGAGGAGGAGCTGGTGGAGGCTGACGAGGCGGGCTGTG
TGTATGCAGGCATCCTCAGCTACGGGGTGGGCTTCTTCCTGTTCATCCTGGTGGTGGCGGCTGTGACGCTCTGCCGCCTG
CGCAGCCCCCCCAAGAAAGGCCTGGGCTCCCCCACCGTGCACAAGATCTCCCGCTTCCCGCTCAAGCGACAGGTGTCCCT
GGAGTCCAACGCGTCCATGAGCTCCAACACACCACTGGTGCGCATCGCAAGGCTGTCCTCAGGGGAGGGCCCCACGCTGG
CCAATGTCTCCGAGCTCGAGCTGCCTGCCGACCCCAAATGGGAGCTGTCTCGGGCCCGGCTGACCCTGGGCAAGCCCCTT
GGGGAGGGCTGCTTCGGCCAGGTGGTCATGGCGGAGGCCATCGGCATTGACAAGGACCGGGCCGCCAAGCCTGTCACCGT
AGCCGTGAAGATGCTGAAAGACGATGCCACTGACAAGGACCTGTCGGACCTGGTGTCTGAGATGGAGATGATGAAGATGA
TCGGGAAACACAAAAACATCATCAACCTGCTGGGCGCCTGCACGCAGGGCGGGCCCCTGTACGTGCTGGTGGAGTACGCG
GCCAAGGGTAACCTGCGGGAGTTTCTGCGGGCGCGGCGGCCCCGGGGCCTGGACTACTCCTTCGACACCTGCAAGCCGCC
CGAGGAGCAGCTCACCTTCAAGGACCTGGTGTCCTGTGCCTACCAGGTGGCCCGGGGCATGGAGTACTTGGCCTCCCAGA
AGTGCATCCACAGGGACCTGGCTGCCCGCAATGTGCTGGTGACCGAGGACAACGTGATGAAGATCGCAGACTTCGGGCTG
GCCCGGGACGTGCACAACCTCGACTACTACAAGAAGACAACCAACGGCCGGCTGCCCGTGAAGTGGATGGCGCCTGAGGC
CTTGTTTGACCGAGTCTACACTCACCAGAGTGACGTCTGGTCCTTTGGGGTCCTGCTCTGGGAGATCTTCACGCTGGGGG
GCTCCCCGTACCCCGGCATCCCTGTGGAGGAGCTCTTCAAGCTGCTGAAGGAGGGCCACCGCATGGACAAGCCCGCCAAC
TGCACACACGACCTGTACATGATCATGCGGGAGTGCTGGCATGCCGCGCCCTCCCAGAGGCCCACCTTCAAGCAGCTGGT
GGAGGACCTGGACCGTGTCCTTACCGTGACGTCCACCGACGAGTACCTGGACCTGTCGGCGCCTTTCGAGCAGTACTCCC
CGGGTGGCCAGGACACCCCCAGCTCCAGCTCCTCAGGGGACGACTCCGTGTTTGCCCACGACCTGCTGCCCCGGCCCCA
CCCAGCAGTGGGGCTCGCGGACGTGA
```

Figure 2G

Mutant Y375C FGFR3-IIIb:

```
ATGGGCGCCCCTGCCTGCGCCCTCGCGCTCTGCGTGGCCGTGGCCATCGTGGCCGGCGCCTCCTCGGAGTCCTTGGGGAC
GGAGCAGCGCGTCGTGGGGCGAGCGGCAGAAGTCCCGGGCCCAGAGCCCGGCCAGCAGGAGCAGTTGGTCTTCGGCAGCG
GGGATGCTGTGGAGCTGAGCTGTCCCCCGCCCGGGGGTGGTCCCATGGGGCCCACTGTCTGGGTCAAGGATGGCACAGGG
CTGGTGCCCTCGGAGCGTGTCCTGGTGGGGCCCCAGCGGCTGCAGGTGCTGAATGCCTCCCACGAGGACTCCGGGGCCTA
CAGCTGCCGGCAGCGGCTCACGCAGCGCGTACTGTGCCACTTCAGTGTGCGGGTGACAGACGCTCCATCCTCGGGAGATG
ACGAAGACGGGGAGGACGAGGCTGAGGACACAGGTGTGGACACAGGGGCCCCTTACTGGACACGGCCCGAGCGGATGGAC
AAGAAGCTGCTGGCCGTGCCGGCCGCCAACACCGTCCGCTTCCGCTGCCCAGCCGCTGGCAACCCCACTCCCTCCATCTC
CTGGCTGAAGAACGGCAGGGAGTTCCGCGGCGAGCACCGCATTGGAGGCATCAAGCTGCGGCATCAGCAGTGGAGCCTGG
TCATGGAAAGCGTGGTGCCCTCGGACCGCGGCAACTACACCTGCGTCGTGGAGAACAAGTTTGGCAGCATCCGGCAGACG
TACACGCTGGACGTGCTGGAGCGCTCCCCGCACCGGCCCATCCTGCAGGCGGGGCTGCCGGCCAACCAGACGGCGGTGCT
GGGCAGCGACGTGGAGTTCCACTGCAAGGTGTACAGTGACGCACAGCCCCACATCCAGTGGCTCAAGCACGTGGAGGTGA
ACGGCAGCAAGGTGGGCCCGGACGGCACACCCTACGTTACCGTGCTCAAGTCCTGGATCAGTGAGAGTGTGGAGGCCGAC
GTGCGCCTCCGCCTGGCCAATGTGTCGGAGCGGGACGGGGGCGAGTACCTCTGTCGAGCCACCAATTTCATAGGCGTGGC
CGAGAAGGCCTTTTGGCTGAGCGTTCACGGGCCCGAGCAGCCGAGGAGGAGCTGGTGGAGGCTGACGAGGCGGGCAGTG
TGTGTGCAGGCATCCTCAGCTACGGGGTGGGCTTCTTCCTGTTCATCCTGGTGGTGGCGGCTGTGACGCTCTGCCGCCTG
CGCAGCCCCCCAAGAAAGGCCTGGGCTCCCCACCGTGCACAAGATCTCCCGCTTCCCGCTCAAGCGACAGGTGTCCCT
GGAGTCCAACGCGTCCATGAGCTCCAACACACCACTGGTGCGCATCGCAAGGCTGTCCTCAGGGGAGGGCCCCACGCTGG
CCAATGTCTCCGAGCTCGAGCTGCCTGCCGACCCCAAATGGGAGCTGTCTCGGGCCCGGCTGACCCTGGGCAAGCCCCTT
GGGGAGGGCTGCTTCGGCCAGGTGGTCATGGCGGAGGCCATCGGCATTGACAAGGACCGGGCCGCCAAGCCTGTCACCGT
AGCCGTGAAGATGCTGAAAGACGATGCCACTGACAAGGACCTGTCGGACCTGGTGTCTGAGATGGAGATGATGAAGATGA
TCGGGAAACACAAAAACATCATCAACCTGCTGGGCGCCTGCACGCAGGGCGGGCCCCTGTACGTGCTGGTGGAGTACGCG
GCCAAGGGTAACCTGCGGGAGTTTCTGCGGGCGCGGCGGCCCCGGGCCTGGACTACTCCTTCGACACCTGCAAGCCGCC
CGAGGAGCAGCTCACCTTCAAGGACCTGGTGTCCTGTGCCTACCAGGTGGCCCGGGGCATGGAGTACTTGGCCTCCCAGA
AGTGCATCCACAGGGACCTGGCTGCCCGCAATGTGCTGGTGACCGAGGACAACGTGATGAAGATCGCAGACTTCGGGCTG
GCCCGGGACGTGCACAACCTCGACTACTACAAGAAGACAACCAACGGCCGGCTGCCCGTGAAGTGGATGGCGCCTGAGGC
CTTGTTTGACCGAGTCTACACTCACCAGAGTGACGTCTGGTCCTTTGGGGTCCTGCTCTGGGAGATCTTCACGCTGGGGG
GCTCCCCGTACCCCGGCATCCCTGTGGAGGAGCTCTTCAAGCTGCTGAAGGAGGGCCACCGCATGGACAAGCCCGCCAAC
TGCACACACGACCTGTACATGATCATGCGGGAGTGCTGGCATGCCGCGCCCTCCCAGAGGCCCACCTTCAAGCAGCTGGT
GGAGGACCTGGACCGTGTCCTTACCGTGACGTCCACCGACGAGTACCTGGACCTGTCGGCGCCTTTCGAGCAGTACTCCC
CGGGTGGCCAGGACACCCCCAGCTCCAGCTCCTCAGGGGACGACTCCGTGTTTCCCACGACCTGCTGCCCCCGGCCCCA
CCCAGCAGTGGGGCTCGCGGACGTGA
``` figure 2H

Mutant K652M FGFR3-IIIb:

ATGGGCGCCCCTGCCTGCGCCCTCGCGCTCTGCGTGGCCGTGGCCATCGTGGCCGGCGCCTCCTCGGAGTCCTTGGGGAC
GGAGCAGCGCGTCGTGGGGCGAGCGGCAGAAGTCCCGGGCCCAGAGCCGGCCAGCAGGAGCAGTTGGTCTTCGGCAGCG
GGGATGCTGTGGAGCTGAGCTGTCCCCCGCCCGGGGGTGGTCCCATGGGGCCCACTGTCTGGGTCAAGGATGGCACAGGG
CTGGTGCCCTCGGAGCGTGTCCTGGTGGGGCCCCAGCGGCTGCAGGTGCTGAATGCCTCCCACGAGGACTCCGGGGCCTA
CAGCTGCCGGCAGCGGCTCACGCAGCGCGTACTGTGCCACTTCAGTGTGCGGGTGACAGACGCTCCATCCTCGGGAGATG
ACGAAGACGGGGAGGACGAGGCTGAGGACACAGGTGTGGACACAGGGGCCCCTTACTGGACACGGCCCGAGCGGATGGAC
AAGAAGCTGCTGGCCGTGCCGGCCGCCAACACCGTCCGCTTCCGCTGCCCAGCCGCTGGCAACCCCACTCCCTCCATCTC
CTGGCTGAAGAACGGCAGGGAGTTCCGCGGCGAGCACCGCATTGGAGGCATCAAGCTGCGGCATCAGCAGTGGAGCCTGG
TCATGGAAAGCGTGGTGCCCTCGGACCGCGGCAACTACACCTGCGTCGTGGAGAACAAGTTTGGCAGCATCCGGCAGACG
TACACGCTGGACGTGCTGGAGCGCTCCCCGCACCGGCCCATCCTGCAGGCGGGGCTGCCGGCCAACCAGACGGCGGTGCT
GGGCAGCGACGTGGAGTTCCACTGCAAGGTGTACAGTGACGCACAGCCCCACATCCAGTGGCTCAAGCACGTGGAGGTGA
ACGGCAGCAAGGTGGGCCCGGACGGCACACCCTACGTTACCGTGCTCAAGTCCTGGATCAGTGAGAGTGTGGAGGCCGAC
GTGCGCCTCCGCCTGGCCAATGTGTCGGAGCGGGACGGGGGCGAGTACCTCTGTCGAGCCACCAATTTCATAGGCGTGGC
CGAGAAGGCCTTTTGGCTGAGCGTTCACGGGCCCCGAGCAGCCGAGGAGGAGCTGGTGGAGGCTGACGAGGCGGGCAGTG
TGTATGCAGGCATCCTCAGCTACGGGGTGGGCTTCTTCCTGTTCATCCTGGTGGTGGCGGCTGTGACGCTCTGCCGCCTG
CGCAGCCCCCCCAAGAAAGGCCTGGGCTCCCCCACCGTGCACAAGATCTCCCGCTTCCCGCTCAAGCGACAGGTGTCCCT
GGAGTCCAACGCGTCCATGAGCTCCAACACACCACTGGTGCGCATCGCAAGGCTGTCCTCAGGGGAGGGCCCCACGCTGG
CCAATGTCTCCGAGCTCGAGCTGCCTGCCGACCCCAAATGGGAGCTGTCTCGGGCCCGGCTGACCCTGGGCAAGCCCCTT
GGGGAGGGCTGCTTCGGCCAGGTGGTCATGGCGGAGGCCATCGGCATTGACAAGGACCGGGCCGCCAAGCCTGTCACCGT
AGCCGTGAAGATGCTGAAAGACGATGCCACTGACAAGGACCTGTCGGACCTGGTGTCTGAGATGGAGATGATGAAGATGA
TCGGGAAACACAAAAACATCATCAACCTGCTGGGCGCCTGCACGCAGGGCGGGCCCCTGTACGTGCTGGTGGAGTACGCG
GCCAAGGGTAACCTGCGGGAGTTTCTGCGGGCGCGGCGGCCCCCGGGCCTGGACTACTCCTTCGACACCTGCAAGCCGCC
CGAGGAGCAGCTCACCTTCAAGGACCTGGTGTCCTGTGCCTACCAGGTGGCCCGGGGCATGGAGTACTTGGCCTCCCAGA
AGTGCATCCACAGGGACCTGGCTGCCCGCAATGTGCTGGTGACCGAGGACAACGTGATGAAGATCGCAGACTTCGGGCTG
GCCCGGGACGTGCACAACCTCGACTACTACAAGATGACAACCAACGGCCGGCTGCCCGTGAAGTGGATGGCGCCTGAGGC
CTTGTTTGACCGAGTCTACACTCACCAGAGTGACGTCTGGTCCTTTGGGGTCCTGCTCTGGGAGATCTTCACGCTGGGGG
GCTCCCCGTACCCCGGCATCCCTGTGGAGGAGCTCTTCAAGCTGCTGAAGGAGGGCCACCGCATGGACAAGCCCGCCAAC
TGCACACACGACCTGTACATGATCATGCGGGAGTGCTGGCATGCCGCGCCCTCCCAGAGGCCCACCTTCAAGCAGCTGGT
GGAGGACCTGGACCGTGTCCTTACCGTGACGTCCACCGACGAGTACCTGGACCTGTCGGCGCCTTTCGAGCAGTACTCCC
CGGGTGGCCAGGACACCCCCAGCTCCAGCTCCTCAGGGGACGACTCCGTGTTTGCCCACGACCTGCTGCCCCCGGCCCCA
CCCAGCAGTGGGGGCTCGCGGACGTGA

Figure 2I

Mutant X809C FGFR3-IIIb:

```
ATGGGCGCCCCTGCCTGCGCCCTCGCGCTCTGCGTGGCCGTGGCCATCGTGGCCGGCGCCTCCTCGGAGTCCTTGGGGAC
GGAGCAGCGCGTCGTGGGGCGAGCGGCAGAAGTCCCGGGCCCAGAGCCCGGCCAGCAGGAGCAGTTGGTCTTCGGCAGCG
GGGATGCTGTGGAGCTGAGCTGTCCCCCGCCCGGGGGTGGTCCCATGGGCCCCACTGTCTGGGTCAAGGATGGCACAGGG
CTGGTGCCCTCGGAGCGTGTCCTGGTGGGGCCCAGCGGCTGCAGGTGCTGAATGCCTCCCACGAGGACTCCGGGGCCTA
CAGCTGCCGGCAGCGGCTCACGCAGCGCGTACTGTGCCACTTCAGTGTGCGGGTGACAGACGCTCCATCCTCGGGAGATG
ACGAAGACGGGGAGGACGAGGCTGAGGACACAGGTGTGGACACAGGGGCCCCTTACTGGACACGGCCCGAGCGGATGGAC
AAGAAGCTGCTGGCCGTGCCGGCCGCCAACACCGTCCGCTTCCGCTGCCCAGCCGCTGGCAACCCCACTCCCTCCATCTC
CTGGCTGAAGAACGGCAGGGAGTTCCGCGGCGAGCACCGCATTGGAGGCATCAAGCTGCGGCATCAGCAGTGGAGCCTGG
TCATGGAAAGCGTGGTGCCCTCGGACCGCGGCAACTACACCTGCGTCGTGGAGAACAAGTTTGGCAGCATCCGGCAGACG
TACACGCTGGACGTGCTGGAGCGCTCCCCGCACCGGCCCATCCTGCAGGCGGGGCTGCCGGCCAACCAGACGGCGGTGCT
GGGCAGCGACGTGGAGTTCCACTGCAAGGTGTACAGTGACGCACAGCCCCACATCCAGTGGCTCAAGCACGTGGAGGTGA
ACGGCAGCAAGGTGGGCCCGGACGGCACACCCTACGTTACCGTGCTCAAGTCCTGGATCAGTGAGAGTGTGGAGGCCGAC
GTGCGCCTCCGCCTGGCCAATGTGTCGGAGCGGGACGGGGGCGAGTACCTCTGTCGAGCCACCAATTTCATAGGCGTGGC
CGAGAAGGCCTTTTGGCTGAGCGTTCACGGGCCCGAGCAGCCGAGGAGGAGCTGGTGGAGGCTGACGAGGCGGGCAGTG
TGTATGCAGGCATCCTCAGCTACGGGGTGGGCTTCTTCCTGTTCATCCTGGTGGTGGCCGGCTGTGACGCTCTGCCGCCTG
CGCAGCCCCCCAAGAAAGGCCTGGGCTCCCCACCGTGCACAAGATCTCCCGCTTCCCGCTCAAGCGACAGGTGTCCCT
GGAGTCCAACGCGTCCATGAGCTCCAACACACCACTGGTGCGCATCGCAAGGCTGTCCTCAGGGGAGGGCCCCACGCTGG
CCAATGTCTCCGAGCTCGAGCTGCCTGCCGACCCCAAATGGGAGCTGTCTCGGGCCCGGCTGACCCTGGGCAAGCCCCTT
GGGGAGGGCTGCTTCGGCCAGGTGGTCATGGCGGAGGCCATCGGCATTGACAAGGACCGGGCCGCCAAGCCTGTCACCGT
AGCCGTGAAGATGCTGAAAGACGATGCCACTGACAAGGACCTGTCGGACCTGGTGTCTGAGATGGAGATGATGAAGATGA
TCGGGAAACACAAAAACATCATCAACCTGCTGGGCGCCTGCACGCAGGGCGGGCCCCTGTACGTGCTGGTGGAGTACGCG
GCCAAGGGTAACCTGCGGGAGTTTCTGCGGGCGCGGCGGCCCCGGGCCTGGACTACTCCTTCGACACCTGCAAGCCGCC
CGAGGAGCAGCTCACCTTCAAGGACCTGGTGTCCTGTGCCTACCAGGTGGCCCGGGGCATGGAGTACTTGGCCTCCCAGA
AGTGCATCCACAGGGACCTGGCTGCCCGCAATGTGCTGGTGACCGAGGACAACGTGATGAAGATCGCAGACTTCGGGCTG
GCCCGGGACGTGCACAACCTCGACTACTACAAGAAGACAACCAACGGCCGGCTGCCCGTGAAGTGGATGGCGCCTGAGGC
CTTGTTTGACCGAGTCTACACTCACCAGAGTGACGTCTGGTCCTTTGGGGTCCTGCTCTGGGAGATCTTCACGCTGGGGG
GCTCCCCGTACCCCGGCATCCCTGTGGAGGAGCTCTTCAAGCTGCTGAAGGAGGGCCACCGCATGGACAAGCCCGCCAAC
TGCACACACGACCTGTACATGATCATGCGGGAGTGCTGGCATGCCGCGCCCTCCCAGAGGCCCACCTTCAAGCAGCTGGT
GGAGGACCTGGACCGTGTCCTTACCGTGACGTCCACCGACGAGTACCTGGACCTGTCGGCGCCTTTCGAGCAGTACTCCC
CGGGTGGCCAGGACACCCCCAGCTCCAGCTCCTCAGGGGACGACTCCGTGTTTGCCCACGACCTGCTGCCCCCGGCCCCA
CCCAGCAGTGGGGCTCGCGGACGTGC
```

Figure 2J   Mutant 1

Mutant X809G FGFR3-IIIb:

```
ATGGGCGCCCCTGCCTGCGCCCTCGCGCTCTGCGTGGCCGTGGCCATCGTGGCCGGCGCCTCCTCGGAGTCCTTGGGGAC
GGAGCAGCGCGTCGTGGGGCGAGCGGCAGAAGTCCCGGGCCCAGAGCCCGGCCAGCAGGAGCAGTTGGTCTTCGGCAGCG
GGGATGCTGTGGAGCTGAGCTGTCCCCCGCCCGGGGGTGGTCCCATGGGGCCCACTGTCTGGGTCAAGGATGGCACAGGG
CTGGTGCCCTCGGAGCGTGTCCTGGTGGGGCCCCAGCGGCTGCAGGTGCTGAATGCCTCCCACGAGGACTCCGGGGCCTA
CAGCTGCCGGCAGCGGCTCACGCAGCGCGTACTGTGCCACTTCAGTGTGCGGGTGACAGACGCTCCATCCTCGGGAGATG
ACGAAGACGGGGAGGACGAGGCTGAGGACACAGGTGTGGACACAGGGGCCCCTTACTGGACACGGCCCGAGCGGATGGAC
AAGAAGCTGCTGGCCGTGCCGGCCGCCAACACCGTCCGCTTCCGCTGCCCAGCCGCTGGCAACCCCACTCCCTCCATCTC
CTGGCTGAAGAACGGCAGGGAGTTCCGCGGCGAGCACCGCATTGGAGGCATCAAGCTGCGGCATCAGCAGTGGAGCCTGG
TCATGGAAAGCGTGGTGCCCTCGGACCGCGGCAACTACACCTGCGTCGTGGAGAACAAGTTTGGCAGCATCCGGCAGACG
TACACGCTGGACGTGCTGGAGCGCTCCCCGCACCGGCCCATCCTGCAGGCGGGGCTGCCGGCCAACCAGACGGCGGTGCT
GGGCAGCGACGTGGAGTTCCACTGCAAGGTGTACAGTGACGCACAGCCCCACATCCAGTGGCTCAAGCACGTGGAGGTGA
ACGGCAGCAAGGTGGGCCCGGACGGCACACCCTACGTTACCGTGCTCAAGTCCTGGATCAGTGAGAGTGTGGAGGCCGAC
GTGCGCCTCCGCCTGGCCAATGTGTCGGAGCGGGACGGGGGCGAGTACCTCTGTCGAGCCACCAATTTCATAGGCGTGGC
CGAGAAGGCCTTTTGGCTGAGCGTTCACGGGCCCCGAGCAGCCGAGGAGGAGCTGGTGGAGGCTGACGAGGCGGGCAGTG
TGTATGCAGGCATCCTCAGCTACGGGGTGGGCTTCTTCCTGTTCATCCTGGTGGTGGCGGCTGTGACGCTCTGCCGCCTG
CGCAGCCCCCCAAGAAAGGCCTGGGCTCCCCCACCGTGCACAAGATCTCCCGCTTCCCGCTCAAGCGACAGGTGTCCCT
GGAGTCCAACGCGTCCATGAGCTCCAACACACCACTGGTGCGCATCGCAAGGCTGTCCTCAGGGGAGGGCCCCACGCTGG
CCAATGTCTCCGAGCTCGAGCTGCCTGCCGACCCCAAATGGGAGCTGTCTCGGGCCCGGCTGACCCTGGGCAAGCCCCTT
GGGGAGGGCTGCTTCGGCCAGGTGGTCATGGCGGAGGCCATCGGCATTGACAAGGACCGGGCCGCCAAGCCTGTCACCGT
AGCCGTGAAGATGCTGAAAGACGATGCCACTGACAAGGACCTGTCGGACCTGGTGTCTGAGATGGAGATGATGAAGATGA
TCGGGAAACACAAAAACATCATCAACCTGCTGGGCGCCTGCACGCAGGGCGGGCCCCTGTACGTGCTGGTGGAGTACGCG
GCCAAGGGTAACCTGCGGGAGTTTCTGCGGGCGCGGCGCCCCGGGCCTGGACTACTCCTTCGACACCTGCAAGCCGCC
CGAGGAGCAGCTCACCTTCAAGGACCTGGTGTCCTGTGCCTACCAGGTGGCCCGGGGCATGGAGTACTTGGCCTCCCAGA
AGTGCATCCACAGGGACCTGGCTGCCCGCAATGTGCTGGTGACCGAGGACAACGTGATGAAGATCGCAGACTTGGGGCTG
GCCCGGGACGTGCACAACCTCGACTACTACAAGAAGACAACCAACGGCCGGCTGCCCGTGAAGTGGATGGCGCCTGAGGC
CTTGTTTGACCGAGTCTACACTCACCAGAGTGACGTCTGGTCCTTTGGGGTCCTGCTCTGGGAGATCTTCACGCTGGGGG
GCTCCCCGTACCCCGGCATCCCTGTGGAGGAGCTCTTCAAGCTGCTGAAGGAGGGCCACCGCATGGACAAGCCCGCCAAC
TGCACACACGACCTGTACATGATCATGCGGGAGTGCTGGCATGCGCGCCCTCCCAGAGGCCCACCTTCAAGCAGCTGGT
GGAGGACCTGGACCGTGTCCTTACCGTGACGTCCACCGACGAGTACCTGGACCTGTCGGCGCCTTTCGAGCAGTACTCCC
CGGGTGGCCAGGACACCCCCAGCTCCAGCTCCTCAGGGGACGACTCCGTGTTTGCCCACGACCTGCTGCCCCCGGCCCCA
CCCAGCAGTGGGGGCTCGCGGACGGGA
```

Figure 2K  Mutant 2

Mutant X809G FGFR3-IIIb:

```
ATGGGCGCCCCTGCCTGCGCCCTCGCGCTCTGCGTGGCCGTGGCCATCGTGGCCGGCGCCTCCTCGGAGTCCTTGGGGAC
GGAGCAGCGCGTCGTGGGGCGAGCGGCAGAAGTCCCGGGCCCAGAGCCCGGCCAGCAGGAGCAGTTGGTCTTCGGCAGCG
GGGATGCTGTGGAGCTGAGCTGTCCCCCGCCCGGGGGTGGTCCCATGGGGCCCACTGTCTGGGTCAAGGATGGCACAGGG
CTGGTGCCCTCGGAGCGTGTCCTGGTGGGGCCCCAGCGGCTGCAGGTGCTGAATGCCTCCCACGAGGACTCCGGGGCCTA
CAGCTGCCGGCAGCGGCTCACGCAGCGCGTACTGTGCCACTTCAGTGTGCGGGTGACAGACGCTCCATCCTCGGGAGATG
ACGAAGACGGGGAGGACGAGGCTGAGGACACAGGTGTGGACACAGGGGCCCCTTACTGGACACGGCCCGAGCGGATGGAC
AAGAAGCTGCTGGCCGTGCCGGCCGCCAACACCGTCCGCTTCCGCTGCCCAGCCGCTGGCAACCCCACTCCCTCCATCTC
CTGGCTGAAGAACGGCAGGGAGTTCCGCGGCGAGCACCGCATTGGAGGCATCAAGCTGCGGCATCAGCAGTGGAGCCTGG
TCATGGAAAGCGTGGTGCCCTCGGACCGCGGCAACTACACCTGCGTCGTGGAGAACAAGTTTGGCAGCATCCGGCAGACG
TACACGCTGGACGTGCTGGAGCGCTCCCCGCACCGGCCCATCCTGCAGGCGGGGCTGCCGGCCAACCAGACGGCGGTGCT
GGGCAGCGACGTGGAGTTCCACTGCAAGGTGTACAGTGACGCACAGCCCCACATCCAGTGGCTCAAGCACGTGGAGGTGA
ACGGCAGCAAGGTGGGCCCGGACGGCACACCCTACGTTACCGTGCTCAAGTCCTGGATCAGTGAGAGTGTGGAGGCCGAC
GTGCGCCTCCGCCTGGCCAATGTGTCGGAGCGGGACGGGGCGAGTACCTCTGTCGAGCCACCAATTTCATAGGCGTGGC
CGAGAAGGCCTTTTGGCTGAGCGTTCACGGGCCCCGAGCAGCCGAGGAGGAGCTGGTGGAGGCTGACGAGGCGGGCAGTG
TGTATGCAGGCATCCTCAGCTACGGGGTGGGCTTCTTCCTGTTCATCCTGGTGGTGGCGGCTGTGACGCTCTGCCGCCTG
CGCAGCCCCCCCAAGAAAGGCCTGGGCTCCCCCACCGTGCACAAGATCTCCCGCTTCCCGCTCAAGCGACAGGTGTCCCT
GGAGTCCAACGCGTCCATGAGCTCCAACACACCACTGGTGCGCATCGCAAGGCTGTCCTCAGGGGAGGGCCCCACGCTGG
CCAATGTCTCCGAGCTCGAGCTGCCTGCCGACCCCAAATGGGAGCTGTCTCGGGCCCGGCTGACCCTGGGCAAGCCCCTT
GGGGAGGGCTGCTTCGGCCAGGTGGTCATGGCGGAGGCCATCGGCATTGACAAGGACCGGGCCGCCAAGCCTGTCACCGT
AGCCGTGAAGATGCTGAAAGACGATGCCACTGACAAGGACCTGTCGGACCTGGTGTCTGAGATGGAGATGATGAAGATGA
TCGGGAAACACAAAAACATCATCAACCTGCTGGGCGCCTGCACGCAGGGCGGGCCCCTGTACGTGCTGGTGGAGTACGCG
GCCAAGGGTAACCTGCGGGAGTTTCTGCGGGCGCGGCGGCCCCGGGCCTGGACTACTCCTTCGACACCTGCAAGCCGCC
CGAGGAGCAGCTCACCTTCAAGGACCTGGTGTCCTGTGCCTACCAGGTGGCCCGGGGCATGGAGTACTTGGCCTCCCAGA
AGTGCATCCACAGGGACCTGGCTGCCCGCAATGTGCTGGTGACCGAGGACAACGTGATGAAGATCGCAGACTTCGGGCTG
GCCCGGGACGTGCACAACCTCGACTACTACAAGAAGACAACCAACGGCCGGCTGCCCGTGAAGTGGATGGCGCCTGAGGC
CTTGTTTGACCGAGTCTACACTCACCAGAGTGACGTCTGGTCCTTTGGGGTCCTGCTCTGGGAGATCTTCACGCTGGGGG
GCTCCCCGTACCCCGGCATCCCTGTGGAGGAGCTCTTCAAGCTGCTGAAGGAGGGCCACCGCATGGACAAGCCCGCCAAC
TGCACACACGACCTGTACATGATCATGCGGGAGTGCTGGCATGCCGCGCCCTCCCAGAGGCCCACCTTCAAGCAGCTGGT
GGAGGACCTGGACCGTGTCCTTACCGTGACGTCCACCGACGAGTACCTGGACCTGTCGGCGCCTTTCGAGCAGTACTCCC
CGGGTGGCCAGGACACCCCCAGCTCCAGCTCCTCAGGGGACGACTCCGTGTTTGCCCACGACCTGCTGCCCCCGGCCCCA
CCCAGCAGTGGGGGCTCGCGGACGAGA
```

Figure 2L    Mutant 3

Mutant X809G FGFR3-IIIb:

```
ATGGGCGCCCCTGCCTGCGCCCTCGCGCTCTGCGTGGCCGTGGCCATCGTGGCCGGCGCCTCCTCGGAGTCCTTGGGGAC
GGAGCAGCGCGTCGTGGGGCGAGCGGCAGAAGTCCCGGGCCCAGAGCCCGGCCAGCAGGAGCAGTTGGTCTTCGGCAGCG
GGGATGCTGTGGAGCTGAGCTGTCCCCCGCCCGGGGGTGGTCCCATGGGGCCCACTGTCTGGGTCAAGGATGGCACAGGG
CTGGTGCCCTCGGAGCGTGTCCTGGTGGGGCCCCAGCGGCTGCAGGTGCTGAATGCCTCCCACGAGGACTCCGGGGCCTA
CAGCTGCCGGCAGCGGCTCACGCAGCGCGTACTGTGCCACTTCAGTGTGCGGGTGACAGACGCTCCATCCTCGGGAGATG
ACGAAGACGGGGAGGACGAGGCTGAGGACACAGGTGTGGACACAGGGGCCCCTTACTGGACACGGCCCGAGCGGATGGAC
AAGAAGCTGCTGGCCGTGCCGGCCGCCAACACCGTCCGCTTCCGCTGCCCAGCCGCTGGCAACCCCACTCCCTCCATCTC
CTGGCTGAAGAACGGCAGGGAGTTCCGCGGCGAGCACCGCATTGGAGGCATCAAGCTGCGGCATCAGCAGTGGAGCCTGG
TCATGGAAAGCGTGGTGCCCTCGGACCGCGGCAACTACACCTGCGTCGTGGAGAACAAGTTTGGCAGCATCCGGCAGACG
TACACGCTGGACGTGCTGGAGCGCTCCCCGCACCGGCCCATCCTGCAGGCGGGGCTGCCGGCCAACCAGACGGCGGTGCT
GGGCAGCGACGTGGAGTTCCACTGCAAGGTGTACAGTGACGCACAGCCCCACATCCAGTGGCTCAAGCACGTGGAGGTGA
ACGGCAGCAAGGTGGGCCCGGACGGCACACCCTACGTTACCGTGCTCAAGTCCTGGATCAGTGAGAGTGTGGAGGCCGAC
GTGCGCCTCCGCCTGGCCAATGTGTCGGAGCGGGACGGGGGCGAGTACCTCTGTCGAGCCACCAATTTCATAGGCGTGGC
CGAGAAGGCCTTTTGGCTGAGCGTTCACGGGCCCCGAGCAGCCGAGGAGGAGCTGGTGGAGGCTGACGAGGCGGGCAGTG
TGTATGCAGGCATCCTCAGCTACGGGGTGGGCTTCTTCCTGTTCATCCTGGTGGTGGCGGCTGTGACGCTCTGCCGCCTG
CGCAGCCCCCCCAAGAAAGGCCTGGGCTCCCCCACCGTGCACAAGATCTCCCGCTTCCCGCTCAAGCGACAGGTGTCCCT
GGAGTCCAACGCGTCCATGAGCTCCAACACACCACTGGTGCGCATCGCAAGGCTGTCCTCAGGGGAGGGCCCCACGCTGG
CCAATGTCTCCGAGCTCGAGCTGCCTGCCGACCCCAAATGGGAGCTGTCTCGGGCCCGGCTGACCCTGGGCAAGCCCCTT
GGGGAGGGCTGCTTCGGCCAGGTGGTCATGGCGGAGGCCATCGGCATTGACAAGGACCGGGCCGCCAAGCCTGTCACCGT
AGCCGTGAAGATGCTGAAAGACGATGCCACTGACAAGGACCTGTCGGACCTGGTGTCTGAGATGGAGATGATGAAGATGA
TCGGGAAACACAAAAACATCATCAACCTGCTGGGCGCCTGCACGCAGGGCGGGCCCCTGTACGTGCTGGTGGAGTACGCG
GCCAAGGGTAACCTGCGGGAGTTTCTGCGGGCGCGGCGGCCCCCGGGCCTGGACTACTCCTTCGACACCTGCAAGCCGCC
CGAGGAGCAGCTCACCTTCAAGGACCTGGTGTCCTGTGCCTACCAGGTGGCCCGGGGCATGGAGTACTTGGCCTCCCAGA
AGTGCATCCACAGGGACCTGGCTGCCCGCAATGTGCTGGTGACCGAGGACAACGTGATGAAGATCGCAGACTTCGGGCTG
GCCCGGGACGTGCACAACCTCGACTACTACAAGAAGACAACCAACGGCCGGCTGCCCGTGAAGTGGATGGCGCCTGAGGC
CTTGTTTGACCGAGTCTACACTCACCAGAGTGACGTCTGGTCCTTTGGGGTCCTGCTCTGGGAGATCTTCACGCTGGGGG
GCTCCCCGTACCCCGGCATCCCTGTGGAGGAGCTCTTCAAGCTGCTGAAGGAGGGCCACCGCATGGACAAGCCCGCCAAC
TGCACACACGACCTGTACATGATCATGCGGGAGTGCTGGCATGCCGCGCCCTCCCAGAGGCCCACCTTCAAGCAGCTGGT
GGAGGACCTGGACCGTGTCCTTACCGTGACGTCCACCGACGAGTACCTGGACCTGTCGGCGCCTTTCGAGCAGTACTCCC
CGGGTGGCCAGGACACCCCAGCTCCAGCTCCTCAGGGGACGACTCCGTGTTTGCCCACGACCTGCTGCCCCGGCCCCA
CCCAGCAGTGGGGGCTCGCGGACGCGA
```

Figure 2M

Mutant X809L FGFR3-IIIb:

```
ATGGGCGCCCCTGCCTGCGCCCTCGCGCTCTGCGTGGCCGTGGCCATCGTGGCCGGCGCCTCCTCGGAGTCCTTGGGGAC
GGAGCAGCGCGTCGTGGGGCGAGCGGCAGAAGTCCCGGGCCCAGAGCCCGGCCAGCAGGAGCAGTTGGTCTTCGGCAGCG
GGGATGCTGTGGAGCTGAGCTGTCCCCCGCCCGGGGGTGGTCCCATGGGGCCCACTGTCTGGGTCAAGGATGGCACAGGG
CTGGTGCCCTCGGAGCGTGTCCTGGTGGGGCCCCAGCGGCTGCAGGTGCTGAATGCCTCCCACGAGGACTCCGGGGCCTA
CAGCTGCCGGCAGCGGCTCACGCAGCGCGTACTGTGCCACTTCAGTGTGCGGGTGACAGACGCTCCATCCTCGGGAGATG
ACGAAGACGGGGAGGACGAGGCTGAGGACACAGGTGTGGACACAGGGGCCCCTTACTGGACACGGCCCGAGCGGATGGAC
AAGAAGCTGCTGGCCGTGCCGGCCGCCAACACCGTCCGCTTCCGCTGCCCAGCCGCTGGCAACCCCACTCCCTCCATCTC
CTGGCTGAAGAACGGCAGGGAGTTCCGCGGCGAGCACCGCATTGGAGGCATCAAGCTGCGGCATCAGCAGTGGAGCCTGG
TCATGGAAAGCGTGGTGCCCTCGGACCGCGGCAACTACACCTGCGTCGTGGAGAACAAGTTTGGCAGCATCCGGCAGACG
TACACGCTGGACGTGCTGGAGCGCTCCCCGCACCGGCCCATCCTGCAGGCGGGGCTGCCGGCCAACCAGACGGCGGTGCT
GGGCAGCGACGTGGAGTTCCACTGCAAGGTGTACAGTGACGCACAGCCCCACATCCAGTGGCTCAAGCACGTGGAGGTGA
ACGGCAGCAAGGTGGGCCCGGACGGCACACCCTACGTTACCGTGCTCAAGTCCTGGATCAGTGAGAGTGTGGAGGCCGAC
GTGCGCCTCCGCCTGGCCAATGTGTCGGAGCGGGACGGGGGCGAGTACCTCTGTCGAGCCACCAATTTCATAGGCGTGGC
CGAGAAGGCCTTTTGGCTGAGCGTTCACGGGCCCGAGCAGCCGAGGAGGAGCTGGTGGAGGCTGACGAGGCGGGCAGTG
TGTATGCAGGCATCCTCAGCTACGGGGTGGGCTTCTTCCTGTTCATCCTGGTGGTGGCGGCTGTGACGCTCTGCCGCCTG
CGCAGCCCCCCCAAGAAAGGCCTGGGCTCCCCCACCGTGCACAAGATCTCCCGCTTCCCGCTCAAGCGACAGGTGTCCCT
GGAGTCCAACGCGTCCATGAGCTCCAACACACCACTGGTGCGCATCGCAAGGCTGTCCTCAGGGGAGGGCCCCACGCTGG
CCAATGTCTCCGAGCTCGAGCTGCCTGCCGACCCCAAATGGGAGCTGTCTCGGGCCCGGCTGACCCTGGGCAAGCCCCTT
GGGGAGGGCTGCTTCGGCCAGGTGGTCATGGCGGAGGCCATCGGCATTGACAAGGACCGGGCCGCCAAGCCTGTCACCGT
AGCCGTGAAGATGCTGAAAGACGATGCCACTGACAAGGACCTGTCGGACCTGGTGTCTGAGATGGAGATGATGAAGATGA
TCGGGAAACACAAAAACATCATCAACCTGCTGGGCGCCTGCACGCAGGGCGGGCCCTGTACGTGCTGGTGGAGTACGCG
GCCAAGGGTAACCTGCGGGAGTTTCTGCGGGCGCGGCGGCCCCGGGCCTGGACTACTCCTTCGACACCTGCAAGCCGCC
CGAGGAGCAGCTCACCTTCAAGGACCTGGTGTCCTGTGCCTACCAGGTGGCCCGGGGCATGGAGTACTTGGCCTCCCAGA
AGTGCATCCACAGGGACCTGGCTGCCCGCAATGTGCTGGTGACCGAGGACAACGTGATGAAGATCGCAGACTTCGGCTG
GCCCGGGACGTGCACAACCTCGACTACTACAAGAAGACAACCAACGGCCGGCTGCCCGTGAAGTGGATGGCGCCTGAGGC
CTTGTTTGACCGAGTCTACACTCACCAGAGTGACGTCTGGTCCTTTGGGGTCCTGCTCTGGGAGATCTTCACGCTGGGGG
GCTCCCCGTACCCCGGCATCCCTGTGGAGGAGCTCTTCAAGCTGCTGAAGGAGGGCCACCGCATGGACAAGCCCGCCAAC
TGCACACACGACCTGTACATGATCATGCGGGAGTGCTGGCATGCCGCGCCCTCCCAGAGGCCCACCTTCAAGCAGCTGGT
GGAGGACCTGGACCGTGTCCTTACCGTGACGTCCACCGACGAGTACCTGGACCTGTCGGCGCCTTTCGAGCAGTACTCCC
CGGGTGGCCAGGACACCCCCAGCTCCAGCTCCTCAGGGGACGACTCCGTGTTTGCCCACGACCTGCTGCCCCGGCCCCA
CCCAGCAGTGGGGGCTCGCGGACGTTA
```

Figure 2N  Mutant 1

Mutant N542K FGFR3-IIIb:

```
ATGGGCGCCCCTGCCTGCGCCCTCGCGCTCTGCGTGGCCGTGGCCATCGTGGCCGGCGCCTCCTCGGAGTCCTTGGGGAC
GGAGCAGCGCGTCGTGGGGCGAGCGGCAGAAGTCCCGGGCCCAGAGCCCGGCCAGCAGGAGCAGTTGGTCTTCGGCAGCG
GGGATGCTGTGGAGCTGAGCTGTCCCCCGCCCGGGGGTGGTCCCATGGGGCCCACTGTCTGGGTCAAGGATGGCACAGGG
CTGGTGCCCTCGGAGCGTGTCCTGGTGGGGCCCCAGCGGCTGCAGGTGCTGAATGCCTCCCACGAGGACTCCGGGGCCTA
CAGCTGCCGGCAGCGGCTCACGCAGCGCGTACTGTGCCACTTCAGTGTGCGGGTGACAGACGCTCCATCCTCGGGAGATG
ACGAAGACGGGGAGGACGAGGCTGAGGACACAGGTGTGGACACAGGGGCCCCTTACTGGACACGGCCCGAGCGGATGGAC
AAGAAGCTGCTGGCCGTGCCGGCCGCCAACACCGTCCGCTTCCGCTGCCCAGCCGCTGGCAACCCCACTCCCTCCATCTC
CTGGCTGAAGAACGGCAGGGAGTTCCGCGGCGAGCACCGCATTGGAGGCATCAAGCTGCGGCATCAGCAGTGGAGCCTGG
TCATGGAAAGCGTGGTGCCCTCGGACCGCGGCAACTACACCTGCGTCGTGGAGAACAAGTTTGGCAGCATCCGGCAGACG
TACACGCTGGACGTGCTGGAGCGCTCCCCGCACCGGCCCATCCTGCAGGCGGGGCTGCCGGCCAACCAGACGGCGGTGCT
GGGCAGCGACGTGGAGTTCCACTGCAAGGTGTACAGTGACGCACAGCCCCACATCCAGTGGCTCAAGCACGTGGAGGTGA
ACGGCAGCAAGGTGGGCCCGGACGGCACACCCTACGTTACCGTGCTCAAGTCCTGGATCAGTGAGAGTGTGGAGGCCGAC
GTGCGCCTCCGCCTGGCCAATGTGTCGGAGCGGGACGGGGGCGAGTACCTCTGTCGAGCCACCAATTTCATAGGCGTGGC
CGAGAAGGCCTTTTGGCTGAGCGTTCACGGGCCCGAGCAGCCGAGGAGGAGCTGGTGGAGGCTGACGAGGCGGGCAGTG
TGTATGCAGGCATCCTCAGCTACGGGGTGGGCTTCTTCCTGTTCATCCTGGTGGTGGCGGCTGTGACGCTCTGCCGCCTG
CGCAGCCCCCCCAAGAAAGGCCTGGGCTCCCCCACCGTGCACAAGATCTCCCGCTTCCCGCTCAAGCGACAGGTGTCCCT
GGAGTCCAACGCGTCCATGAGCTCCAACACACCACTGGTGCGCATCGCAAGGCTGTCCTCAGGGGAGGGCCCCACGCTGG
CCAATGTCTCCGAGCTCGAGCTGCCTGCCGACCCCAAATGGGAGCTGTCTCGGGCCCGGCTGACCCTGGGCAAGCCCCTT
GGGGAGGGCTGCTTCGGCCAGGTGGTCATGGCGGAGGCCATCGGCATTGACAAGGACCGGGCCGCCAAGCCTGTCACCGT
AGCCGTGAAGATGCTGAAAGACGATGCCACTGACAAGGACCTGTCGGACCTGGTGTCTGAGATGGAGATGATGAAGATGA
TCGGGAAACACAAAAACATCATCAAACTGCTGGGCGCCTGCACGCAGGGCGGGCCCCTGTACGTGCTGGTGGAGTACGCG
GCCAAGGGTAACCTGCGGGAGTTTCTGCGGGCGCGGCGGCCCCGGGCCTGGACTACTCCTTCGACACCTGCAAGCCGCC
CGAGGAGCAGCTCACCTTCAAGGACCTGGTGTCCTGTGCCTACCAGGTGGCCCGGGGCATGGAGTACTTGGCCTCCCAGA
AGTGCATCCACAGGGACCTGGCTGCCCGCAATGTGCTGGTGACCGAGGACAACGTGATGAAGATCGCAGACTTCGGGCTG
GCCCGGGACGTGCACAACCTCGACTACTACAAGAAGACAACCAACGGCCGGCTGCCCGTGAAGTGGATGGCGCCTGAGGC
CTTGTTTGACCGAGTCTACACTCACCAGAGTGACGTCTGGTCCTTTGGGGTCCTGCTCTGGGAGATCTTCACGCTGGGGG
GCTCCCCGTACCCCGGCATCCCTGTGGAGGAGCTCTTCAAGCTGCTGAAGGAGGGCCACCGCATGGACAAGCCCGCCAAC
TGCACACACGACCTGTACATGATCATGCGGGAGTGCTGGCATGCCGCGCCCTCCCAGAGGCCCACCTTCAAGCAGCTGGT
GGAGGACCTGGACCGTGTCCTTACCGTGACGTCCACCGACGAGTACCTGGACCTGTCGGCGCCTTTCGAGCAGTACTCCC
CGGGTGGCCAGGACACCCCCAGCTCCAGCTCCTCAGGGGACGACTCCGTGTTTGCCCACGACCTGCTGCCCCCGGCCCCA
CCCAGCAGTGGGGGCTCGCGGACGTGA
```

Figure 20  Mutant 2

Mutant N540K FGFR3-IIIb:

```
ATGGGCGCCCCTGCCTGCGCCCTCGCGCTCTGCGTGGCCGTGGCCATCGTGGCCGGCGCCTCCTCGGAGTCCTTGGGGAC
GGAGCAGCGCGTCGTGGGGCGAGCGGCAGAAGTCCCGGGCCCAGAGCCCGGCCAGCAGGAGCAGTTGGTCTTCGGCAGCG
GGGATGCTGTGGAGCTGAGCTGTCCCCCGCCCGGGGGTGGTCCCATGGGGCCCACTGTCTGGGTCAAGGATGGCACAGGG
CTGGTGCCCTCGGAGCGTGTCCTGGTGGGGCCCAGCGGCTGCAGGTGCTGAATGCCTCCCACGAGGACTCCGGGGCCTA
CAGCTGCCGGCAGCGGCTCACGCAGCGCGTACTGTGCCACTTCAGTGTGCGGGTGACAGACGGCTCCATCCTCGGGAGATG
ACGAAGACGGGGAGGACGAGGCTGAGGACACAGGTGTGGACACAGGGGCCCCTTACTGGACACGGCCCGAGCGGATGGAC
AAGAAGCTGCTGGCCGTGCCGGCCGCCAACACCGTCCGCTTCCGCTGCCCAGCCGCTGGCAACCCCACTCCCTCCATCTC
CTGGCTGAAGAACGGCAGGGAGTTCCGCGGCGAGCACCGCATTGGAGGCATCAAGCTGCGGCATCAGCAGTGGAGCCTGG
TCATGGAAAGCGTGGTGCCCTCGGACCGCGGCAACTACACCTGCGTCGTGGAGAACAAGTTTGGCAGCATCCGGCAGACG
TACACGCTGGACGTGCTGGAGCGCTCCCCGCACCGGCCCATCCTGCAGGCGGGGCTGCCGGCCAACCAGACGGCGGTGCT
GGGCAGCGACGTGGAGTTCCACTGCAAGGTGTACAGTGACGCACAGCCCCACATCCAGTGGCTCAAGCACGTGGAGGTGA
ACGGCAGCAAGGTGGGCCCGGACGGCACACCCTACGTTACCGTGCTCAAGTCCTGGATCAGTGAGAGTGTGGAGGCCGAC
GTGCGCCTCCGCCTGGCCAATGTGTCGGAGCGGGACGGGGGCGAGTACCTCTGTCGAGCCACCAATTTCATAGGCGTGGC
CGAGAAGGCCTTTTGGCTGAGCGTTCACGGGCCCCGAGCAGCCGAGGAGGAGCTGGTGGAGGCTGACGAGGCGGGCAGTG
TGTATGCAGGCATCCTCAGCTACGGGGTGGGCTTCTTCCTGTTCATCCTGGTGGTGGCCGGCTGTGACGCTCTGCCGCCTG
CGCAGCCCCCCAAGAAAGGCCTGGGCTCCCCCACCGTGCACAAGATCTCCCGCTTCCCGCTCAAGCGACAGGTGTCCCT
GGAGTCCAACGCGTCCATGAGCTCCAACACACCACTGGTGCGCATCGCAAGGCTGTCCTCAGGGGAGGGCCCCACGCTGG
CCAATGTCTCCGAGCTCGAGCTGCCTGCCGACCCCAAATGGGAGCTGTCTCGGGCCCGGCTGACCCTGGGCAAGCCCCTT
GGGGAGGGCTGCTTCGGCCAGGTGGTCATGGCGGAGCCCATCGGCATTGACAAGGACGGGCCGCCAAGCCTGTCACCGT
AGCCGTGAAGATGCTGAAAGACGATGCCACTGACAAGGACCTGTCGGACCTGGTGTCTGAGATGGAGATGATGAAGATGA
TCGGGAAACACAAAAACATCATCAAGCTGCTGGGCGCCTGCACGCAGGGCGGGCCCCTGTACGTGCTGGTGGAGTACGCG
GCCAAGGGTAACCTGCGGGAGTTTCTGCGGGCGCGGCGGCCCCGGGCCTGGACTACTCCTTCGACACCTGCAAGCCGCC
CGAGGAGCAGCTCACCTTCAAGGACCTGGTGTCCTGTGCCTACCAGGTGGCCCGGGGCATGGAGTACTTGGCCTCCCAGA
AGTGCATCCACAGGGACCTGGCTGCCCGCAATGTGCTGGTGACCGAGGACAACGTGATGAAGATCGCAGACTTCGGGCTG
GCCCGGGACGTGCACAACCTCGACTACTACAAGAAGACAACCAACGGCCGGCTGCCCGTGAAGTGGATGGCGCCTGAGGC
CTTGTTTGACCGAGTCTACACTCACCAGAGTGACGTCTGGTCCTTTGGGGTCCTGCTCTGGGAGATCTTCACGCTGGGGG
GCTCCCCGTACCCCGGCATCCCTGTGGAGGAGCTCTTCAAGCTGCTGAAGGAGGGCCACCGCATGGACAAGCCCGCCAAC
TGCACACACGACCTGTACATGATCATGCGGGAGTGCTGGCATGCCGCGCCTCCCAGAGGCCCACCTTCAAGCAGCTGGT
GGAGGACCTGGACCGTGTCCTTACCGTGACGTCCACCGACGAGTACCTGGACCTGTCGGCGCCTTTCGAGCAGTACTCCC
CGGGTGGCCAGGACACCCCCAGCTCCAGCTCCTCAGGGGACGACTCCGTGTTTGCCCACGACCTGCTGCCCCGGCCCCA
CCCAGCAGTGGGGGCTCGCGGACGTGA
```

Figure 2P    Mutant 1

Mutant G382R FGFR3-IIIb:

```
ATGGGCGCCCCTGCCTGCGCCCTCGCGCTCTGCGTGGCCGTGGCCATCGTGGCCGGCGCCTCCTCGGAGTCCTTGGGGAC
GGAGCAGCGCGTCGTGGGGCGAGCGGCAGAAGTCCCGGGCCCAGAGCCCGGCCAGCAGGAGCAGTTGGTCTTCGGCAGCG
GGGATGCTGTGGAGCTGAGCTGTCCCCCGCCCGGGGGTGGTCCCATGGGGCCCACTGTCTGGGTCAAGGATGGCACAGGG
CTGGTGCCCTCGGAGCGTGTCCTGGTGGGGCCCCAGCGGCTGCAGGTGCTGAATGCCTCCCACGAGGACTCCGGGGCCTA
CAGCTGCCGGCAGCGGCTCACGCAGCGCGTACTGTGCCACTTCAGTGTGCGGGTGACAGACGCTCCATCCTCGGGAGATG
ACGAAGACGGGGAGGACGAGGCTGAGGACACAGGTGTGGACACAGGGGCCCCTTACTGGACACGGCCCGAGCGGATGGAC
AAGAAGCTGCTGGCCGTGCCGGCCGCCAACACCGTCCGCTTCCGCTGCCCAGCCGCTGGCAACCCCACTCCCTCCATCTC
CTGGCTGAAGAACGGCAGGGAGTTCCGCGGCGAGCACCGCATTGGAGGCATCAAGCTGCGGCATCAGCAGTGGAGCCTGG
TCATGGAAAGCGTGGTGCCCTCGGACCGCGGCAACTACACCTGCGTCGTGGAGAACAAGTTTGGCAGCATCCGGCAGACG
TACACGCTGGACGTGCTGGAGCGCTCCCCGCACCGGCCCATCCTGCAGGCGGGGCTGCCGGCCAACCAGACGGCGGTGCT
GGGCAGCGACGTGGAGTTCCACTGCAAGGTGTACAGTGACGCACAGCCCCACATCCAGTGGCTCAAGCACGTGGAGGTGA
ACGGCAGCAAGGTGGGCCCGGACGGCACACCCTACGTTACCGTGCTCAAGTCCTGGATCAGTGAGAGTGTGGAGGCCGAC
GTGCGCCTCCGCCTGGCCAATGTGTCGGAGCGGGACGGGGGCGAGTACCTCTGTCGAGCCACCAATTTCATAGGCGTGGC
CGAGAAGGCCTTTTGGCTGAGCGTTCACGGGCCCGAGCAGCCGAGGAGGAGCTGGTGGAGGCTGACGAGGCGGGCAGTG
TGTATGCAGGCATCCTCAGCTACAGGGTGGGCTTCTTCCTGTTCATCCTGGTGGTGGCGGCTGTGACGCTCTGCCGCCTG
CGCAGCCCCCCAAGAAAGGCCTGGGCTCCCCACCGTGCACAAGATCTCCCGCTTCCCGCTCAAGCGACAGGTGTCCCT
GGAGTCCAACGCGTCCATGAGCTCCAACACACCACTGGTGCGCATCGCAAGGCTGTCCTCAGGGGAGGGCCCACGCTGG
CCAATGTCTCCGAGCTCGAGCTGCCTGCCGACCCCAAATGGGAGCTGTCTCGGGCCCGGCTGACCCTGGGCAAGCCCCTT
GGGGAGGGCTGCTTCGGCCAGGTGGTCATGGCGGAGGCCATCGGCATTGACAAGGACCGGGCCGCCAAGCCTGTCACCGT
AGCCGTGAAGATGCTGAAAGACGATGCCACTGACAAGGACCTGTCGGACCTGGTGTCTGAGATGGAGATGATGAAGATGA
TCGGGAAACACAAAAACATCATCAACCTGCTGGGCGCCTGCACGCAGGGCGGGCCCCTGTACGTGCTGGTGGAGTACGCG
GCCAAGGGTAACCTGCGGGAGTTTCTGCGGGCGCGGCGGCCCCGGGCCTGGACTACTCCTTCGACACCTGCAAGCCGCC
CGAGGAGCAGCTCACCTTCAAGGACCTGGTGTCCTGTGCCTACCAGGTGGCCCGGGGCATGGAGTACTTGGCCTCCCAGA
AGTGCATCCACAGGGACCTGGCTGCCCGCAATGTGCTGGTGACCGAGGACAACGTGATGAAGATCGCAGACTTCGGGCTG
GCCCGGGACGTGCACAACCTCGACTACTACAAGAAGACAACCAACGGCCGGCTGCCCGTGAAGTGGATGGCGCCTGAGGC
CTTGTTTGACCGAGTCTACACTCACCAGAGTGACGTCTGGTCCTTTGGGGTCCTGCTCTGGGAGATCTTCACGCTGGGGG
GCTCCCCGTACCCCGGCATCCCTGTGGAGGAGCTCTTCAAGCTGCTGAAGGAGGGCCACCGCATGGACAAGCCCGCCAAC
TGCACACACGACCTGTACATGATCATGCGGGAGTGCTGGCATGCCGCGCCCTCCCAGAGGCCCACCTTCAAGCAGCTGGT
GGAGGACCTGGACCGTGTCCTTACCGTGACGTCCACCGACGAGTACCTGGACCTGTCGGCGCCTTTCGAGCAGTACTCCC
CGGGTGGCCAGGACACCCCCAGCTCCAGCTCCTCAGGGGACGACTCCGTGTTTGCCCACGACCTGCTGCCCCCGGCCCCA
CCCAGCAGTGGGGGCTCGCGGACGTGA
```

Figure 2Q  Mutant 2

Mutant G382R FGFR3-IIIb:

ATGGGCGCCCCTGCCTGCGCCCTCGCGCTCTGCGTGGCCGTGGCCATCGTGGCCGGCGCCTCCTCGGAGTCCTTGGGGAC
GGAGCAGCGCGTCGTGGGGCGAGCGGCAGAAGTCCCGGGCCCAGAGCCCGGCCAGCAGGAGCAGTTGGTCTTCGGCAGCG
GGGATGCTGTGGAGCTGAGCTGTCCCCCGCCCGGGGGTGGTCCCATGGGGCCCACTGTCTGGGTCAAGGATGGCACAGGG
CTGGTGCCCTCGGAGCGTGTCCTGGTGGGGCCCCAGCGGCTGCAGGTGCTGAATGCCTCCCACGAGGACTCCGGGGCCTA
CAGCTGCCGGCAGCGGCTCACGCAGCGCGTACTGTGCCACTTCAGTGTGCGGGTGACAGACGCTCCATCCTCGGGAGATG
ACGAAGACGGGGAGGACGAGGCTGAGGACACAGGTGTGGACACAGGGGCCCCTTACTGGACACGGCCCGAGCGGATGGAC
AAGAAGCTGCTGGCCGTGCCGGCCGCCAACACCGTCCGCTTCCGCTGCCCAGCCGCTGGCAACCCCACTCCCTCCATCTC
CTGGCTGAAGAACGGCAGGGAGTTCCGCGGCGAGCACCGCATTGGAGGCATCAAGCTGCGGCATCAGCAGTGGAGCCTGG
TCATGGAAAGCGTGGTGCCCTCGGACCGCGGCAACTACACCTGCGTCGTGGAGAACAAGTTTGGCAGCATCCGGCAGACG
TACACGCTGGACGTGCTGGAGCGCTCCCCGCACCGGCCCATCCTGCAGGCGGGGCTGCCGGCCAACCAGACGGCGGTGCT
GGGCAGCGACGTGGAGTTCCACTGCAAGGTGTACAGTGACGCACAGCCCCACATCCAGTGGCTCAAGCACGTGGAGGTGA
ACGGCAGCAAGGTGGGCCCGGACGGCACACCCTACGTTACCGTGCTCAAGTCCTGGATCAGTGAGAGTGTGGAGGCCGAC
GTGCGCCTCCGCCTGGCCAATGTGTCGGAGCGGGACGGGGGCGAGTACCTCTGTCGAGCCACCAATTTCATAGGCGTGGC
CGAGAAGGCCTTTTGGCTGAGCGTTCACGGGCCCCGAGCAGCCGAGGAGGAGCTGGTGGAGGCTGACGAGGCGGGCAGTG
TGTATGCAGGCATCCTCAGCTACCGGGTGGGCTTCTTCCTGTTCATCCTGGTGGTGGCGGCTGTGACGCTCTGCCGCCTG
CGCAGCCCCCCCAAGAAAGGCCTGGGCTCCCCCACCGTGCACAAGATCTCCCGCTTCCCGCTCAAGCGACAGGTGTCCCT
GGAGTCCAACGCGTCCATGAGCTCCAACACACCACTGGTGCGCATCGCAAGGCTGTCCTCAGGGGAGGGCCCCACGCTGG
CCAATGTCTCCGAGCTCGAGCTGCCTGCCGACCCCAAATGGGAGCTGTCTCGGGCCCGGCTGACCCTGGGCAAGCCCCTT
GGGGAGGGCTGCTTCGGCCAGGTGGTCATGGCGGAGGCCATCGGCATTGACAAGGACCGGGCCGCCAAGCCTGTCACCGT
AGCCGTGAAGATGCTGAAAGACGATGCCACTGACAAGGACCTGTCGGACCTGGTGTCTGAGATGGAGATGATGAAGATGA
TCGGGAAACACAAAAACATCATCAACCTGCTGGGCGCCTGCACGCAGGGCGGGCCCCTGTACGTGCTGGTGGAGTACGCG
GCCAAGGGTAACCTGCGGGAGTTTCTGCGGGCGCGGCGGCCCCCGGGCCTGGACTACTCCTTCGACACCTGCAAGCCGCC
CGAGGAGCAGCTCACCTTCAAGGACCTGGTGTCCTGTGCCTACCAGGTGGCCGGGGCATGGAGTACTTGGCCTCCCAGA
AGTGCATCCACAGGGACCTGGCTGCCCGCAATGTGCTGGTGACCGAGGACAACGTGATGAAGATCGCAGACTTCGGGCTG
GCCCGGGACGTGCACAACCTCGACTACTACAAGAAGACAACCAACGGCCGGCTGCCCGTGAAGTGGATGGCGCCTGAGGC
CTTGTTTGACCGAGTCTACACTCACCAGAGTGACGTCTGGTCCTTTGGGGTCCTGCTCTGGGAGATCTTCACGCTGGGGG
GCTCCCCGTACCCCGGCATCCCTGTGGAGGAGCTCTTCAAGCTGCTGAAGGAGGGCCACCGCATGGACAAGCCCGCCAAC
TGCACACACGACCTGTACATGATCATGCGGGAGTGCTGGCATGCCGCGCCCTCCCAGAGGCCCACCTTCAAGCAGCTGGT
GGAGGACCTGGACCGTGTCCTTACCGTGACGTCCACCGACGAGTACCTGGACCTGTCGGCGCCTTTCGAGCAGTACTCCC
CGGGTGGCCAGGACACCCCCAGCTCCAGCTCCTCAGGGGACGACTCCGTGTTTGCCCACGACCTGCTGCCCCGGCCCCA
CCCAGCAGTGGGGGCTCGCGGACGTGA

Figure 2R

Mutant G377C FGFR3-IIIb:

```
ATGGGCGCCCCTGCCTGCGCCCTCGCGCTCTGCGTGGCCGTGGCCATCGTGGCCGGCGCCTCCTCGGAGTCCTTGGGGAC
GGAGCAGCGCGTCGTGGGGCGAGCGGCAGAAGTCCCGGGCCCAGAGCCCGGCCAGCAGGAGCAGTTGGTCTTCGGCAGCG
GGGATGCTGTGGAGCTGAGCTGTCCCCCGCCCGGGGGTGGTCCCATGGGGCCCACTGTCTGGGTCAAGGATGGCACAGGG
CTGGTGCCCTCGGAGCGTGTCCTGGTGGGGCCCCAGCGGCTGCAGGTGCTGAATGCCTCCCACGAGGACTCCGGGGCCTA
CAGCTGCCGGCAGCGGCTCACGCAGCGCGTACTGTGCCACTTCAGTGTGCGGGTGACAGACGCTCCATCCTCGGGAGATG
ACGAAGACGGGGAGGACGAGGCTGAGGACACAGGTGTGGACACAGGGGCCCCTTACTGGACACGGCCCGAGCGGATGGAC
AAGAAGCTGCTGGCCGTGCCGGCCGCCAACACCGTCCGCTTCCGCTGCCCAGCCGCTGGCAACCCCACTCCCTCCATCTC
CTGGCTGAAGAACGGCAGGGAGTTCCGCGGCGAGCACCGCATTGGAGGCATCAAGCTGCGGCATCAGCAGTGGAGCCTGG
TCATGGAAAGCGTGGTGCCCTCGGACCGCGGCAACTACACCTGCGTCGTGGAGAACAAGTTTGGCAGCATCCGGCAGACG
TACACGCTGGACGTGCTGGAGCGCTCCCCGCACCGGCCCATCCTGCAGGCGGGGCTGCCGGCCAACCAGACGGCGGTGCT
GGGCAGCGACGTGGAGTTCCACTGCAAGGTGTACAGTGACGCACAGCCCCACATCCAGTGGCTCAAGCACGTGGAGGTGA
ACGGCAGCAAGGTGGGCCCGGACGGCACACCCTACGTTACCGTGCTCAAGTCCTGGATCAGTGAGAGTGTGGAGGCCGAC
GTGCGCCTCCGCCTGGCCAATGTGTCGGAGCGGGACGGGGGCGAGTACCTCTGTCGAGCCACCAATTTCATAGGCGTGGC
CGAGAAGGCCTTTTGGCTGAGCGTTCACGGGCCCCGAGCAGCCGAGGAGGAGCTGGTGGAGGCTGACGAGGCGGGCAGTG
TGTATGCATGCATCCTCAGCTACGGGGTGGGCTTCTTCCTGTTCATCCTGGTGGTGGCGGCTGTGACGCTCTGCCGCCTG
CGCAGCCCCCCCAAGAAAGGCCTGGGCTCCCCCACCGTGCACAAGATCTCCCGCTTCCCGCTCAAGCGACAGGTGTCCCT
GGAGTCCAACGCGTCCATGAGCTCCAACACACCACTGGTGCGCATCGCAAGGCTGTCCTCAGGGGAGGGCCCCACGCTGG
CCAATGTCTCCGAGCTCGAGCTGCCTGCCGACCCCAAATGGGAGCTGTCTCGGGCCCGGCTGACCCTGGGCAAGCCCCTT
GGGGAGGGCTGCTTCGGCCAGGTGGTCATGGCGGAGGCCATCGGCATTGACAAGGACCGGGCCGCCAAGCCTGTCACCGT
AGCCGTGAAGATGCTGAAAGACGATGCCACTGACAAGGACCTGTCGGACCTGGTGTCTGAGATGGAGATGATGAAGATGA
TCGGGAAACACAAAAACATCATCAACCTGCTGGGCGCCTGCACGCAGGGCGGGCCCCTGTACGTGCTGGTGGAGTACGCG
GCCAAGGGTAACCTGCGGGAGTTTCTGCGGGCGCGGCGGCCCCGGGCCTGGACTACTCCTTCGACACCTGCAAGCCGCC
CGAGGAGCAGCTCACCTTCAAGGACCTGGTGTCCTGTGCCTACCAGGTGGCCCGGGGCATGGAGTACTTGGCCTCCCAGA
AGTGCATCCACAGGGACCTGGCTGCCCGCAATGTGCTGGTGACCGAGGACAACGTGATGAAGATCGCAGACTTCGGGCTG
GCCCGGGACGTGCACAACCTCGACTACTACAAGAAGACAACCAACGGCCGGCTGCCCGTGAAGTGGATGGCGCCTGAGGC
CTTGTTTGACCGAGTCTACACTCACCAGAGTGACGTCTGGTCCTTTGGGGTCCTGCTCTGGGAGATCTTCACGCTGGGGG
GCTCCCCGTACCCCGGCATCCCTGTGGAGGAGCTCTTCAAGCTGCTGAAGGAGGGCCACCGCATGGACAAGCCCGCCAAC
TGCACACACGACCTGTACATGATCATGCGGGAGTGCTGGCATGCCGCGCCCTCCCAGAGGCCCACCTTCAAGCAGCTGGT
GGAGGACCTGGACCGTGTCCTTACCGTGACGTCCACCGACGAGTACCTGGACCTGTCGGCGCCTTTCGAGCAGTACTCCC
CGGGTGGCCAGGACACCCCAGCTCCAGCTCCTCAGGGGACGACTCCGTGTTTGCCCACGACCTGCTGCCCCCGGCCCCA
CCCAGCAGTGGGGGCTCGCGGACGTGA
```

Figure 2S

Mutant A393E FGFR3-IIIb:

```
ATGGGCGCCCCTGCCTGCGCCCTCGCGCTCTGCGTGGCCGTGGCCATCGTGGCCGGCGCCTCCTCGGAGTCCTTGGGGAC
GGAGCAGCGCGTCGTGGGGCGAGCGGCAGAAGTCCCGGGCCCAGAGCCCGGCCAGCAGGAGCAGTTGGTCTTCGGCAGCG
GGGATGCTGTGGAGCTGAGCTGTCCCCCGCCCGGGGGTGGTCCCATGGGGCCCACTGTCTGGGTCAAGGATGGCACAGGG
CTGGTGCCCTCGGAGCGTGTCCTGGTGGGGCCCCAGCGGCTGCAGGTGCTGAATGCCTCCCACGAGGACTCCGGGGCCTA
CAGCTGCCGGCAGCGGCTCACGCAGCGCGTACTGTGCCACTTCAGTGTGCGGGTGACAGACGCTCCATCCTCGGGAGATG
ACGAAGACGGGGAGGACGAGGCTGAGGACACAGGTGTGGACACAGGGGCCCCTTACTGGACACGGCCCGAGCGGATGGAC
AAGAAGCTGCTGGCCGTGCCGGCCGCCAACACCGTCCGCTTCCGCTGCCCAGCCGCTGGCAACCCCACTCCCTCCATCTC
CTGGCTGAAGAACGGCAGGGAGTTCCGCGGCGAGCACCGCATTGGAGGCATCAAGCTGCGGCATCAGCAGTGGAGCCTGG
TCATGGAAAGCGTGGTGCCCTCGGACCGCGGCAACTACACCTGCGTCGTGGAGAACAAGTTTGGCAGCATCCGGCAGACG
TACACGCTGGACGTGCTGGAGCGCTCCCCGCACCGGCCCATCCTGCAGGCGGGGCTGCCGGCCAACCAGACGGCGGTGCT
GGGCAGCGACGTGGAGTTCCACTGCAAGGTGTACAGTGACGCACAGCCCCACATCCAGTGGCTCAAGCACGTGGAGGTGA
ACGGCAGCAAGGTGGGCCCGGACGGCACACCCTACGTTACCGTGCTCAAGTCCTGGATCAGTGAGAGTGTGGAGGCCGAC
GTGCGCCTCCGCCTGGCCAATGTGTCGGAGCGGGACGGGGGCGAGTACCTCTGTCGAGCCACCAATTTCATAGGCGTGGC
CGAGAAGGCCTTTTGGCTGAGCGTTCACGGGCCCCGAGCAGCCGAGGAGGAGCTGGTGGAGGCTGACGAGGCGGGCAGTG
TGTATGCAGGCATCCTCAGCTACGGGGTGGGCTTCTTCCTGTTCATCCTGGTGGTGGAGGCTGTGACGCTCTGCCGCCTG
CGCAGCCCCCCCAAGAAAGGCCTGGGCTCCCCCACCGTGCACAAGATCTCCCGCTTCCCGCTCAAGCGACAGGTGTCCCT
GGAGTCCAACGCGTCCATGAGCTCCAACACACCACTGGTGCGCATCGCAAGGCTGTCCTCAGGGGAGGGCCCCACGCTGG
CCAATGTCTCCGAGCTCGAGCTGCCTGCCGACCCCAAATGGGAGCTGTCTCGGGCCCGGCTGACCCTGGGCAAGCCCCTT
GGGGAGGGCTGCTTCGGCCAGGTGGTCATGGCGGAGGCCATCGGCATTGACAAGGACCGGGCCGCCAAGCCTGTCACCGT
AGCCGTGAAGATGCTGAAAGACGATGCCACTGACAAGGACCTGTCGGACCTGGTGTCTGAGATGGAGATGATGAAGATGA
TCGGGAAACACAAAAACATCATCAACCTGCTGGGCGCCTGCACGCAGGGCGGGCCCCTGTACGTGCTGGTGGAGTACGCG
GCCAAGGGTAACCTGCGGGAGTTTCTGCGGGCGCGGCGGCCCCCGGGCCTGGACTACTCCTTCGACACCTGCAAGCCGCC
CGAGGAGCAGCTCACCTTCAAGGACCTGGTGTCCTGTGCCTACCAGGTGGCCCGGGGCATGGAGTACTTGGCCTCCCAGA
AGTGCATCCACAGGGACCTGGCTGCCCGCAATGTGCTGGTGACCGAGGACAACGTGATGAAGATCGCAGACTTCGGGCTG
GCCCGGGACGTGCACAACCTCGACTACTACAAGAAGACAACCAACGGCCGGCTGCCCGTGAAGTGGATGGCGCCTGAGGC
CTTGTTTGACCGAGTCTACACTCACCAGAGTGACGTCTGGTCCTTTGGGGTCCTGCTCTGGGAGATCTTCACGCTGGGGG
GCTCCCCGTACCCCGGCATCCCTGTGGAGGAGCTCTTCAAGCTGCTGAAGGAGGGCCACCGCATGGACAAGCCCGCCAAC
TGCACACACGACCTGTACATGATCATGCGGGAGTGCTGGCATGCCGCGCCCTCCCAGAGGCCCACCTTCAAGCAGCTGGT
GGAGGACCTGGACCGTGTCCTTACCGTGACGTCCACCGACGAGTACCTGGACCTGTCGGCGCCTTTCGAGCAGTACTCCC
CGGGTGGCCAGGACACCCCCAGCTCCAGCTCCTCAGGGGACGACTCCGTGTTTGCCCACGACCTGCTGCCCCCGGCCCCA
CCCAGCAGTGGGGGCTCGCGGACGTGA
```

Figure 2T

Mutant P250R FGFR3-IIIb:

```
ATGGGCGCCCCTGCCTGCGCCCTCGCGCTCTGCGTGGCCGTGGCCATCGTGGCCGGCGCCTCCTCGGAGTCCTTGGGGAC
GGAGCAGCGCGTCGTGGGGCGAGCGGCAGAAGTCCCGGGCCCAGAGCCCGGCCAGCAGGAGCAGTTGGTCTTCGGCAGCG
GGGATGCTGTGGAGCTGAGCTGTCCCCCGCCCGGGGGTGGTCCCATGGGGCCCACTGTCTGGGTCAAGGATGGCACAGGG
CTGGTGCCCTCGGAGCGTGTCCTGGTGGGGCCCCAGCGGCTGCAGGTGCTGAATGCCTCCCACGAGGACTCCGGGGCCTA
CAGCTGCCGGCAGCGGCTCACGCAGCGCGTACTGTGCCACTTCAGTGTGCGGGTGACAGACGCTCCATCCTCGGGAGATG
ACGAAGACGGGGAGGACGAGGCTGAGGACACAGGTGTGGACACAGGGGCCCCTTACTGGACACGGCCCGAGCGGATGGAC
AAGAAGCTGCTGGCCGTGCCGGCCGCCAACACCGTCCGCTTCCGCTGCCCAGCCGCTGGCAACCCCACTCCCTCCATCTC
CTGGCTGAAGAACGGCAGGGAGTTCCGCGGCGAGCACCGCATTGGAGGCATCAAGCTGCGGCATCAGCAGTGGAGCCTGG
TCATGGAAAGCGTGGTGCCCTCGGACCGCGGCAACTACACCTGCGTCGTGGAGAACAAGTTTGGCAGCATCCGGCAGACG
TACACGCTGGACGTGCTGGAGCGCTCCCGGCACCGGCCCATCCTGCAGGCGGGGCTGCCGGCCAACCAGACGGCGGTGCT
GGGCAGCGACGTGGAGTTCCACTGCAAGGTGTACAGTGACGCACAGCCCCACATCCAGTGGCTCAAGCACGTGGAGGTGA
ACGGCAGCAAGGTGGGCCCGGACGGCACACCCTACGTTACCGTGCTCAAGTCCTGGATCAGTGAGAGTGTGGAGGCCGAC
GTGCGCCTCCGCCTGGCCAATGTGTCGGAGCGGGACGGGGGCGAGTACCTCTGTCGAGCCACCAATTTCATAGGCGTGGC
CGAGAAGGCCTTTTGGCTGAGCGTTCACGGGCCCCGAGCAGCCGAGGAGGAGCTGGTGGAGGCTGACGAGGCGGGCAGTG
TGTATGCAGGCATCCTCAGCTACGGGGTGGGCTTCTTCCTGTTCATCCTGGTGGTGGCGGCTGTGACGCTCTGCCGCCTG
CGCAGCCCCCCCAAGAAAGGCCTGGGCTCCCCCACCGTGCACAAGATCTCCCGCTTCCCGCTCAAGCGACAGGTGTCCCT
GGAGTCCAACGCGTCCATGAGCTCCAACACACCACTGGTGCGCATCGCAAGGCTGTCCTCAGGGGAGGGCCCCACGCTGG
CCAATGTCTCCGAGCTCGAGCTGCCTGCCGACCCCAAATGGGAGCTGTCTCGGGCCCGGCTGACCCTGGGCAAGCCCCTT
GGGGAGGGCTGCTTCGGCCAGGTGGTCATGGCGGAGGCCATCGGCATTGACAAGGACCGGGCCGCCAAGCCTGTCACCGT
AGCCGTGAAGATGCTGAAAGACGATGCCACTGACAAGGACCTGTCGGACCTGGTGTCTGAGATGGAGATGATGAAGATGA
TCGGGAAACACAAAAACATCATCAACCTGCTGGGCGCCTGCACGCAGGGCGGGCCCCTGTACGTGCTGGTGGAGTACGCG
GCCAAGGGTAACCTGCGGGAGTTTCTGCGGGCGCGGCGGCCCCGGGCCTGGACTACTCCTTCGACACCTGCAAGCCGCC
CGAGGAGCAGCTCACCTTCAAGGACCTGGTGTCCTGTGCCTACCAGGTGGCCCGGGGCATGGAGTACTTGGCCTCCCAGA
AGTGCATCCACAGGGACCTGGCTGCCCGCAATGTGCTGGTGACCGAGGACAACGTGATGAAGATCGCAGACTTCGGGCTG
GCCCGGGACGTGCACAACCTCGACTACTACAAGAAGACAACCAACGGCCGGCTGCCCGTGAAGTGGATGGCGCCTGAGGC
CTTGTTTGACCGAGTCTACACTCACCAGAGTGACGTCTGGTCCTTTGGGGTCCTGCTCTGGGAGATCTTCACGCTGGGGG
GCTCCCCGTACCCCGGCATCCCTGTGGAGGAGCTCTTCAAGCTGCTGAAGGAGGGCCACCGCATGGACAAGCCCGCCAAC
TGCACACACGACCTGTACATGATCATGCGGGAGTGCTGGCATGCCGCGCCCTCCCAGAGGCCCACCTTCAAGCAGCTGGT
GGAGGACCTGGACCGTGTCCTTACCGTGACGTCCACCGACGAGTACCTGGACCTGTCGGCGCCTTTCGAGCAGTACTCCC
CGGGTGGCCAGGACACCCCCAGCTCCAGCTCCTCAGGGGACGACTCCGTGTTTGCCCACGACCTGCTGCCCCCGGCCCCA
CCCAGCAGTGGGGGCTCGCGGACGTGA
```

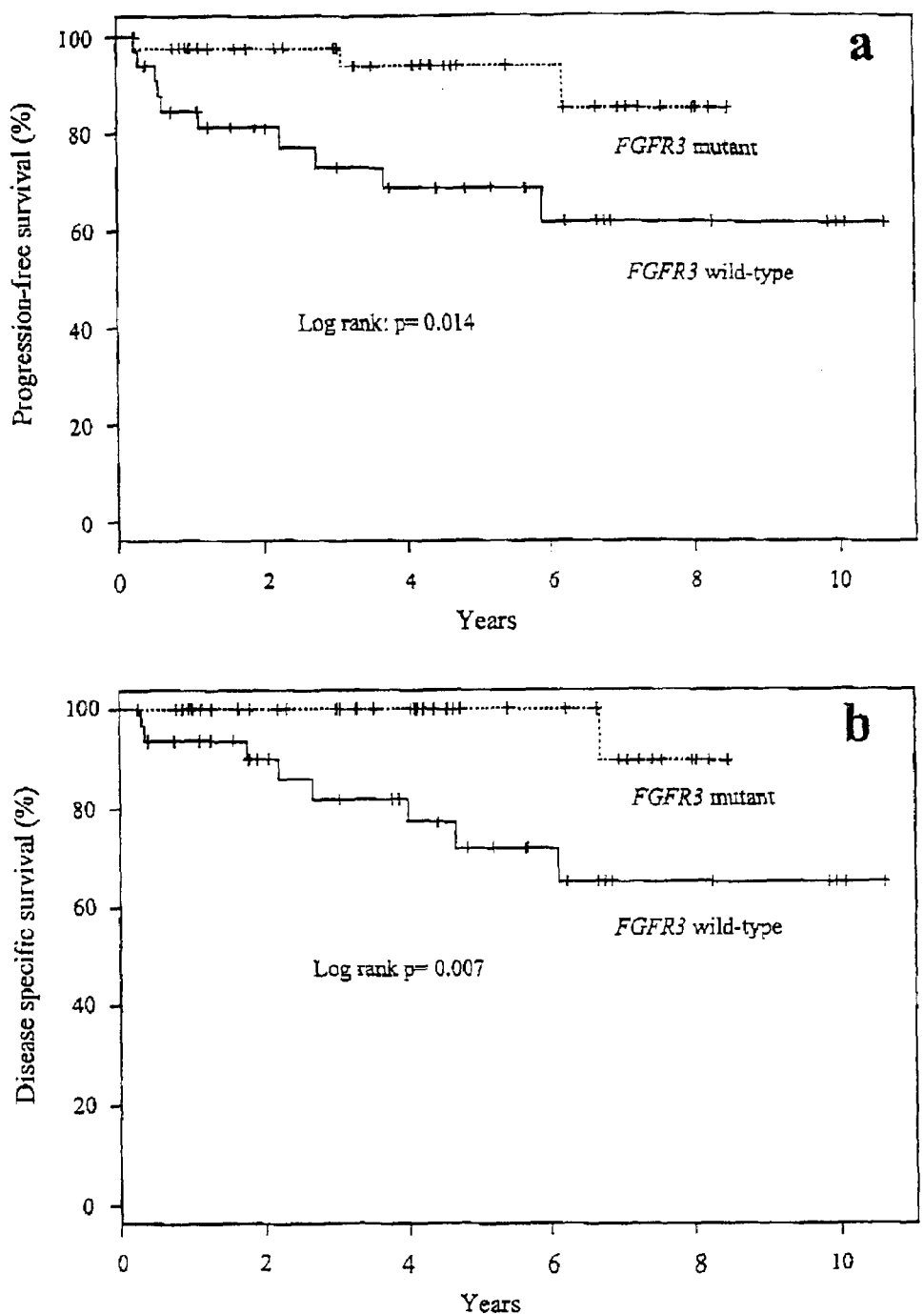

MEANS FOR DETECTING AND TREATING PATHOLOGIES LINKED TO FGFR3

The present application is a 371 U.S. national phase of PCT/EP00/04591, filed May 4, 2000, which designated the U.S., and claims benefit of U.S. provisional application Ser. No. 60/132,705, filed May 5, 1999.

The invention relates to means, i.e. method and drugs, for detecting and treating, respectively, pathologies linked to FGFR3 and/or to the FGFR3 pathway.

Fibroblast growth factor receptor 3 (FGFR3) belongs to a family of structurally related tyrosine kinase receptors (FG-FRs 1–4) encoded by four different genes. These receptors are glycoproteins composed of two to three extracellular immunoglobulin (Ig)-like domains, a transmembrane domain and a split tyrosine-kinase domain. Alternative mRNA splicing results in many different receptors variants. Isoforms FGFR3-IIIb and FGFR3-IIIc result from a mutually exclusive splicing event in which the second half of the juxtamembrane Ig-like domain is encoded either by the 151 nucleotides long exon 8 (IIIb variant) or the 145 nucleotides long exon 9 (IIIc variant).

Specific point mutations in the FGFR3 gene which affect different domains of the protein are associated with autosomal dominant human skeletal disorders such as hypochondroplasia, achondroplasia, severe achondroplasia with developmental delay and acanthosis nigricans and thanatophoric dysplasia. Several reports have demonstrated that these mutations lead to constitutive activation of the receptor. Taking into account this result, together with the skeletal overgrowth observed in mice homozygous for null alleles of Fgfr3. FGFR3 appears as a negative regulator of bone growth.

In contrast with this inhibitory role, an oncogenic role has been proposed for FGFR3 in multiple myeloma (MM) development. In this malignant proliferation of plasma cells, a t(4;14)(p16.3;q32.3) chromosomal translocation with breakpoints located 50 to 100 Kb centromeric to FGFR3 is present in 20–25% of the cases and is associated with overexpression of FGFR3.

In very rare cases (2 out of 12 MM cell lines and 1 out of 85 primary MM tumours), activating mutations of FGFR3 previously identified in human skeletal disorders have been found, but always accompanied by the t(4;14)(p16.3;q32.3) translocation.

By investigating various cancers, the inventors have surprisingly found a role for FGFR3 in solid tumours, in particular in cancers originating from epithelial tissues, carcinomas.

The involvement of FGFR3 in such solid tumour development is linked to a constitutional activation, it may be activated by an autocrinal loop (ligand self-production) and/or by activating mutations in FGFR3. Surprisingly, such mutations are found in primary tumours and are somatic mutations (genomic DNA mutations).

So far, the only FGFR3 isoform which has been identified in epithelium is the FGFR3-IIIb isoform.

The invention thus relates to a method and kits for detecting such pathologies.

According to another aspect, the invention also relates to drugs capable of treating such pathologies.

According to still another aspect, it relates to transgenic animals enabling the efficiency of such drugs to be tested as well as to cell lines transfected with the different forms of FGFR3 (useful in vitro and in vivo).

The method of the invention for detecting carcinomas in a biological sample comprises identifying FGFR3 mutations.

Standard methods can apply for such an identification such as immunohistochemistry, or detection of the corresponding RNA, DNA, and encoded protein contained in said sample, particularly after extraction thereof. A common way for such a detection comprises amplifying by PCR, RT-PCR or RT-PCR SSCP (single strand conformation polymorphism) with FGFR3 specific primers and revealing the amplification products according to the usual methods. A corresponding embodiment is exemplified in the examples given hereinafter. Another common way comprises the use of antibodies and the detection of the antigen-antibody reaction with appropriate labelling.

The activating function of a mutation can be determined by observation of activating signals such as receptor phosphorylation, cell proliferation (e.g. thymidine incorporation) or indirect effects such as calcium influx, phosphorylation of target sequences.

More particularly, said identification comprises screening for single nucleotide mutation(s) in the genomic DNA and/or its products, i.e. RNA, protein, the term "product" also encompassing cDNA.

Particularly, said method comprises screening for mutations creating cysteine residues in the extracellular or transmembrane domains of the receptor.

Alternatively, or in combination with the foregoing embodiment, it comprises screening for mutations resulting in at least one amino-acid substitution in the kinase domain of the receptor.

It particularly comprises screening of activating mutation(s) of FGFR3, notably such as above-described.

More particularly, the method of the invention comprises screening for mutation(s) in exon 7, encoding the junction between immunoglobulin-like domains II and III of FGFR3, in exon 10, encoding the transmembrane domain, in exon 15, encoding the tyrosine kinase domain I, and/or in the exon encoding the C-terminal part.

Advantageously, the method of the invention comprises screening for missense mutations such as implicated in thanatophoric dysplasia, NSC, achondroplasia, saddan, or hypochondroplasia.

Such FGFR3 mutations notably comprise R248C, S249C, G372C, S373C, Y375C, K652E, K652M, J809G, J809C, J809R, J809L, P250R, G377C, G382R, A393E, N542K (codons are numbered according to FGFR3-IIIb cDNA open reading frame).

The following FGFR3 mutations will be particularly identified: R248C, S249C, G372C, K652E and Y375C.

Said biological sample used in the method of the invention will advantageously comprise a tissue, bone marrow, or a fluid such as blood, urine, deriving from a warm-blooded animal, and more especially from a human.

Said method is particularly useful for detecting carcinomas, such as human bladder and cervix carcinomas. A major issue in superficial bladder cancer is to distinguish tumours which will progress from those which will not. Insights into the genetic and epigenetic alterations involved in bladder cancer is expected to provide useful information to facilitate this distinction. In that respect, the invention provides means to resolve the dilemma between a bladder-sparing strategy versus cystectomy and will contribute to a more individualised intravesical instillation and endoscopic monitoring policy.

Indeed, as shown by the results given in the examples, FGFR3 appears to be a major oncogene in Ta, T1 bladder carcinomas. The FGFR3 mutations appear to be frequently associated with tumours that do not progress. Multivariate analysis showed that FGFR3 mutation status remained a statistically significant predictor of good outcome. FGFR3 mutations thus provide clear-cut information, which may complement stage and grade. The use of these mutations alone and/or in combination with other predictors of tumour aggressiveness will then provide relevant prognostic information.

Said method, will also be used for detecting for example lung, breast, colon, skin cancers.

The method of detection according to the invention applies to the diagnostic of carcinomas, as well to the prognosis, or the follow-up of the efficiency of a therapy.

Said method will advantageously be performed by using kits comprising the appropriate reagents and a notice of use.

According to another aspect, the invention relates to drugs having an anti-proliferative effect on carcinoma cells. Such drugs comprise, as active principle(s) agent(s) which act by inhibition of FGFR3 DNA synthesis or by inhibition of its expression products (RNA, proteins). Particularly, such drugs contain tyrosine kinase inhibitors specific for FGFR3.

Other appropriate inhibitors comprise antibodies directed against FGFR3, and particularly against at least one extracellular Ig-like domain thereof. Advantageously said antibodies are specific for FGFR3-IIIb. Preferred antibodies are monoclonal ones, and particularly antibodies modified so that they do not induce immunogenic reactions in a human body (e.g. humanized antibodies).

Other appropriate inhibitors comprise antisens oligonucleotides directed against a wild or mutated FGFR3 isoform.

The administration and the posology of said inhibitors will be determined by the one skilled in the art depending on the carcinoma to be treated, the weight and age of the patient. For example, antibodies will be administered by the injectable route.

The invention thus gives means of great interest for detecting and treating carcinomas, taking into account the fact that cancers originating from epithelial tissues (carcinomas) represent approximately 90% of malignant neoplasms.

The invention also relates to cell lines capable of expressing FGFR3 mutated forms. Particularly, the invention relates to FGFR3 S249C mutated forms. T24 cell lines constitutively expressing FGFR3 S249C mutated forms and HeLa cell lines expressing FGFR3 S249C mutated forms in an inducible manner have thus been obtained (for example see ref. (6)).

By injecting such cell lines to nude mice, an increased tumorigenicity was observed.

According to the invention, such cell lines are useful in vitro (follow up of the receptor phosphorylation) or in vivo (examination of the tumorigenicity of nude mice) to study the inhibitor effect against FGFR3.

Cell lines transfected with FGFR2, FGFR1 or FGFR4 are particularly useful for studying the specificity of inhibitors to be tested.

According to still another object, the invention relates to constructions capable of expressing by transgenesis a FGFR3 mutated form in epitheliums and the transgenic animals thus obtained which are characterized by the fact that they comprise such constructions.

Examples of constructions intended for injection in animal germinal cells comprise a keratin promoter, particularly keratin 14 promoter and cDNA of mutated FGFR3.

Other advantages and characteristics of the invention will be given in the following examples wherein it will be referred to FIGS. 1A–1B which give FGFR3-IIIb gene activating mutations in primary tumours (Patient 745.1, SEQ ID NO:21; Patient 813, SEQ ID NO:22; Patient 1447, SEQ ID NO:23; Patient 1084, SEQ ID NO:24), FIGS. 2A–2E which refer to FGFR3-IIIb wild (2A, SEQ ID NO:1) and mutated pro-oncogenic (2B–2T (SEQ ID NOs:2–20, respectively)) sequences. It will be noted that the sequences of FIGS. 2B to 2T (SEQ ID NOs:2–20, respectively), as such, enter into the scope of the invention. There may be silent polymorphisms all along the sequence, so there may be in fact several possible sequences for each mutant, and FIG. 3a and 3b which respectively represent a) Kaplan-Meier progression-free survival curves according to FGFR3 mutations (dotted line: mutated FGFR3, solid line: non-mutated FGFR3; log rank test p=0.014):b) Kaplan-Meier disease-specific survival curves according to FGFR3 mutations (dotted line: mutated FGFR3, solid line: non-mutated FGFR3; log rank test p=0.007)

EXAMPLE 1

FGFR3 Gene Mutations in Bladder and Cervix Carcinomas

FGFR3-IIIb and FGFR3-IIIc transcript levels were examined by reverse transcription-polymerase chain reaction (RT-PCR) in 76 primary bladder carcinomas and 29 primary invasive cervical carcinomas.

FGFR3-IIIb, the sole isoform to be significantly expressed, was detected in 72 out of 76 (94%) bladder carcinomas and 27 out of 29 (93%) cervical carcinomas.

A PCR-SSCP analysis was then conducted on both reverse transcribed RNA and genomic DNA to screen for FGFR3 coding sequence variants in 26 bladder and 12 cervix cancers expressing the gene. The results are illustrated in FIGS. 1a and 1b which gives the identification of FGFR3 gene mutations in human carcinomas:

a: gives the identification of somatic mutations by direct sequencing of PCR products. Normal constitutional DNA; Tumour, tumour DNA.

b: gives FGFR3 mutations associated with squeletal disorders and cancers.

The schematic structure of FGFR3 is depicted (Ig I–III, immunoglobulin like domains; TM, transmembrane domain; TK-1 and -2, tyrosine kinase domains) and the locations of the known human missense mutations associated with thanatophoric dysplasia (TD) and severe achondroplasia (SADDAN), bladder and cervix carcinomas (carc.) and multiple myeloma (MM) are indicated. Usual amino acid abbreviations are used to point out the mutation found in each pathological situation. The mutations at codon 807 incriminated in TD replaces a Stop codon (J) by an amino acid (G, C, R or L) and the mRNA thus continues to be translated until another in-frame Stop codon is reached 423 nucleotides downstream thus leading to a 141 amino acid longer protein.

Abnormally migrating bands were observed for certain samples (FIG. 1a) and direct sequencing of PCR products revealed single nucleotide substitutions in 9 out 26 bladder carcinomas (35%) and 3 out of 12 (25%) cervix carcinomas (FIG. 1b and table 1).

TABLE 1

Summary of FGFR3 gene mutations in primary bladder and cervix cancers

| Sample | Histophathol. | Codon | Nt Position | Mutation | Predicted effect |
| --- | --- | --- | --- | --- | --- |
| 1447, bladder | carc., Ta G2 | 249 | 746 | TCC to TGC | Ser to Cys |
| 342, bladder | carc., T1a G1 | 249 | 746 | TCC to TGC | Ser to Cys |
| 813, bladder | carc.. T1a G1 | 372 | 1114 | GGC to TGC | Gly to Cys |
| 1393.1, bladder | carc., T1a G3 | 249 | 746 | TCC to TGC | Ser to Cys |
| 506, bladder | carc., T1b G2 | 372 | 1114 | GGC to TGC | Gly to Cys |
| 1084. bladder | carc., T1b G3 | 652 | 1954 | AAG to GAG | Lys to Glu |
| 745.1, bladder | carc., T2 G3 | 248 | 742 | CGC to TGC | Arg to Cys |
| 1077, bladder | carc., T3 G2 | 249 | 746 | TCC to TGC | Ser to Cys |
| 1210, bladder | carc., T3 G2 | 249 | 746 | TCC to TGC | Ser to Cys |
| 4.13, cervix | carc., stage II | 249 | 746 | TCC to TGC | Ser to Cys |
| 4.139, cervix | carc., stage II | 249 | 746 | TCC to TGC | Ser to Cys |
| 6.96.1, cervix | carc., stage II | 249 | 746 | TCC to TGC | Ser to Cys |

Histopathol., histopathological classification of the tumours (carc., carcinoma: TNM and HUGO classifications are used respectively for bladder and cervix cancers); codon and mutated nucleotide (Nt position) are numbered according to FGFR3-IIIb cDNA open reading frame.

Mutations were found in the following exons exon 7, encoding the junction between immunoglobulin-like domains II and III of FGFR3 (one C-to-T transition at codon 248 in patient 745.1 and a C-to-G substitution at codon 249 in patient 1447);

exon 10, encoding the transmembrane domain (a G-to-T transversion at codon 372 in patient 813)

exon 15, encoding the tyrosine kinase domain II (a A-to-G transition at codon 652 in patient 1084).

Analysis of matched constitutional DNA from the patients for which such material was available (n=8) demonstrated the somatic nature of these FGFR3 mutations (FIG. 1).

Strikingly, each of the FGFR3 missense mutations identified herein, i.e. R248C, S249C, G372C and K652E, are implicated in thanatophoric dysplasia (TD). Given the presence of two additional amino-acids in the IIIb isoform expressed in epithelial cancers as compared to the IIIc isoform expressed in bone, the G372C and K652E mutations are indeed equivalent to the G370C and K650E mutations responsible for TD.

The S249C mutation was the most commonly observed, affecting 5 out of 9 (55%) bladder cancers and all of the cervical cancers (3 out of 3, 100%) in which FGFR3 gene alterations have been identified so far.

The R248C, S249C and G372/370C mutations create cysteine residues in the extracellular or transmembrane domains of the receptor and the K652/650E mutations results in amino-acid substitution in the kinase domain of the receptor.

EXAMPLE 2

Inhibitors

A way to test the different FGFR3 inhibitors comprises transfecting cell lines so that they express the mutated forms of FGFR3, or wild type FGFR3 or just the neomycin or hygromycin resistant gene under the control of a strong promoter, such as CMV, RSV, SV40 promoters. The tumorigenic properties of these cell lines can then be compared in vitro or in vivo in nude mice. The different inhibitors will be tested in vitro or in vivo using these different cell lines. Phosphorylation, proliferation or indirect effects of FGFR3 such as calcium influx will be measured. Transgenic mice expressing in various epithelia the mutated FGFR3 can thus be derived thereof. Those mice developing tumours are useful tools for testing the efficiency of candidate inhibiting drugs. Such transgenic animals fall also into the scope of the present invention.

EXAMPLE 3

FGFR3 Mutations in Ta. T1 Tumours in Bladder Cancer

Bladder cancer is a disease with a spectrum of forms and is highly unpredictable. At the time of initial diagnosis, approximately 80% of patients present with a superficial tumour. Superficial bladder cancers include carcinoma in situ (Tis), Ta and T1 lesions (TNM classification). Ta/T1 lesions are mostly papillary urothelial carcinomas: Ta lesions do not invade the basement membrane, whereas T1 lesions invade the lamina propria, but do not invade the detrusor muscle of the bladder wall. Carcinoma in situ are flat, cytologically high-grade carcinomas, confined to the urothelium. Primary isolated carcinoma in situ is a very rare entity and is more commonly associated with Ta/T1 lesions. Despite transurethral resection alone or combined with adjuvant intravesical therapies, more than one half of patients with Ta/T1 tumours suffer recurrences. In most cases, recurrences are also superficial, but about 5% of Ta and 30–50% of T1 tumours progress in an unpredictable manner to muscle invasion with a high risk of development of metastases and death from bladder cancer.

The management of superficial bladder cancer is based on clinicopathological parameters. Three groups of tumours can be defined, of low, intermediate and high risk, according to their potential for recurrence and progression. This classification is used to recommend adjuvant intravesical therapies and bladder monitoring, but it is not a sufficiently sensitive discriminant for use in determining the appropriate treatment and mode of surveillance for a given patient. Although Bacille Calmette-Guérin (BCG) therapy appeared to be the most effective regimen for the high-risk group, long-term results indicate that progression occurs in 40% by 10 years and in more than 50% by 15 years. For some researchers, these findings justified the use of up-front radical cystectomy in high-risk superficial urothelial carcinomas, despite the risk of overtreating a significant number of patients. Follow-up of Ta and T1 superficial bladder cancers constitutes most of the workload of urologists involved in the management of bladder cancer. The current strategy is based on frequent cystoscopic evaluations using a schedule that is largely empirical, without considering the individual characteristics of the tumour.

The limitations of the current management of bladder cancer demonstrate the need for prognostic markers, making possible the use of selective aggressive treatments for patients at high risk of progression while sparing low-risk patients from unnecessary procedures. A number of chromosomal loci and specific genes have been implicated in bladder tumorigenesis. Losses of all or part of chromosome 9 in many TaG1 tumours suggests that the inactivation of a gene or genes on chromosome 9 may be an early event in urothelial transformation. The prognostic significance of losses on chromosome 9 is unclear. Alterations of the P53 and RB genes controlling the G1 cell cycle checkpoint have been clearly delineated and are associated with the aggressiveness of superficial and invasive bladder cancers. Despite these recent insights into the molecular mechanisms of bladder carcinoma progression, these markers have not yet had any impact on clinical practice.

The following assays have been performed to assess the reliability, as markers, of the FGFR3 mutations.

Material and Method

Patients and Tissue Samples

Seventy four specimens of superficial Ta, T1 bladder carcinomas were obtained from 74 patients by transurethral resection performed at the Henri Mondor hospital, Créteil, France, from January 1988 to December 1998. Tumours were staged according to the TNM classification (1) and graded according to criteria recommended by the World Health Organisation (2). This series consisted of 25 pTa and 49 pT1 tumours, with 28 grade G1, 33 grade G2 and 13 grade G3 tumours. The 64 men and 10 women had a mean age of 64 years (range: 29 to 94 years). None of the patients had any detectable distant metastases at the time of transurethral resection. Patients were treated by transurethral resection (TUR) alone (n=25). TUR followed by mitomycin C instillation (n=10) or TUR and BCG (n=39) according to the French Committee for Urologic Oncology (CCAFU) recommendations. There was no change in the policy for treating superficial bladder cancer during the study period. Progression was defined as the occurrence of a pT2 or higher stage or appearance of lymph node invasion or metastasis or death from cancer. Disease-specific survival curves were plotted using death from urothelial cancer as the endpoint. Follow-up was based on systematic cystoscopy and cytology, and imaging studies only when indicated. All outpatient visits and hospital admissions were recorded in a database from which the study data were calculated.

Tumour DNA was extracted from formalin-fixed and paraffin-embedded tissue or samples freshly frozen in liquid nitrogen (4). Normal DNA samples from peripheral blood were available for 27 patients.

FGFR3 Mutation Analysis

Mutations in the FGFR3 gene were detected by SSCP analysis. Exons 7, 10, 15 and 20 of the FGFR3 gene were analysed because these exons harbour all the mutations previously identified in bladder carcinomas and thanatophoric dysplasia. All mutations detected by SSCP analysis were confirmed by direct bidirectional sequencing of tumour genomic DNA. Matched normal DNA, if available, was sequenced on both strands to demonstrate the somatic nature of these mutations.

Statistical Methods

Associations between FGFR3 mutation status and other data (sex, age, stage and grade) were tested using $x^2$ and Student's t tests. Progression-free and disease-specific survival curves were plotted using Kaplan-Meier estimates. Survival distributions were compared using the log-rank test. Cox's proportional hazards regression model was used to test the effect of mutations, while simultaneously accounting for baseline patient and tumour characteristics. The influence of the covariates on the FGFR3 mutation effect was assessed in multivariate analysis involving a forward stepwise procedure and a backward stepwise procedure, using the MPRL (maximum partial likelihood ratio) method. The limit to enter a term was 0.15 and the limit to remove a term was 0.10. Statistical analyses were performed using BMDP® and S-Plus® software.

Results

FGFR3 missense mutations were observed in 41 of the 74 (55%) Ta. T1 bladder tumours. The FGFR3 mutations found are described in Table 2 below:

TABLE 2

| Number of tumours (%) | Codon* | nt position* | Mutation | Predicted effect |
|---|---|---|---|---|
| 5 (12%) | 248 | 742 | CGC -> TGC | Arg -> Cys |
| 28 (68.5%) | 249 | 746 | TCC -> TGC | Ser -> Cys |
| 5 (12%) | 372 | 1,114 | GGC -> TGC | Gly -> Cys |
| 2 (5%) | 375 | 1,124 | TAT -> TGT | Tyr -> Cys |
| 1 (2.5%) | 652 | 1,954 | AAG -> GAG | Lys -> Glu |

*codon and mutated nucleotide (nt position) are numbered according to FGFR3-IIIb cDNA open reading frame. FGFR3-IIIb is the isoform expressed in epithelial cells.

S249C was the commonest mutation and was found in 16 of the 21 (76%) mutated Ta tumours and 12 of the 20 (60%) mutated T1 tumours. Matched constitutional DNA, available in 15 of the cases of tumour with mutations, contained wild-type sequences, demonstrating the somatic nature of these mutations.

The correlation between sex, age, stage, grade and FGFR3 mutation status is given Table 3:

TABLE 3

| | FGFR3 wild type | FGFR3 mutant | p value ($Z^3$ or Student's t test) |
|---|---|---|---|
| Sex | | | |
| Male | 29 | 35 | 0.9779 |
| Female | 4 | 6 | |
| Age (years) | | | |
| mean | 64.30 | 63.22 | 0.7393 |
| range | [29.15–86.10] | [34.3–94.4] | |
| Stage | | | |
| Ta | 4 | 21 | 0.001 |
| T1 | 29 | 20 | |
| Grade | | | |
| G1 | 7 | 21 | 0.0003 |
| G2 | 14 | 19 | |
| G3 | 12 | 1 | |

Statistically significant correlations were observed between FGFR3 mutations and low stage (p=0.001) and low grade (p=0.0003), but not between these mutations and age or sex (Table 2).

With a median follow-up of 4.3 years (range: 6 months to 11 years), 3 patients progressed and one died in the mutated tumour group (n=41 patients) whereas ten patients progressed and eight died in the non-mutated tumour group (n=33 patients). The median follow-up was 5.6 years (range:

7 months to 11 years) in the non-mutated group and 4.1 years (range: 6 months to 9 years) in the mutated group.

To examine FGFR3 mutations as a marker of patient outcome, we calculated Kaplan-Meier progression-free survival and disease-specific survival probability curves for the two groups of patients and examined the differences using the log rank test. Progression-free and disease-specific survival indicated that FGFR3 mutations were associated with a lower risk of progression (p=0.014) and longer survival (p=0.007) (FIG. 3). We tested several variables (age, sex, stage, grade) but only stage was significantly associated with progression and survival in univariate analysis. If only Tl patients were analysed, the correlation was still significant for disease-specific survival (p=0.03) and close to significance for progression-free survival (p=0.052).

Multivariate analysis was used to determine whether the correlation between FGFR3 mutation status and progression-free survival or disease-specific survival was independent of other outcome predictors. For progression-free survival, the following covariates were introduced into the Cox model: mutation, stage, grade and sex. For disease-specific survival, mutation and grade were the only covariates introduced into the model, as no disease-related deaths were observed among female or Ta patients. If FGFR3 status was entered into the model, neither stage nor grade provided any additional prognostic value for tumour progression. In the analysis of disease-specific survival, FGFR3 mutation was also the only covariate to be entered into the model, as grade did not provide any additional prognostic information. Relative risks and their 95% confidence intervals (CI) are shown in Table 4.

TABLE 4

| FGFR3 | Progression | | Disease-specific Survival | |
|---|---|---|---|---|
| | Relative Risk | 95% CI | Relative Risk | 95% CI |
| Wild-type | 1 | | 1 | |
| Mutant | 0.23 | (0.06; 0.83) | 0.10 | (0.01; 0.80) |

Other variables do not significantly contribute to the model

Forward and backward procedures both yielded the same model. As shown by the above results, the FGFR3 activating mutations were frequent in bladder carcinomas.

All the carcinomas having a mutated receptor expressed said receptor at levels similar or above those observed with normal tissues. Immunohistochemical methods will then advantageously be used for revealing the receptor.

FGFR3 mutation detection in bladder carcinomas appears to be a good prognostic, giving then to the clinicians valuable means for treating and observing carcinomas, which represent a medical problem due to the high frequency of recurrences.

By using SSCP or PCR coupled to an enzymatic restriction S249C mutation specific (which represent 75% of the mutations) on patients having bladder carcinomas with S249C mutation, the mutation could be detected in urine in 60% of the cases.

EXAMPLE 4

Detection of FGFR3 Mutations in Patients' Urines

Genomic DNA is extracted from patients' urines and amplified by PCR, in the presence of $^{32}$P-labelled dCTP, using standard methods. The following primers were used for detecting S249C mutation:

5'-CAG CAC CGC CGT CTG GTT GG-3' (SEQ ID NO:25) and 5'-AGT GGC GGT GGT GGT GAG GGA G-3' (SEQ ID NO:26).

30 cycles of PCR are performed.

The amplification products are digested by Cac8I. An additional site is created by FGFR3 mutation and a corresponding band is observed on an electrophoretic gel.

Similarly the following primers and enzymes can be used to detect:

R248C Mutation:

Primers: 5'-TGT GCG TCA CTG TAC ACC TTG CAG-3' (SEQ ID NO:27) and 5'-AGT GGC GGT GGT GGT GAG GGA G-3' (SEQ ID NO:28)

Enzyme: Bsi HKA I

K652E Mutation:

Primers: 5'-TGG TGA CCG AGG ACA ACG TGA TG-3' (SEQ ID NO:29) and 5'-AGG GTG TGG GAA GGC GGT GTT G-3' (SEQ ID NO:30)

Enzyme: Bsm A I

G372C Mutation:

Primers: 5'-CCT CAA CGC CCA TGT CTT TTC AGC-3' (SEQ ID NO:31) and 5'-CTT GAG CGG GAA GCG GGA GAT CTT G-3' (SEQ ID NO:32)

Enzyme: Pst I

Y375C Mutation:

Primers: 5'-CCT CAA CGC CCA TGT CTT TTC AGC-3' (SEQ ID NO:33) and 5'-CTT GAG CGG GAA GCG GGA GAT CTT G-3' (SEQ ID NO:34)

Enzyme: Bsg I

REFERENCES

1. Sobin L H, Fleming I D. TNM Classification of Malignant Tumors, fifth edition (1997). Union Internationale Contre le Cancer and the American Joint Committee on Cancer. *Cancer* 1997; 80: 1803–4.
2. Epstein J I, Amin M B, Reuter V R, Mostofi F K. The World Health Organization/International Society of Urological Pathology consensus classification of urothelial (transitional cell) neoplasms of the urinary bladder. Bladder Consensus Conference Committee. *Am J Surg Pathol* 1998; 22: 1435–48.
3. Rischmann P, Bittard H, Chopin D, et al. Tumeurs Urothéliales. *Prog Urol* 1998; 8: 25–50.
4. Cappellen D, Gil Diez de Media S, Chopin D, Thiery J P, Radvanyi F. Frequent loss of heterozygosity on chromosome 10q in muscle-invasive transitional cell carcinomas of the bladder. *Oncogene* 1997; 14: 3059–66.
5. Cappellen D, De Oliveira C, Ricol D, Gil Diez de Media S, Bourdin J, Sastre-Garau X, Chopin D, Thiery J P, Radvanyi F. Frequent activating mutations of FGFR3 in human bladder and cervix carcinomas. *Nature Genetics*, vol 23, September 1999.
6. Gossen M, Freundlieb S, Bender G, Muller G, Hillen W, Bujard H. Transcriptional activation by tetracyclines in mammalian cells. *Science* 1995; 268: 1766–9.

The invention claimed is:

1. A method for determining the presence of a carcinoma of the bladder or cervix in a biological sample containing cells of the bladder or cells of the cervix or cellular components thereof, said method comprising measuring for the presence of a carcinoma-associated FGFR3 mutation in said sample, the presence of said mutation indicating the presence of said carcinoma.

2. The method of claim 1, wherein said measuring comprises screening for at least one nucleotide FGFR3 mutation in at least one nucleic acid selected from the group consisting of genomic DNA, RNA and cDNA.

3. The method of claim 1, wherein said measuring comprises screening for at least one FGFR3 protein mutation.

4. The method of claim 1, wherein said measuring comprises screening for at least one FGFR3 mutation which creates cysteine residues in the extracellular or transmembrane domains of the FGFR3 receptor.

5. The method of claim 1, wherein said measuring comprises screening for at least one mutation resulting in at least one amino-acid substitution in the kinase domain of the FGFR3 receptor.

6. The method of claim 5, wherein said screening further comprises screening for an activating mutation of FGFR3.

7. The method of claim 1, wherein said measuring further comprises screening for at least one mutation in the group comprising exon 7, encoding the junction between immunoglobulin-like domains II and III of FGFR3, exon 10, encoding the transmembrane domain, exon 15, encoding the tyrosine kinase domain I, and the exon encoding the C-terminal part.

8. The method of claim 1, wherein said measuring further comprises screening for missense mutations.

9. The method of claim 1, wherein said mutation is selected from the group consisting of R248C, S249C, G372C, K652E and Y375C.

10. The method of claim 1, wherein the biological sample is selected in the group comprising a tissue, or a body fluid.

11. The method of claim 10, wherein said body fluid is selected in the group comprising blood, urine from a warm-blooded animal.

12. The method of claim 1, wherein said biological sample comprises human bladder cells or human cervical cells.

13. The method of claim 1, wherein said mutation is selected from the group consisting of S249C, G372C and K652E.

14. The method of claim 1, wherein said mutation is selected from the group consisting of R248C, S249C, G372C, G382R, A393E, K652E, K652M, S373C and Y375C.

15. A method for determining the presence of a carcinoma of the bladder or cervix in a biological sample containing cells of the bladder or cells of the cervix or cellular components thereof, said method comprising measuring for the presence of a carcinoma-associated FGFR3-IIIb mutation in said sample, the presence of said mutation indicating the presence of said carcinoma.

16. The method of claim 1, wherein said mutation is selected from the group consisting of S249C, G372C and R248C.

17. The method of claim 15, wherein said measuring further comprises screening for at least one mutation from a region selected from the group consisting of exon 7, exon 10, exon 15, and the exon encoding the C-terminal part of FGFR3-IIIb.

* * * * *

SEQUENCE LISTING

<160> NUMBER OF SEQ ID NOS: 34

<210> SEQ ID NO 1
<211> LENGTH: 2427
<212> TYPE: DNA
<213> ORGANISM: Artificial Sequence
<220> FEATURE:
<223> OTHER INFORMATION: Description of Artificial Sequence:Wild Type
      FGFR3-IIIb:

<400> SEQUENCE: 1

```
atgggcgccc ctgcctgcgc cctcgcgctc tgcgtggccg tggccatcgt ggccggcgcc      60
tcctcggagt ccttggggac ggagcagcgc gtcgtggggc gagcggcaga agtcccgggc     120
ccagagcccg ccagcaggga gcagttggtc ttcggcagcg gggatgctgt ggagctgagc     180
tgtcccccgc cgggggtgg tcccatgggg cccactgtct gggtcaagga tggcacaggg     240
ctggtgccct cggagcgtgt cctggtgggg ccccagcggc tgcaggtgct gaatgcctcc     300
cacgaggact ccgggcccta cagctgccgg cagcggctca gcagcgcgt actgtgccac     360 ttcagtgtgc gggtgacaga cgctccatcc tcgggagatg acgaagacgg ggaggacgag     420
gctgaggaca caggtgtgga cacagggccc cttactgga cacggcccga gcggatggac     480
aagaagctgc tggccgtgcc ggccgccaac accgtccgct tccgctgccc agccgctggc     540
aaccccactc cctccatctc ctggctgaag aacggcaggg agttccgcgg cgagcaccgc     600
attggaggca tcaagctgcg gcatcagcag tggagcctgg tcatggaaag cgtggtgccc     660
tcggaccgcg gcaactacac ctgcgtcgtg gagaacaagt ttggcagcat ccggcagacg     720
tacacgctgg acgtgctgga gcgctccccg caccggccca tcctgcaggc ggggctgccg     780
gccaaccaga cggcggtgct gggcagcgac gtggagttcc actgcaaggt gtacagtgac     840
gcacagcccc acatccagtg gctcaagcac gtggaggtga acggcagcaa ggtgggcccg     900
gacggcacac cctacgttac cgtgctcaag tcctggatca gtgagagtgt ggaggccgac     960
gtgcgcctcc gcctggccaa tgtgtcgagc gggacggggc gcgagtacct ctgtcgagcc    1020
accaatttca taggcgtggc cgagaaggcc ttttggctga cgttcacgg ccccgagca     1080 gccgaggagg agctggtgga ggctgacgag gcgggcagtg tgtatgcagg catcctcagc    1140 tacgggtgg gcttcttcct gttcatcctg gtggtggcgg ctgtgacgct ctgccgcctg    1200
cgcagccccc ccaagaaagg cctgggctcc ccaccgtgc acaagatctc ccgcttcccg    1260
ctcaagcgac aggtgtccct ggagtccaac gcgtccatga gctccaacac accactggtg    1320
cgcatcgcaa ggctgtcctc aggggagggc cccacgctgg ccaatgtctc cgagctcgag    1380
ctgcctgccg accccaaatg ggagctgtct cgggcccggc tgaccctggg caagcccctt    1440
ggggagggct gcttcggcca ggtggtcatg gcggaggcca tcggcattga caaggaccgg    1500
gccgccaagc ctgtcaccgt agccgtgaag atgctgaaag acgatgccac tgacaaggac    1560
ctgtcggacc tggtgtctga gatggagatg atgaagatga tcgggaaaca caaaaacatc    1620
atcaacctgc tgggcgcctg cacgcagggc gggcccctgt acgtgctggt ggagtacgcg    1680
gccaagggta acctgcggga gtttctgcgg gcgcggcggc cccgggcct ggactactcc    1740 ttcgacacct gcaagccgcc cgaggagcag ctcacctca aggacctggt gtcctgtgcc    1800
taccaggtgg cccgggcat ggagtacttg gcctcccaga gtgcatcca gggacctg    1860 gctgcccgca atgtgctggt gaccgaggac aacgtgatga agatcgcaga cttcgggctg    1920
```

-continued

```
gcccgggacg tgcacaacct cgactactac aagaagacaa ccaacggccg gctgcccgtg    1980
aagtggatgg cgcctgaggc cttgtttgac cgagtctaca ctcaccagag tgacgtctgg    2040
tcctttgggg tcctgctctg ggagatcttc acgctggggg gctccccgta ccccggcatc    2100
cctgtggagg agctcttcaa gctgctgaag gagggccacc gcatggacaa gcccgccaac    2160
tgcacacacg acctgtacat gatcatgcgg gagtgctggc atgccgcgcc ctcccagagg    2220
cccaccttca gcagctggt ggaggacctg gaccgtgtcc ttaccgtgac gtccaccgac    2280
gagtacctgg acctgtcggc gcctttcgag cagtactccc cgggtggcca ggacaccccc    2340
agctccagct cctcagggga cgactccgtg tttgcccacg acctgctgcc cccggcccca    2400
cccagcagtg ggggctcgcg gacgtga                                         2427
```

<210> SEQ ID NO 2
<211> LENGTH: 2427
<212> TYPE: DNA
<213> ORGANISM: Artificial Sequence
<220> FEATURE:
<223> OTHER INFORMATION: Description of Artificial Sequence:Mutant R248C FGFR3-IIIb:

<400> SEQUENCE: 2

```
atgggcgccc ctgcctgcgc cctcgcgctc tgcgtggccg tggccatcgt ggccggcgcc     60
tcctcggagt ccttggggac ggagcagcgc gtcgtggggc gagcggcaga agtcccgggc    120
ccagagcccg ccagcaggga gcagttggtc ttcggcagcg gggatgctgt ggagctgagc    180 tgtccccgc ccggggtgg tcccatgggg cccactgtct gggtcaagga tgcacaggg    240 ctggtgccct cggagcgtgt cctggtgggg ccccagcggc tgcaggtgct gaatgcctcc    300
cacgaggact ccggggccta cagctgccgg cagcggctca cgcagcgcgt actgtgccac    360
ttcagtgtgc gggtgacaga cgctccatcc tcgggagatg acgaagacgg ggaggacgag    420
gctgaggaca caggtgtgga cacaggggcc ccttactgga cacggcccga gcggatggac    480
aagaagctgc tggccgtgcc ggccgccaac accgtcgcct tccgctgccc agccgctggc    540
aaccccactc cctccatctc ctggctgaag aacggcaggg agttccgcgg cgagcaccgc    600
attggaggca tcaagctgcg gcatcagcag tggagcctgg tcatggaaag cgtggtgccc    660
tcggaccgcg gcaactacac ctgcgtcgtg gagaacaagt ttggcagcat ccggcagacg    720
tacacgctgg acgtgctgga gtgctccccg caccggccca tcctgcaggc ggggctgccg    780
gccaaccaga cggcggtgct gggcagcgac gtggagttcc actgcaaggt gtacagtgac    840
gcacagcccc acatccagtg gctcaagcac gtggaggtga acggcagcaa ggtgggcccg    900
gacggcacac cctacgttac cgtgctcaag tcctggatca gtgagagtgt ggaggccgac    960
gtgcgcctcc gcctggccaa tgtgtcggag cgggacgggg gcgagtacct ctgtcgagcc    1020
accaatttca taggcgtggc cgagaaggcc ttttggctga cgttcacgg gccccgagca    1080 gccgaggagg agctggtgga ggctgacgag gcgggcagtg tgtatgcagg catcctcagc    1140
tacgggtggg gcttcttcct gttcatcctg gtgtggcgg ctgtgacgct ctgccgcctg    1200
cgcagccccc ccaagaaagg cctgggctcc ccaccgtgc acaagatctc ccgcttcccg    1260
ctcaagcgac aggtgtccct ggagtccaac gcgtccatga gctccaacac caccgtggtg    1320
cgcatcgcaa ggctgtcctc aggggagggc cccacgctgg ccaatgtctc cgagctcgag    1380
ctgcctgccg accccaaatg ggagctgtct cgggcccggc tgaccctggg caagccccct    1440
ggggagggct gcttcggcca ggtggtcatg gcggaggcca tcggcattga caaggaccgg    1500
```

-continued

```
gccgccaagc ctgtcaccgt agccgtgaag atgctgaaag acgatgccac tgacaaggac    1560
ctgtcggacc tggtgtctga gatggagatg atgaagatga tcgggaaaca caaaaacatc    1620
atcaacctgc tgggcgcctg cacgcagggc gggcccctgt acgtgctggt ggagtacgcg    1680
gccaagggta acctgcggga gtttctgcgg gcgcggcggc ccccgggcct ggactactcc    1740
ttcgacacct gcaagccgcc cgaggagcag ctcaccttca aggacctggt gtcctgtgcc    1800
taccaggtgg cccggggcat ggagtacttg gcctcccaga agtgcatcca cagggacctg    1860
gctgcccgca atgtgctggt gaccgaggac aacgtgatga gatcgcaga cttcgggctg    1920 gcccgggacg tgcacaacct cgactactac aagaagacaa ccaacggccg gctgcccgtg    1980
aagtggatgg cgcctgaggc cttgtttgac cgagtctaca ctcaccagag tgacgtctgg    2040
tcctttgggg tcctgctctg ggagatcttc acgctggggg ctccccgta ccccggcatc    2100 cctgtggagg agctcttcaa gctgctgaag gagggccacc gcatggacaa gcccgccaac    2160
tgcacacacg acctgtacat gatcatgcgc gagtgctggc atgccgcgcc ctcccagagg    2220
cccaccttca gcagctggt ggaggacctg gaccgtgtcc ttaccgtgac gtccaccgac    2280
gagtacctgg acctgtcggc gccttcgag cagtactccc cggtggcca ggacaccccc    2340 agctccagct cctcagggga cgactccgtg tttgcccacg acctgctgcc cccggcccca    2400
cccagcagtg ggggctcgcg gacgtga                                       2427
```

<210> SEQ ID NO 3
<211> LENGTH: 2427
<212> TYPE: DNA
<213> ORGANISM: Artificial Sequence
<220> FEATURE:
<223> OTHER INFORMATION: Description of Artificial Sequence:Mutant S249C
FGFR3-IIIb:

<400> SEQUENCE: 3

```
atgggcgccc ctgcctgcgc cctcgcgctc tgcgtggccg tggccatcgt ggccggcgcc     60
tcctcggagt ccttggggac ggagcagcgc gtcgtgggc gagcggcaga agtcccgggc    120
ccagagcccg gccagcagga gcagttggtc ttcggcagcg gggatgctgt ggagctgagc    180
tgtcccccgc ccgggggtgg tcccatgggg cccactgtct gggtcaagga tggcacaggg    240
ctggtgccct cggagcgtgt cctggtgggg ccccagcggc tgcaggtgct gaatgcctcc    300
cacgaggact ccgggggccta cagctgccgg cagcggctca cgcagcgcgt actgtgccac    360
ttcagtgtgc gggtgacaga cgctccatcc tcgggagatg acgaagacgg ggaggacgag    420
gctgaggaca caggtgtgga cacaggggcc ccttactgga cacggcccga gcggatggac    480
aagaagctgc tggccgtgcc ggccgccaac accgtccgct ccgctgccc agccgctggc    540 aaccccactc cctccatctc ctggctgaag aacggcaggg agttccgcgg cgagcaccgc    600
attggaggca tcaagctgcg gcatcagcag tggagcctgg tcatggaaag cgtggtgccc    660
tcggaccgcg gcaactacac ctgcgtcgtg gagaacaagt ttggcagcat ccggcagacg    720
tacacgctgg acgtgctgga gcgctgcccg caccggccca tcctgcaggc ggggctgccg    780
gccaaccaga cggcggtgct gggcagcgac gtggagttcc actgcaaggt gtacagtgac    840
gcacagcccc acatccagtg gctcaagcac gtggaggtga acggcagcaa ggtgggcccg    900
gacggcacac cctacgttac cgtgctcaag tcctggatca gtgagagtgt ggaggccgac    960
gtgcgcctcc gcctgccaa tgtgtcggag cgggacgggg cgagtacct ctgtcgagcc    1020 accaatttca taggcgtggc cgagaaggcc ttttggctga cgttcacgg gccccgagca    1080
```

```
gccgaggagg agctggtgga ggctgacgag gcgggcagtg tgtatgcagg catcctcagc   1140 tacgggtgg gcttcttcct gttcatcctg gtggtggcgg ctgtgacgct ctgccgcctg    1200 cgcagcccc ccaagaaagg cctgggctcc ccaccgtgc acaagatctc ccgcttcccg     1260
ctcaagcgac aggtgtccct ggagtccaac gcgtccatga gctccaacac accactggtg   1320
cgcatcgcaa ggctgtcctc aggggagggc cccacgctgg ccaatgtctc cgagctcgag   1380
ctgcctgccg accccaaatg ggagctgtct cgggcccggc tgaccctggg caagccccttt 1440 ggggagggct gcttcggcca ggtggtcatg gcggaggcca tcggcattga caaggaccgg   1500
gccgccaagc ctgtcaccgt agccgtgaag atgctgaaag acgatgccac tgacaaggac   1560
ctgtcggacc tggtgtctga gatggagatg atgaagatga tcgggaaaca caaaaacatc   1620
atcaacctgc tgggcgcctg cacgcagggc gggcccctgt acgtgctggt ggagtacgcg   1680
gccaagggta acctgcggga gtttctgcgg gcgcggcggc ccccgggcct ggactactcc   1740
ttcgacacct gcaagccgcc cgaggagcag ctcaccttca aggacctggt gtcctgtgcc   1800
taccaggtgg cccggggcat ggagtacttg gcctcccaga gtgcatcca cagggacctg   1860 gctgcccgca atgtgctggt gaccgaggac aacgtgatga gatcgcaga cttcgggctg   1920 gcccgggacg tgcacaacct cgactactac aagaagacaa ccaacggccg gctgccgtg   1980 aagtggatgg cgcctgaggc cttgtttgac cgagtctaca ctcaccagag tgacgtctgg   2040
tccttggggg tcctgctctg ggagatcttc acgctggggg ctccccgta ccccggcatc   2100 cctgtggagg agctcttcaa gctgctgaag gagggccacc gcatggacaa gcccgccaac   2160
tgcacacacg acctgtacat gatcatgcgg gagtgctggc atgccgcgcc ctcccagagg   2220
cccaccttca gcagctggt ggaggacctg gaccgtgtcc ttaccgtgac gtccaccgac   2280
gagtacctgg acctgtcggc gcctttcgag cagtactccc cgggtggcca ggacaccccc   2340
agctccagct cctcagggga cgactccgtg tttgcccacg acctgctgcc cccggccca   2400 cccagcagtg ggggctcgcg gacgtga                                       2427

<210> SEQ ID NO 4
<211> LENGTH: 2427
<212> TYPE: DNA
<213> ORGANISM: Artificial Sequence
<220> FEATURE:
<223> OTHER INFORMATION: Description of Artificial Sequence:Mutant G372C
      FGFR3-IIIb:

<400> SEQUENCE: 4
atgggcgccc ctgcctgcgc cctcgcgctc tgcgtggccg tggccatcgt ggccggcgcc   60
tcctcggagt ccttggggac ggagcagcgc gtcgtggggc gagcggcaga agtcccgggc   120
ccagagcccg gccagcagga gcagttggtc ttcggcagcg gggatgctgt ggagctgagc   180
tgtcccccgc ccggggtgg tcccatgggg cccactgtct gggtcaagga tggcacaggg   240
ctggtgccct cggagcgtgt cctggtgggg ccccagcggc tgcaggtgct gaatgcctcc   300
cacgaggact ccggggccta cagctgccgg cagcggctca cgcagcgcgt actgtgccac   360
ttcagtgtgc gggtgacaga cgctccatcc tcgggagatg acgaagacgg ggaggacgag   420
gctgaggaca caggtgtgga cacagggggcc ccttactgga cacggcccga gcggatggac   480
aagaagctgc tggccgtgcc ggccgccaac accgtccgct tccgctgccc agccgctggc   540
aaccccactc cctccatctc ctggctgaag aacggcaggg agttccgcgg cgagcaccgc   600
attggaggca tcaagctgcg gcatcagcag tggagcctgg tcatggaaag cgtggtgccc   660
```

-continued

```
tcggaccgcg gcaactacac ctgcgtcgtg gagaacaagt ttggcagcat ccggcagacg    720
tacacgctgg acgtgctgga gcgctccccg caccggccca tcctgcaggc ggggctgccg    780
gccaaccaga cggcggtgct ggcagcgac gtggagttcc actgcaaggt gtacagtgac    840
gcacagcccc acatccagtg gctcaagcac gtggaggtga acggcagcaa ggtgggcccg    900
gacggcacac cctacgttac cgtgctcaag tcctggatca gtgagagtgt ggaggccgac    960
gtgcgcctcc gcctggccaa tgtgtcggag cgggacgggg gcgagtacct ctgtcgagcc   1020
accaatttca taggcgtggc cgagaaggcc ttttggctga cgttcacgg ccccgagca    1080 gccgaggagg agctggtgga ggctgacgag gcgtgcagtg tgtatgcagg catcctcagc   1140
tacggggtgg gcttcttcct gttcatcctg gtggtggcgg ctgtgacgct ctgccgcctg   1200
cgcagccccc ccaagaaagg cctgggctcc cccaccgtgc acaagatctc ccgcttcccg   1260
ctcaagcgac aggtgtccct ggagtccaac gcgtccatga gctccaacac accactggtg   1320
cgcatcgcaa ggctgtcctc aggggaggc cccacgctgg ccaatgtctc cgagctcgag   1380
ctgcctgccg accccaaatg ggagctgtct cgggcccggc tgaccctggg caagcccctt   1440
ggggagggct gcttcggcca ggtggtcatg gcggaggcca tcggcattga caaggaccgg   1500
gccgccaagc ctgtcaccgt agccgtgaag atgctgaaag acgatgccac tgacaaggac   1560
ctgtcggacc tggtgtctga gatggagatg atgaagatga tcgggaaaca caaaaacatc   1620
atcaacctgc tgggcgcctg cacgcagggc gggcccctgt acgtgctggt ggagtacgcg   1680
gccaagggta acctgcggga gtttctgcgg gcgcggcggc cccgggcct ggactactcc   1740 tcgacacct gcaagccgcc cgaggagcag ctcaccttca aggacctggt gtcctgtgcc   1800
taccaggtgg cccggggcat ggagtacttg gcctcccaga gtgcatcca cagggacctg   1860 gctgcccgca atgtgctggt gaccgaggac aacgtgatga agatcgcaga cttcgggctg   1920
gcccgggacg tgcacaacct cgactactac aagaagacaa ccaacggccg gctgcccgtg   1980
aagtggatgg cgcctgaggc cttgtttgac cgagtctaca ctcaccagag tgacgtctgg   2040
tcctttgggg tcctgctctg ggagatcttc acgctggggg gctccccgta ccccggcatc   2100
cctgtggagg agctcttcaa gctgctgaag gagggccacc gcatggacaa gcccgccaac   2160
tgcacacacg acctgtacat gatcatgcgg gagtgctggc atgccgcgcc ctcccagagg   2220
cccaccttca gcagctggt ggaggacctg gaccgtgtcc ttaccgtgac gtccaccgac   2280
gagtacctgg acctgtcggc gcctttcgag cagtactccc cgggtggcca ggacaccccc   2340
agctccagct cctcagggga cgactccgtg tttgcccacg acctgctgcc ccggccccca   2400
cccagcagtg ggggctcgcg gacgtga                                      2427
```

<210> SEQ ID NO 5
<211> LENGTH: 2427
<212> TYPE: DNA
<213> ORGANISM: Artificial Sequence
<220> FEATURE:
<223> OTHER INFORMATION: Description of Artificial Sequence:Mutant K652E
      FGFR3-IIIb:

<400> SEQUENCE: 5

```
atgggcgccc ctgcctgcgc cctcgcgctc tgcgtggccg tggccatcgt ggccggcgcc     60
tcctcggagt ccttggggac ggagcagcgc gtcgtgggg gagcggcaga agtcccgggc    120
ccagagcccg ccagcagga gcagttggtc ttcggcagcg gggatgctgt ggagctgagc    180
tgtcccccgc ccgggggtgg tcccatgggg cccactgtct gggtcaagga tggcacaggg    240
```

```
ctggtgccct cggagcgtgt cctggtgggg ccccagcggc tgcaggtgct gaatgcctcc    300
cacgaggact ccggggccta cagctgccgg cagcggctcc cgcagcgcgt actgtgccac    360
ttcagtgtgc gggtgacaga cgctccatcc tcgggagatg acgaagacgg ggaggacgag    420
gctgaggaca caggtgtgga cacaggggcc ccttactgga cacggcccga gcggatggac    480
aagaagctgc tggccgtgcc ggccgccaac accgtccgct tccgctgccc agccgctggc    540
aaccccactc cctccatctc ctggctgaag aacggcaggg agttccgcgg cgagcaccgc    600
attggaggca tcaagctgcg gcatcagcag tggagcctgg tcatggaaag cgtggtgccc    660
tcggaccgcg gcaactacac ctgcgtcgtg gagaacaagt tggcagcat ccggcagacg    720
tacacgctgg acgtgctgga gcgctccccg caccggccca tcctgcaggc ggggctgccg    780
gccaaccaga cggcggtgct gggcagcgac gtggagttcc actgcaaggt gtacagtgac    840
gcacagcccc acatccagtg gctcaagcac gtggaggtga acggcagcaa ggtgggcccg    900
gacggcacac cctacgttac cgtgctcaag tcctggatca gtgagagtgt ggaggccgac    960
gtgcgcctcc gcctggccaa tgtgtcggag cgggacgggg cgagtacct ctgtcgagcc   1020
accaatttca taggcgtggc cgagaaggcc ttttggctga cgttcacgg gccccgagca   1080
gccgaggagg agctggtgga ggctgacgag gcgggcagtg tgtatgcagg catcctcagc   1140
tacggggtgg gcttcttcct gttcatcctg gtggtggcgg ctgtgacgct ctgccgcctg   1200
cgcagccccc ccaagaaagg cctgggctcc cccaccgtgc acaagatctc ccgcttcccg   1260
ctcaagcgac aggtgtccct ggagtccaac gcgtccatga gctccaacac caccactggtg   1320
cgcatcgcaa ggctgtcctc aggggagggc cccacgctgg ccaatgtctc cgagctcgag   1380
ctgcctgccg accccaaatg ggagctgtct cgggcccggc tgaccctggg caagcccctt   1440
ggggagggct gcttcggcca ggtggtcatg gcggaggcca tcggcattga caaggaccgg   1500
gccgccaagc ctgtcaccgt agccgtgaag atgctgaaag acgatgccac tgacaaggac   1560
ctgtcggacc tggtgtctga gatggagatg atgaagatga tcgggaaaca caaaaacatc   1620
atcaacctgc tgggcgcctg cacgcagggc gggccctgt acgtgctggt ggagtacgcg   1680
gccaagggta acctgcggga gtttctgcgg gcgcggcggc cccgggcct ggactactcc   1740
ttcgacacct gcaagccgcc cgaggagcag ctcaccttca aggacctggt gtcctgtgcc   1800
taccaggtgg cccggggcat ggagtacttg gcctcccaga agtgcatcca cagggacctg   1860
gctgcccgca atgtgctggt gaccgaggac aacgtgatga agatcgcaga cttcgggctg   1920
gcccgggacg tgcacaacct cgactactac aaggagacaa ccaacggccg gctgcccgtg   1980
aagtggatgg cgcctgaggc cttgtttgac cgagtctaca ctcaccagag tgacgtctgg   2040
tcctttgggg tcctgctctg ggagatcttc acgctggggg ctccccgta ccccggcatc   2100
cctgtggagg agctcttcaa gctgctgaag gagggccacc gcatggacaa gcccgccaac   2160
tgcacacacg acctgtacat gatcatgcgg gagtgctggc atgccgcgcc ctcccagagg   2220
cccaccttca gcagctggt ggaggacctg gaccgtgtcc ttaccgtgac gtccaccgac   2280
gagtacctgg acctgtcggc gcctttcgag cagtactccc cggtggccaa ggacacccc   2340
agctccagct cctcagggga cgactccgtg tttgcccacg acctgctgcc cccggcccca   2400
cccagcagtg ggggctcgcg gacgtga                                      2427
```

<210> SEQ ID NO 6
<211> LENGTH: 2427
<212> TYPE: DNA
<213> ORGANISM: Artificial Sequence
<220> FEATURE:
<223> OTHER INFORMATION: Description of Artificial Sequence:Mutant S373C
      FGFR3-IIIb:

<400> SEQUENCE: 6

| | | | | | | |
|---|---|---|---|---|---|---|
| atgggcgccc | ctgcctgcgc | cctcgcgctc | tgcgtggccg | tggccatcgt | ggccggcgcc | 60 |
| tcctcggagt | ccttggggac | ggagcagcgc | gtcgtgggc | gagcggcaga | agtcccgggc | 120 |
| ccagagcccg | gccagcagga | gcagttggtc | ttcggcagcg | gggatgctgt | ggagctgagc | 180 |
| tgtccccgc | ccggggtgg | tcccatgggg | cccactgtct | gggtcaagga | tggcacaggg | 240 |
| ctggtgccct | cggagcgtgt | cctggtgggg | ccccagcggc | tgcaggtgct | gaatgcctcc | 300 |
| cacgaggact | ccggggccta | cagctgccgg | cagcggctca | cgcagcgcgt | actgtgccac | 360 |
| ttcagtgtgc | gggtgacaga | cgctccatcc | tcgggagatg | acgaagacgg | ggaggacgag | 420 |
| gctgaggaca | caggtgtgga | cacaggggcc | ccttactgga | cacggcccga | gcggatggac | 480 |
| aagaagctgc | tggccgtgcc | ggccgccaac | accgtccgct | tccgctgccc | agccgctggc | 540 |
| aaccccactc | cctccatctc | ctggctgaag | aacggcaggg | agttccgcgg | cgagcaccgc | 600 |
| attggaggca | tcaagctgcg | gcatcagcag | tggagcctgg | tcatggaaag | cgtggtgccc | 660 |
| tcggaccgcg | gcaactacac | ctgcgtcgtg | gagaacaagt | ttggcagcat | ccggcagacg | 720 |
| tacacgctgg | acgtgctgga | gcgctcccg | caccggccca | tcctgcaggc | ggggctgccg | 780 |
| gccaaccaga | cggcggtgct | gggcagcgac | gtggagttcc | actgcaaggt | gtacagtgac | 840 |
| gcacagcccc | acatccagtg | gctcaagcac | gtggaggtga | acggcagcaa | ggtgggcccg | 900 |
| gacggcacac | cctacgttac | cgtgctcaag | tcctggatca | gtgagagtgt | ggaggccgac | 960 |
| gtgcgcctcc | gcctggccaa | tgtgtcggag | cgggacgggg | gcgagtacct | ctgtcgagcc | 1020 |
| accaatttca | taggcgtggc | cgagaaggcc | ttttggctga | gcgttcacgg | gccccgagca | 1080 |
| gccgaggagg | agctggtgga | ggctgacgag | gcgggctgtg | tgtatgcagg | catcctcagc | 1140 |
| tacgggtgg | gcttcttcct | gttcatcctg | gtggtggcgg | ctgtgacgct | ctgccgcctg | 1200 |
| cgcagccccc | ccaagaaagg | cctgggctcc | ccaccgtgc | acaagatctc | ccgcttcccg | 1260 |
| ctcaagcgac | aggtgtccct | ggagtccaac | gcgtccatga | gctccaacac | accactggtg | 1320 |
| cgcatcgcaa | ggctgtcctc | aggggagggc | cccacgctgg | ccaatgtctc | cgagctcgag | 1380 |
| ctgcctgccg | accccaaatg | ggagctgtct | cgggcccggc | tgaccctggg | caagccctt | 1440 |
| ggggagggct | gcttcggcca | ggtggtcatg | gcggaggcca | tcggcattga | caaggaccgg | 1500 |
| gccgccaagc | ctgtcaccgt | agccgtgaag | atgctgaaag | acgatgccac | tgacaaggac | 1560 |
| ctgtcggacc | tggtgtctga | gatggagatg | atgaagatga | tcgggaaaca | caaaaacatc | 1620 |
| atcaacctgc | tgggcgcctg | cacgcagggc | gggccctgt | acgtgctggt | ggagtacgcg | 1680 |
| gccaagggta | acctgcggga | gtttctgcgg | gcgcggcggc | ccccgggcct | ggactactcc | 1740 |
| ttcgacacct | gcaagccgcc | cgaggagcag | ctcaccttca | aggacctggt | gtcctgtgcc | 1800 |
| taccaggtgg | cccggggcat | ggagtacttg | gcctcccaga | agtgcatcca | cagggacctg | 1860 |
| gctgcccgca | atgtgctggt | gaccgaggac | aacgtgatga | agatcgcaga | cttcgggctg | 1920 |
| gcccgggacg | tgcacaacct | cgactactac | aagaagacaa | ccaacggccg | gctgcccgtg | 1980 |
| aagtggatgg | cgcctgaggc | cttgtttgac | cgagtctaca | ctcaccagag | tgacgtctgg | 2040 |
| tcctttgggg | tcctgctctg | ggagatcttc | acgctggggg | ctccccgta | cccggcatc | 2100 |
| cctgtggagg | agctcttcaa | gctgctgaag | gagggccacc | gcatggacaa | gcccgccaac | 2160 |
| tgcacacacg | acctgtacat | gatcatgcgg | gagtgctggc | atgccgcgcc | ctcccagagg | 2220 |

```
cccaccttca agcagctggt ggaggacctg gaccgtgtcc ttaccgtgac gtccaccgac    2280
gagtacctgg acctgtcggc gcctttcgag cagtactccc cgggtggcca ggacaccccc    2340
agctccagct cctcagggga cgactccgtg tttgcccacg acctgctgcc cccggcccca    2400
cccagcagtg ggggctcgcg gacgtga                                         2427
```

<210> SEQ ID NO 7
<211> LENGTH: 2427
<212> TYPE: DNA
<213> ORGANISM: Artificial Sequence
<220> FEATURE:
<223> OTHER INFORMATION: Description of Artificial Sequence:Mutant Y375C
      FGFR3-IIIb:

<400> SEQUENCE: 7

```
atgggcgccc ctgcctgcgc cctcgcgctc tgcgtggccg tggccatcgt ggccggcgcc    60
tcctcggagt ccttggggac ggagcagcgc gtcgtgggc gagcggcaga agtcccgggc    120
ccagagcccg gccagcagga gcagttggtc ttcggcagcg gggatgctgt ggagctgagc    180 tgtccccgc ccgggggtgg tcccatgggg cccactgtct gggtcaagga tggcacaggg    240
ctggtgccct cggagcgtgt cctggtgggg ccccagcggc tgcaggtgct gaatgcctcc    300
cacgaggact ccgggcccta cagctgccgg cagcggctca cgcagcgcgt actgtgccac    360
ttcagtgtgc gggtgacaga cgctccatcc tcgggagatg acgaagacgg ggaggacgag    420
gctgaggaca caggtgtgga cacaggggcc ccttactgga cacggcccga gcggatggac    480
aagaagctgc tggccgtgcc ggccgccaac accgtcgcct tccgctgccc agccgctggc    540
aaccccactc cctccatctc ctggctgaag aacggcaggg agttccgcgg cgagcaccgc    600
attggaggca tcaagctgcg gcatcagcag tggagcctgg tcatggaaag cgtggtgccc    660
tcggaccgcg gcaactacac ctgcgtcgtg gagaacaagt tggcagcat ccggcagacg    720 tacacgctgg acgtgctgga gcgctcccg caccggccca tcctgcaggc ggggctgccg    780
gccaaccaga cggcggtgct gggcagcgac gtggagttcc actgcaaggt gtacagtgac    840
gcacagcccc acatccagtg gctcaagcac gtggaggtga cggcagcaa ggtgggcccg    900 gacggcacac cctacgttac cgtgctcaag tcctggatca gtgagagtgt ggaggccgac    960
gtgcgcctcc gcctggccaa tgtgtcggag cgggacgggg gcgagtacct ctgtcgagcc    1020
accaatttca taggcgtggc cgagaaggcc ttttggctga cgttcacgg gccccgagca    1080 gccgaggagg agctggtgga ggctgacgag gcgggcagtg tgtgtgcagg catcctcagc    1140 tacgggtgg gcttcttcct gttcatcctg gtggtggcgg ctgtgacgct ctgccgcctg    1200
cgcagccccc caagaaagg cctgggctcc ccaccgtgc acaagatctc ccgcttcccg    1260
ctcaagcgac aggtgtccct ggagtccaac gcgtccatga gctccaacac accactggtg    1320
cgcatcgcaa ggctgtcctc agggagggc cccacgctgg ccaatgtctc cgagctcgag    1380
ctgcctgccg acccaaatg ggagctgtct cgggcccggc tgaccctggg caagcccctt    1440
ggggagggct gcttcggcca ggtggtcatg gcggaggcca tcggcattga caaggaccgg    1500
gccgccaagc ctgtcaccgt agccgtgaag atgctgaaag acgatgccac tgacaaggac    1560
ctgtcggacc tggtgtctga gatggagatg atgaagatga tcgggaaaca caaaaacatc    1620
atcaacctgc tgggcgcctg cacgcagggc gggcccctgt acgtgctggt ggagtacgcg    1680
gccaagggta acctgcggga gtttctgcgg gcgcggcggc ccccgggcct ggactactcc    1740
ttcgacaccc tgcaagccgc cgaggagcag ctcaccttca aggacctggt gtcctgtgcc    1800
```

```
taccaggtgg cccgggcat ggagtacttg gcctcccaga agtgcatcca cagggacctg    1860
gctgcccgca atgtgctggt gaccgaggac aacgtgatga agatcgcaga cttcgggctg    1920
gcccgggacg tgcacaacct cgactactac aagaagacaa ccaacggccg gctgcccgtg    1980
aagtggatgg cgcctgaggc cttgtttgac cgagtctaca ctcaccagag tgacgtctgg    2040
tcctttgggg tcctgctctg ggagatcttc acgctggggg gctccccgta ccccggcatc    2100
cctgtggagg agctcttcaa gctgctgaag gagggccacc gcatggacaa gcccgccaac    2160
tgcacacacg acctgtacat gatcatgcgg gagtgctggc atgccgcgcc ctcccagagg    2220
cccaccttca gcagctggt ggaggacctg accgtgtcc ttaccgtgac gtccaccgac    2280
gagtacctgg acctgtcggc gcctttcgag cagtactccc cggtggcca ggacaccccc    2340 agctccagct cctcagggga cgactccgtg tttgcccacg acctgctgcc cccggcccca    2400
cccagcagtg ggggctcgcg gacgtga                                        2427

<210> SEQ ID NO 8
<211> LENGTH: 2427
<212> TYPE: DNA
<213> ORGANISM: Artificial Sequence
<220> FEATURE:
<223> OTHER INFORMATION: Description of Artificial Sequence:Mutant K652M
      FGFR3-IIIb:

<400> SEQUENCE: 8
atgggcgccc ctgcctgcgc cctcgcgctc tgcgtggccg tggccatcgt ggccggcgcc    60
tcctcggagt ccttggggac ggagcagcgc gtcgtggggc gagcggcaga agtcccgggc   120
ccagagcccg gccagcagga gcagttggtc ttcggcagcg gggatgctgt ggagctgagc   180 tgtccccgc ccggggtgg tcccatgggg cccactgtct gggtcaagga tgcacaggg    240 ctggtgccct cggagcgtgt cctggtgggg ccccagcggc tgcaggtgct gaatgcctcc   300
cacgaggact ccgggccta cagctgccgg cagcggctca cgcagcgcgt actgtgccac   360
ttcagtgtgc gggtgacaga cgctccatcc tcgggagatg acgaagacgg ggaggacgag   420
gctgaggaca caggtgtgga cacaggggcc ccttactgga cacggcccga gcggatggac   480
aagaagctgc tggccgtgcc ggccgccaac accgtccgct tccgctgccc agccgctggc   540
aaccccactc cctccatctc ctggctgaag aacggcaggg agttccgcgg cgagcaccgc   600
attggaggca tcaagctgcg gcatcagcag tggagcctgg tcatggaaag cgtggtgccc   660
tcggaccgcg gcaactacac ctgcgtcgtg gagaacaagt ttggcagcat ccggcagacg   720
tacacgctgg acgtgctgga gcgctcccg caccggccca tcctgcaggc ggggctgccg   780
gccaaccaga cggcggtgct gggcagcgac gtggagttcc actgcaaggt gtacagtgac   840
gcacagcccc acatccagtg gctcaagcac gtggaggtga acggcagcaa ggtgggcccg   900
gacggcacac cctacgttac cgtgctcaag tcctggatca gtgagagtgt ggaggccgac   960
gtgcgcctcc gcctggccaa tgtgtcggag cgggacgggg cgagtacct ctgtcgagcc   1020 accaatttca taggcgtggc cgagaaggcc ttttggctga gcgttcacgg gccccgagca   1080
gccgaggagg agctggtgga ggctgacgag gcgggcagtg tgtatgcagg catcctcagc   1140 tacgggtgg gcttcttcct gttcatcctg gtggtggcgg ctgtgacgct gccgcctg    1200 cgcagccccc caagaaagg cctgggctcc ccaccgtgc acaagatctc ccgcttcccg   1260
ctcaagcgac aggtgtccct ggagtccaac gcgtccatga gctccaacac caccgtggtg   1320
cgcatcgcaa ggctgtcctc aggggagggc cccacgctgg ccaatgtctc cgagctcgag   1380
```

```
ctgcctgccg accccaaatg ggagctgtct cgggcccggc tgaccctggg caagccccct   1440
ggggagggct gcttcggcca ggtggtcatg gcggaggcca tcggcattga caaggaccgg   1500
gccgccaagc tgtcaccgt agccgtgaag atgctgaaag acgatgccac tgacaaggac    1560
ctgtcggacc tggtgtctga gatggagatg atgaagatga tcgggaaaca caaaaacatc   1620
atcaacctgc tgggcgcctg cacgcagggc gggcccctgt acgtgctggt ggagtacgcg   1680
gccaagggta acctgcggga gtttctgcgg gcgcggcggc ccccgggcct ggactactcc   1740
ttcgacacct gcaagccgcc cgaggagcag ctcaccttca aggacctggt gtcctgtgcc   1800
taccaggtgg cccggggcat ggagtacttg gcctcccaga agtgcatcca cagggacctg   1860
gctgcccgca atgtgctggt gaccgaggac aacgtgatga gatcgcaga cttcgggctg    1920 gcccgggacg tgcacaacct cgactactac aagatgacaa ccaacggccg gctgccgtg    1980 aagtggatgg cgcctgaggc cttgtttgac cgagtctaca ctcaccagag tgacgtctgg   2040
tcctttgggg tcctgctctg ggagatcttc acgctggggg gctccccgta ccccggcatc   2100
cctgtggagg agctcttcaa gctgctgaag gagggccacc gcatggacaa gcccgccaac   2160
tgcacacacg acctgtacat gatcatgcgg gagtgctgga tgccgcgcc ctcccagagg    2220 cccaccttca gcagctggt ggaggacctg gaccgtgtcc ttaccgtgac gtccaccgac    2280
gagtacctgg acctgtcggc gcctttcgag cagtactccc cgggtggcca ggacaccccc   2340
agctccagct cctcagggga cgactccgtg tttgcccacg acctgctgcc cccggcccca   2400
cccagcagtg ggggctcgcg gacgtga                                       2427

<210> SEQ ID NO 9
<211> LENGTH: 2427
<212> TYPE: DNA
<213> ORGANISM: Artificial Sequence
<220> FEATURE:
<223> OTHER INFORMATION: Description of Artificial Sequence:Mutant X809C
      FGFR3-IIIb:

<400> SEQUENCE: 9
atgggcgccc ctgcctgcgc cctcgcgctc tgcgtggccg tggccatcgt ggccggcgcc     60
tcctcggagt ccttggggac ggagcagcgc gtcgtgggc gagcggcaga agtcccgggc    120
ccagagcccg gccagcagga gcagttggtc ttcggcagcg gggatgctgt ggagctgagc    180 tgtccccgc ccggggtgg tcccatgggg cccactgtct gggtcaagga tggcacaggg    240
ctggtgccct cggagcgtgt cctggtgggg ccccagcggc tgcaggtgct gaatgcctcc    300
cacgaggact ccgggccta cagctgccgg cagcggctca gcagcgcgt actgtgccac    360 ttcagtgtgc gggtgacaga cgctccatcc tcgggagatg acgaagacgg ggaggacgag    420
gctgaggaca caggtgtgga cacgggggcc ccttactgga cacggcccga gcggatggac    480
aagaagctgc tggccgtgcc ggccgccaac accgtccgct ccgctgccc agccgctggc    540 aaccccactc cctccatctc ctggctgaag aacggcaggg agttccgcgg cgagcaccgc    600
attggaggca tcaagctgcg gcatcagcag tggagcctgg tcatgaaag cgtggtgccc    660 tcggaccgcg gcaactacac ctgcgtcgtg gagaacaagt tggcagcat ccggcagacg    720 tacacgctgg acgtgctgga gcgctcccg caccggccca tcctgcaggc ggggctgccg    780
gccaaccaga cggcggtgct gggcagcgac gtggagttcc actgcaaggt gtacagtgac    840
gcacagcccc acatccagtg gctcaagcac gtggaggtga acggcagcaa ggtgggcccg    900
gacggcacac cctacgttac cgtgctcaag tcctggatca gtgagagtgt ggaggccgac    960
```

-continued

```
gtgcgcctcc gcctggccaa tgtgtcggag cgggacgggg gcgagtacct ctgtcgagcc   1020
accaatttca taggcgtggc cgagaaggcc ttttggctga gcgttcacgg ccccgagca   1080 gccgaggagg agctggtgga ggctgacgag gcgggcagtg tgtatgcagg catcctcagc   1140
tacggggtgg gcttcttcct gttcatcctg gtggtggcgg ctgtgacgct ctgccgcctg   1200
cgcagccccc ccaagaaagg cctgggctcc ccaccgtgc acaagatctc ccgcttcccg   1260
ctcaagcgac aggtgtccct ggagtccaac gcgtccatga gctccaacac accactggtg   1320
cgcatcgcaa ggctgtcctc aggggagggc cccacgctgg ccaatgtctc cgagctcgag   1380
ctgcctgccg accccaaatg ggagctgtct cgggcccggc tgaccctggg caagccctt   1440 ggggagggct gcttcggcca ggtggtcatg gcggaggcca tcggcattga caaggaccgg   1500
gccgccaagc tgtcaccgt agccgtgaag atgctgaaag acgatgccac tgacaaggac   1560
ctgtcggacc tggtgtctga gatggagatg atgaagatga tcgggaaaca caaaaacatc   1620
atcaacctgc tgggcgcctg cacgcagggc gggcccctgt acgtgctggt ggagtacgcg   1680
gccaagggta acctgcggga gtttctgcgg gcgcggcggc cccgggcct ggactactcc   1740 ttcgacacct gcaagccgcc cgaggagcag ctcaccttca aggacctggt gtcctgtgcc   1800
taccaggtgg cccgggcat ggagtacttg gcctcccaga gtgcatcca cagggacctg   1860 gctgcccgca atgtgctggt gaccgaggac aacgtgatga agatcgcaga cttcgggctg   1920
gcccgggacg tgcacaacct cgactactac aagaagacaa ccaacggccg gctgcccgtg   1980
aagtggatgg cgcctgaggc cttgtttgac cgagtctaca ctcaccagag tgacgtctgg   2040
tcctttgggg tcctgctctg ggagatcttc acgctggggg ctccccgta ccccggcatc   2100 cctgtggagg agctcttcaa gctgctgaag gagggccacc gcatgacaa gcccgccaac   2160 tgcacacacg acctgtacat gatcatgcgg gagtgctggc atgccgcgcc ctcccagagg   2220
cccaccttca gcagctggt ggaggacctg gaccgtgtcc ttaccgtgac gtccaccgac   2280
gagtacctgg acctgtcggc gcctttcgag cagtactccc cgggtggcca ggacaccccc   2340
agctccagct cctcagggga cgactccgtg tttgcccacg acctgctgcc ccggccccca   2400
cccagcagtg ggggctcgcg gacgtgc                                        2427
```

<210> SEQ ID NO 10
<211> LENGTH: 2427
<212> TYPE: DNA
<213> ORGANISM: Artificial Sequence
<220> FEATURE:
<223> OTHER INFORMATION: Description of Artificial Sequence:Mutant X809G
      FGFR3-IIIb:
      (Mutant 1)

<400> SEQUENCE: 10

```
atgggcgccc ctgcctgcgc cctcgcgctc tgcgtggccg tggccatcgt ggccggcgcc     60
tcctcggagt ccttggggac ggagcagcgc gtcgtgggc gagcggcaga agtcccgggc   120
ccagagcccg ccagcagga gcagttggtc ttcggcagcg gggatgctgt ggagctgagc   180 tgtccccgc ccggggggtgg tcccatgggg cccactgtct gggtcaagga tggcacaggg   240
ctggtgccct cggagcgtgt cctggtgggg ccccagcggc tgcaggtgct gaatgcctcc    300
cacgaggact ccggggccta cagctgccgg cagcggctca cgcagcgcgt actgtgccac   360
ttcagtgtgc gggtgacaga cgctccatcc tcgggagatg acgaagacgg ggaggacgag   420
gctgaggaca caggtgtgga cacaggggcc ccttactgga cacggcccga gcggatggac   480
```

```
aagaagctgc tggccgtgcc ggccgccaac accgtccgct tccgctgccc agccgctggc    540
aaccccactc cctccatctc ctggctgaag aacggcagga gttccgcgg cgagcaccgc    600 attggaggca tcaagctgcg gcatcagcag tggagcctgg tcatggaaag cgtggtgccc    660
tcggaccgcg gcaactacac ctgcgtcgtg gagaacaagt ttggcagcat ccggcagacg    720
tacacgctgg acgtgctgga gcgctccccg caccggccca tcctgcaggc ggggctgccg    780
gccaaccaga cggcggtgct gggcagcgac gtggagttcc actgcaaggt gtacagtgac    840
gcacagcccc acatccagtg gctcaagcac gtggaggtga acggcagcaa ggtgggcccg    900
gacggcacac cctacgttac cgtgctcaag tcctggatca gtgagagtgt ggaggccgac    960
gtgcgcctcc gcctggccaa tgtgtcggag cgggacgggg gcgagtacct ctgtcgagcc   1020
accaatttca taggcgtggc cgagaaggcc ttttggctga cgttcacgg gccccgagca   1080 gccgaggagg agctggtgga ggctgacgag gcgggcagtg tgtatgcagg catcctcagc   1140 tacgggtgg gcttcttcct gttcatcctg gtggtggcgg ctgtgacgct ctgccgcctg   1200
cgcagccccc ccaagaaagg cctgggctcc ccaccgtgc acaagatctc ccgcttcccg   1260
ctcaagcgac aggtgtccct ggagtccaac gcgtccatga gctccaacac accactggtg   1320
cgcatcgcaa ggctgtcctc aggggagggc cccacgctgg ccaatgtctc cgagctcgag   1380
ctgcctgccg accccaaatg ggagctgtct cgggcccggc tgaccctggg caagccctt   1440 ggggagggct gcttcggcca ggtggtcatg gcggaggcca tcggcattga caaggaccgg   1500
gccgccaagc ctgtcaccgt agccgtgaag atgctgaaag acgatgccac tgacaaggac   1560
ctgtcggacc tggtgtctga gatggagatg atgaagatga tcgggaaaca caaaaacatc   1620
atcaacctgc tgggcgcctg cacgcagggc gggcccctgt acgtgctggt ggagtacgcg   1680
gccaagggta acctgcggga gtttctgcgg gcgcggcggc cccgggcct ggactactcc   1740 ttcgacacct gcaagccgcc cgaggagcag ctcaccttca aggacctggt gtcctgtgcc   1800
taccaggtgg cccgggcat ggagtacttg gcctcccaga gtgcatcca cagggacctg   1860 gctgccgca atgtgctggt gaccgaggac aacgtgatga agatcgcaga cttcgggctg   1920
gcccgggacg tgcacaacct cgactactac aagaagacaa ccaacggccg gctgcccgtg   1980
aagtggatgg cgcctgaggc cttgtttgac cgagtctaca ctcaccgag tgacgtctgg   2040 tcctttgggg tcctgctctg ggagatcttc acgctggggg gctccccgta ccccggcatc   2100
cctgtggagg agctcttcaa gctgctgaag gagggccacc gcatggacaa gcccgccaac   2160
tgcacacacg acctgtacat gatcatgcgg gagtgctgga tgccgcgcc ctcccagagg   2220 cccaccttca gcagctggt ggaggacctg gaccgtgtcc ttaccgtgac gtccaccgac   2280
gagtacctgg acctgtcggc gcctttcgag cagtactccc cggtggcca ggacaccccc   2340 agctccagct cctcagggga cgactccgtg tttgcccacg acctgctgcc cccggcccca   2400
cccagcagtg ggggctcgcg gacggga                                       2427
```

<210> SEQ ID NO 11
<211> LENGTH: 2427
<212> TYPE: DNA
<213> ORGANISM: Artificial Sequence
<220> FEATURE:
<223> OTHER INFORMATION: Description of Artificial Sequence:Mutant X809G
      FGFR3-IIIb:
      (Mutant 2)

<400> SEQUENCE: 11

```
atgggcgccc ctgcctgcgc cctcgcgctc tgcgtggccg tggccatcgt ggccggcgcc    60
```

-continued

```
tcctcggagt ccttggggac ggagcagcgc gtcgtggggc gagcggcaga agtcccgggc      120
ccagagcccg gccagcagga gcagttggtc ttcggcagcg gggatgctgt ggagctgagc      180
tgtcccccgc ccggggqtgg tcccatgggg cccactgtct gggtcaagga tggcacaggg      240
ctggtgccct cggagcgtgt cctggtgggg ccccagcggc tgcaggtgct gaatgcctcc      300
cacgaggact ccggggccta cagctgccgg cagcggctca cgcagcgcgt actgtgccac      360
ttcagtgtgc gggtgacaga cgctccatcc tcgggagatg acgaagacgg ggaggacgag      420
gctgaggaca caggtgtgga cacaggggcc ccttactgga cacggcccga gcggatggac      480
aagaagctgc tggccgtgcc ggccgccaac accgtccgct tccgctgccc agccgctggc      540
aaccccactc cctccatctc ctggctgaag aacggcaggg agttccgcgg cgagcaccgc      600
attggaggca tcaagctgcg gcatcagcag tggagcctgg tcatggaaag cgtggtgccc      660
tcggaccgcg gcaactacac ctgcgtcgtg gagaacaagt tggcagcat ccggcagacg       720 tacacgctgg acgtgctgga gcgctccccg caccggccca tcctgcaggc ggggctgccg      780
gccaaccaga cggcggtgct gggcagcgac gtggagttcc actgcaaggt gtacagtgac      840
gcacagcccc acatccagtg gctcaagcac gtggaggtga acggcagcaa ggtgggcccg      900
gacggcacac cctacgttac cgtgctcaag tcctggatca gtgagagtgt ggaggccgac      960
gtgcgcctcc gcctggccaa tgtgtcggag cgggacgggg cgagtacct ctgtcgagcc      1020 accaatttca taggcgtggc cgagaaggcc ttttggctga cgttcacgg gccccgagca      1080 gccgaggagg agctggtgga ggctgacgag gcgggcagtg tgtatgcagg catcctcagc      1140 tacgggtgg gcttcttcct gttcatcctg gtggtggcgg ctgtgacgct ctgccgcctg      1200
cgcagccccc ccaagaaagg cctgggctcc cccaccgtgc acaagatctc ccgcttcccg      1260
ctcaagcgac aggtgtccct ggagtccaac gcgtccatga gctccaacac accactggtg      1320
cgcatcgcaa ggctgtcctc aggggagggc cccacgctgg ccaatgtctc cgagctcgag      1380
ctgcctgccg accccaaatg ggagctgtct cgggcccggc tgaccctggg caagcccctt      1440
ggggagggct gcttcggcca ggtggtcatg gcggaggcca tcggcattga caaggaccgg      1500
gccgccaagc ctgtcaccgt agccgtgaag atgctgaaag acgatgccac tgacaaggac      1560
ctgtcggacc tggtgtctga gatggagatg atgaagatga tcgggaaaca caaaaacatc      1620
atcaacctgc tgggcgcctg cacgcagggc gggcccctgt acgtgctggt ggagtacgcg      1680
gccaagggta acctgcggga gtttctgcgg gcgcggcggc cccgggcct ggactactcc       1740 ttcgacacct gcaagccgcc cgaggagcag ctcaccttca aggacctggt gtcctgtgcc      1800
taccaggtgg cccgggggcat ggagtacttg gcctcccaga agtgcatcca cagggacctg      1860
gctgcccgca atgtgctggt gaccgaggac aacgtgatga agatcgcaga cttcgggctg      1920
gcccgggacg tgcacaacct cgactactac aagaagacaa ccaacggccg gctgcccgtg      1980
aagtggatgg cgcctgaggc cttgtttgac cgagtctaca ctcaccagag tgacgtctgg      2040
tcctttgggg tcctgctctg ggagatcttc acgctggggg ctccccgta ccccggcatc      2100 cctgtggagg agctcttcaa gctgctgaag gagggccacc gcatggacaa gcccgccaac      2160
tgcacacacg acctgtacat gatcatgcgg gagtgctggc atgccgcgcc ctcccagagg      2220
cccaccttca agcagctggt ggaggacctg gaccgtgtcc ttaccgtgac gtccaccgac      2280
gagtacctgg acctgtcggc gccttttgag cagtactccc cggtggccca ggacacccc      2340 agctccagct cctcagggga cgactccgtg tttgcccacg acctgctgcc cccggccca      2400
```

| cccagcagtg ggggctcgcg gacgaga | 2427 |

<210> SEQ ID NO 12
<211> LENGTH: 2427
<212> TYPE: DNA
<213> ORGANISM: Artificial Sequence
<220> FEATURE:
<223> OTHER INFORMATION: Description of Artificial Sequence:Mutant X809G
      FGFR3-IIIb:
      (Mutant 3)

<400> SEQUENCE: 12

| atgggcgccc ctgcctgcgc cctcgcgctc tgcgtggccg tggccatcgt ggccggcgcc | 60 |
| tcctcggagt ccttggggac ggagcagcgc gtcgtggggc gagcggcaga agtcccgggc | 120 |
| ccagagcccg gccagcagga gcagttggtc ttcggcagcg gggatgctgt ggagctgagc | 180 |
| tgtccccgc cggggggtgg tcccatgggg cccactgtct gggtcaagga tggcacaggg | 240 |
| ctggtgccct cggagcgtgt cctggtgggg cccagcggc tgcaggtgct gaatgcctcc | 300 |
| cacgaggact ccggggccta cagctgccgg cagcggctca cgcagcgcgt actgtgccac | 360 |
| ttcagtgtgc gggtgacaga cgctccatcc tcgggagatg acgaagacgg ggaggacgag | 420 |
| gctgaggaca caggtgtgga cacaggggcc ccttactgga cacggcccga gcggatggac | 480 |
| aagaagctgc tggccgtgcc ggccgccaac ccgtccgct tccgctgccc agccgctggc | 540 |
| aaccccactc cctccatctc ctggctgaag aacggcaggg agttccgcgg cgagcaccgc | 600 |
| attggaggca tcaagctgcg gcatcagcag tggagcctgg tcatggaaag cgtggtgccc | 660 |
| tcggaccgcg gcaactacac ctgcgtcgtg gagaacaagt ttggcagcat ccggcagacg | 720 |
| tacacgctgg acgtgctgga cgctcccccg caccggccca tcctgcaggc ggggctgccg | 780 |
| gccaaccaga cggcggtgct gggcagcgac gtggagttcc actgcaaggt gtacagtgac | 840 |
| gcacagcccc acatccagtg gctcaagcac gtggaggtga acggcagcaa ggtgggcccg | 900 |
| gacggcacac cctacgttac cgtgctcaag tcctggatca gtgagagtgt ggaggccgac | 960 |
| gtgcgcctcc gcctggccaa tgtgtcggag cgggacgggg cgagtacct ctgtcgagcc | 1020 |
| accaatttca taggcgtggc cgagaaggcc ttttggctga gcgttcacgg gccccgagca | 1080 |
| gccgaggagg agctggtgga ggctgacgag gcgggcagtg tgtatgcagg catcctcagc | 1140 |
| tacggggtgg gcttcttcct gttcatcctg gtggtggcgg ctgtgacgct ctgccgcctg | 1200 |
| cgcagccccc ccaagaaagg cctgggctcc ccaccgtgc acaagatctc ccgcttcccg | 1260 |
| ctcaagcgac aggtgtccct ggagtccaac gcgtccatga gctccaacac accactggtg | 1320 |
| cgcatcgcaa ggctgtcctc aggggagggc cccacgctgg ccaatgtctc cgagctcgag | 1380 |
| ctgcctgccg accccaaatg ggagctgtct cgggcccggc tgaccctggg caagcccctt | 1440 |
| ggggagggct gcttcggcca ggtggtcatg gcggaggcca tcggcattga caaggaccgg | 1500 |
| gccgccaagc ctgtcaccgt agccgtgaag atgctgaaag acgatgccac tgacaaggac | 1560 |
| ctgtcggacc tggtgtctga gatggagatg atgaagatga tcgggaaaca caaaaacatc | 1620 |
| atcaacctgc tggcgcctg cacgcagggc gggcccctgt acgtgctggt ggagtacgcg | 1680 |
| gccaagggta acctgcggga gtttctgcgg gcgcggcggc ccccggggcct ggactactcc | 1740 |
| ttcgacacct gcaagccgcc cgaggagcag ctcaccttca aggacctggt gtcctgtgcc | 1800 |
| taccaggtgg cccggggcat ggagtacttg gcctcccaga gtgcatcca caggacctg | 1860 |
| gctgcccgca atgtgctggt gaccgaggac aacgtgatga gatcgcaga cttcgggctg | 1920 |
| gcccgggacg tgcacaacct cgactactac aagaagacaa ccaacggccg gctgcccgtg | 1980 |

-continued

```
aagtggatgg cgcctgaggc cttgtttgac cgagtctaca ctcaccagag tgacgtctgg   2040
tcctttgggg tcctgctctg ggagatcttc acgctggggg gctccccgta cccggcatc    2100 cctgtggagg agctcttcaa gctgctgaag gagggccacc gcatggacaa gcccgccaac   2160
tgcacacacg acctgtacat gatcatgcgg gagtgctggc atgccgcgcc ctcccagagg   2220
cccaccttca agcagctggt ggaggacctg gaccgtgtcc ttaccgtgac gtccaccgac   2280
gagtacctgg acctgtcggc gcctttcgag cagtactccc cgggtggcca ggacaccccc   2340
agctccagct cctcagggga cgactccgtg tttgcccacg acctgctgcc cccggcccca   2400
cccagcagtg ggggctcgcg gacgcga                                        2427
```

<210> SEQ ID NO 13
<211> LENGTH: 2427
<212> TYPE: DNA
<213> ORGANISM: Artificial Sequence
<220> FEATURE:
<223> OTHER INFORMATION: Description of Artificial Sequence:Mutant X809L
    FGFR3-IIIb:

<400> SEQUENCE: 13

```
atgggcgccc ctgcctgcgc cctcgcgctc tgcgtggccg tggccatcgt ggccggcgcc   60
tcctcggagt ccttggggac ggagcagcgc gtcgtgggc gagcggcaga agtcccgggc    120
ccagagcccg ccagcagga gcagttggtc ttcggcagcg gggatgctgt ggagctgagc    180
tgtcccccgc ccgggggtgg tcccatgggg cccactgtct gggtcaagga tggcacaggg   240
ctggtgccct cggagcgtgt cctggtgggg cccagcggc tgcaggtgct gaatgcctcc    300
cacgaggact ccgggccta cagctgccgg cagcggctca cgcagcgcgt actgtgccac   360
ttcagtgtgc gggtgacaga cgctccatcc tcgggagatg acgaagacgg ggaggacgag   420
gctgaggaca caggtgtgga cacaggggcc ccttactgga cacggcccga gcggatggac   480
aagaagctgc tggccgtgcc ggccgccaac accgtccgct tccgctgccc agccgctggc   540
aaccccactc cctccatctc ctggctgaag aacggcaggg agttccgcgg cgagcaccgc   600
attggaggca tcaagctgcg gcatcagcag tggagcctgg tcatggaaag cgtggtgccc   660
tcggaccgcg gcaactacac ctgcgtcgtg gagaacaagt ttggcagcat ccggcagacg   720
tacacgctgg acgtgctgga gcgctccccg caccggccca cctgcaggc ggggctgccg    780 gccaaccaga cggcggtgct ggcagcgac gtggagttcc actgcaaggt gtacagtgac    840
gcacagcccc acatccagtg gctcaagcac gtggaggtga acggcagcaa ggtggcccg    900 gacggcacac cctacgttac cgtgctcaag tcctggatca gtgagagtgt ggaggccgac   960
gtgcgcctcc gcctggccaa tgtgtcggag cgggacgggg cgagtacct ctgtcgagcc    1020 accaatttca taggcgtggc cgagaaggcc ttttggctga cgttcacgg gccccgagca   1080 gccgaggagg agctggtgga ggctgacgag gcgggcagtg tgtatgcagg catcctcagc   1140 tacgggtg gcttcttcct gttcatcctg gtggtggcgg ctgtgacgct ctgccgcctg   1200
cgcagccccc ccaagaaagg cctgggctcc ccaccgtgc acaagatctc ccgcttcccg   1260
ctcaagcgac aggtgtccct ggagtccaac gcgtccatga gctccaacac accactggtg   1320
cgcatcgcaa ggctgtcctc aggggagggc cccacgctgg ccaatgtctc cgagctcgag   1380
ctgcctgccg accccaaatg ggagctgtct cgggcccggc tgaccctggg caagcccctt   1440
ggggagggct gcttcggcca ggtggtcatg gcggaggcca tcggcattga caaggaccgg   1500
gccgccaagc ctgtcaccgt agccgtgaag atgctgaaag acgatgccac tgacaaggac   1560
```

-continued

```
ctgtcggacc tggtgtctga gatggagatg atgaagatga tcgggaaaca caaaaacatc    1620
atcaacctgc tgggcgcctg cacgcagggc gggcccctgt acgtgctggt ggagtacgcg    1680
gccaagggta acctgcggga gtttctgcgg gcgcggcggc ccccgggcct ggactactcc    1740
ttcgacacct gcaagccgcc cgaggagcag ctcaccttca aggacctggt gtcctgtgcc    1800
taccaggtgg cccggggcat ggagtacttg gcctcccaga gtgcatcca cagggacctg    1860 gctgcccgca tgtgctggt gaccgaggac aacgtgatga agatcgcaga cttcgggctg    1920
gcccgggacg tgcacaacct cgactactac aagaagacaa ccaacggccg gctgcccgtg    1980
aagtggatgg cgcctgaggc cttgtttgac cgagtctaca ctcaccagag tgacgtctgg    2040
tcctttgggg tcctgctctg ggagatcttc acgctggggg ctccccgta ccccggcatc    2100 cctgtggagg agctcttcaa gctgctgaag gagggccacc gcatggacaa gcccgccaac    2160
tgcacacacg acctgtacat gatcatgcgg gagtgctggc atgccgcgcc ctcccagagg    2220
cccaccttca gcagctggt ggaggacctg gaccgtgtcc ttaccgtgac gtccaccgac    2280
gagtacctgg acctgtcggc gccttttcgag cagtactccc cggtggcca ggacaccccc    2340 agctccagct cctcagggga cgactccgtg tttgcccacg acctgctgcc cccggccca    2400 cccagcagtg ggggctcgcg gacgtta                                         2427
```

<210> SEQ ID NO 14
<211> LENGTH: 2427
<212> TYPE: DNA
<213> ORGANISM: Artificial Sequence
<220> FEATURE:
<223> OTHER INFORMATION: Description of Artificial Sequence:Mutant N542K
      FGFR3-IIIb:
      (Mutant 1)

<400> SEQUENCE: 14

```
atgggcgccc ctgcctgcgc cctcgcgctc tgcgtggccg tggccatcgt ggccggcgcc      60
tcctcggagt ccttggggac ggagcagcgc gtcgtgggc gagcggcaga agtcccgggc     120
ccagagcccg gccagcagga gcagttggtc ttcggcagcg gggatgctgt ggagctgagc     180 tgtccccgc ccggggtgg tcccatgggg cccactgtct gggtcaagga tggcacaggg     240
ctggtgccct cggagcgtgt cctggtgggg ccccagcggc tgcaggtgct gaatgcctcc     300
cacgaggact ccgggggcta cagctgccgg cagcggctca gcagcgcgt actgtgccac     360 ttcagtgtgc gggtgacaga cgctccatcc tcgggagatg acgaagacgg ggaggacgag     420
gctgaggaca caggtgtgga cacaggggcc ccttactgga cacggcccga gcggatggac     480
aagaagctgc tggccgtgcc ggccgccaac accgtccgct tccgctgccc agccgctggc     540
aaccccactc cctccatctc ctggctgaag aacggcaggg agttccgcgg cgagcaccgc     600
attggaggca tcaagctgcg gcatcagcag tggagcctgg tcatggaaag cgtggtgccc     660
tcggaccgcg gcaactacac ctgcgtcgtg gagaacaagt ttggcagcat ccggcagacg     720
tacacgctgg acgtgctgga gcgctccccg caccggccca tcctgcaggc ggggctgccg     780
gccaaccaga cggcggtgct gggcagcgac gtggagttcc actgcaaggt gtacagtgac     840
gcacagcccc acatccagtg gctcaagcac gtggaggtga acggcagcaa ggtgggcccg     900
gacggcacac cctacgttac cgtgctcaag tcctggatca gtgagagtgt ggaggccgac     960
gtgcgcctcc gcctgccaa tgtgtcggag cgggacgggg gcgagtacct ctgtcgagcc    1020
accaatttca taggcgtggc cgagaaggcc ttttggctga cgttcacgg gccccgagca    1080
```

-continued

```
gccgaggagg agctggtgga ggctgacgag gcgggcagtg tgtatgcagg catcctcagc    1140 tacgggtgg gcttcttcct gttcatcctg gtggtggcgg ctgtgacgct ctgccgcctg    1200
cgcagccccc ccaagaaagg cctgggctcc ccaccgtgc acaagatctc ccgcttcccg    1260
ctcaagcgac aggtgtccct ggagtccaac gcgtccatga gctccaacac accactggtg    1320
cgcatcgcaa ggctgtcctc agggagggc cccacgctgg ccaatgtctc cgagctcgag    1380
ctgcctgccg accccaaatg ggagctgtct cgggcccggc tgaccctggg caagcccctt    1440
ggggagggct gcttcggcca ggtggtcatg gcggaggcca tcggcattga caaggaccgg    1500
gccgccaagc ctgtcaccgt agccgtgaag atgctgaaag acgatgccac tgacaaggac    1560
ctgtcggacc tggtgtctga gatggagatg atgaagatga tcgggaaaca caaaaacatc    1620
atcaaactgc tgggcgcctg cacgcagggc gggcccctgt acgtgctggt ggagtacgcg    1680
gccaagggta acctgcggga gtttctgcgg gcgcggcggc cccgggcct ggactactcc    1740 ttcgacacct gcaagccgcc cgaggagcag ctcaccttca aggacctggt gtcctgtgcc    1800
taccaggtgg cccggggcat ggagtacttg gcctcccaga gtgcatcca cagggacctg    1860 gctgcccgca atgtgctggt gaccgaggac aacgtgatga gatcgcaga cttcgggctg    1920 gcccgggacg tgcacaacct cgactactac aagaagacaa ccaacggccg gctgcccgtg    1980
aagtggatgg cgcctgaggc cttgtttgac cgagtctaca ctcaccgag tgacgtctgg    2040 tcctttgggg tcctgctctg ggagatcttc acgctggggg gctccccgta ccccggcatc    2100
cctgtggagg agctcttcaa gctgctgaag gagggccacc gcatggacaa gcccgccaac    2160
tgcacacacg acctgtacat gatcatgcgg gagtgctggc atgccgcgcc ctcccagagg    2220
cccaccttca gcagctggt ggaggacctg gaccgtgtcc ttaccgtgac gtccaccgac    2280
gagtacctgg acctgtcggc gcctttcgag cagtactccc cgggtggcca ggacaccccc    2340
agctccagct cctcagggga cgactccgtg tttgcccacg acctgctgcc cccggcccca    2400
cccagcagtg ggggctcgcg gacgtga    2427
```

<210> SEQ ID NO 15
<211> LENGTH: 2427
<212> TYPE: DNA
<213> ORGANISM: Artificial Sequence
<220> FEATURE:
<223> OTHER INFORMATION: Description of Artificial Sequence:Mutant N542K
FGFR3-IIIb:
(Mutant 2)

<400> SEQUENCE: 15

```
atgggcgccc ctgcctgcgc cctcgcgctc tgcgtggccg tggccatcgt ggccggcgcc     60
tcctcggagt ccttggggac ggagcagcgc gtcgtgggc gagcggcaga agtcccgggc    120
ccagagcccg gccagcagga gcagttggtc ttcggcagcg gggatgctgt ggagctgagc    180 tgtccccgc ccggggtgg tcccatgggg cccactgtct gggtcaagga tggcacaggg    240
ctggtgccct cggagcgtgt cctggtgggg ccccagcggc tgcaggtgct gaatgcctcc    300
cacgaggact ccgggcccta cagctgccgg cagcggctca cgcagcgcgt actgtgccac    360
ttcagtgtgc gggtgacaga cgctccatcc tcgggagatg acgaagacgg ggaggacgag    420
gctgaggaca caggtgtgga cacagggccc cttactgga cacggccccga gcggatggac    480 aagaagctgc tggccgtgcc ggccgccaac accgtccgct tccgctgccc agccgctggc    540
aaccccactc cctccatctc ctggctgaag aacggcagga gttccgcgg cgagcaccgc    600 attggaggca tcaagctgcg gcatcagcag tggagcctgg tcatggaaag cgtggtgccc    660
```

```
tcggaccgcg gcaactacac ctgcgtcgtg gagaacaagt tggcagcat  ccggcagacg    720 tacacgctgg acgtgctgga gcgctccccg caccggccca tcctgcaggc ggggctgccg    780
gccaaccaga cggcggtgct gggcagcgac gtggagttcc actgcaaggt gtacagtgac    840
gcacagcccc acatccagtg gctcaagcac gtggaggtga acggcagcaa ggtgggcccg    900
gacggcacac cctacgttac cgtgctcaag tcctggatca gtgagagtgt ggaggccgac    960
gtgcgcctcc gcctggccaa tgtgtcggag cgggacgggg gcgagtacct ctgtcgagcc   1020
accaatttca taggcgtggc cgagaaggcc ttttggctga cgttcacgg  gccccgagca   1080 gccgaggagg agctggtgga ggctgacgag gcgggcagtg tgtatgcagg catcctcagc   1140
tacggggtgg gcttcttcct gttcatcctg gtggtggcgg ctgtgacgct ctgccgcctg   1200
cgcagccccc ccaagaaagg cctgggctcc ccaccgtgc  acaagatctc ccgcttcccg   1260
ctcaagcgac aggtgtccct ggagtccaac gcgtccatga gctccaacac caccactggtg  1320 cgcatcgcaa ggctgtcctc aggggagggc cccacgctgg ccaatgtctc cgagctcgag   1380
ctgcctgccg accccaaatg ggagctgtct cgggcccggc tgaccctggg caagcccctt   1440
ggggagggct gcttcggcca ggtggtcatg gcggaggcca tcggcattga caaggaccgg   1500
gccgccaagc ctgtcaccgt agccgtgaaa atgctgaaag acgatgccac tgacaaggac   1560
ctgtcggacc tggtgtctga gatggagatg atgaagatga tcgggaaaca caaaaacatc   1620
atcaagctgc tgggcgcctg cacgcagggc gggcccctgt acgtgctggt ggagtacgcg   1680
gccaagggta acctgcggga gtttctgcgg gcgcggcggc ccccgggcct ggactactcc   1740
ttcgacacct gcaagccgcc cgaggagcag ctcaccttca aggacctggt gtcctgtgcc   1800
taccaggtgg cccggggcat ggagtacttg gcctcccaga gtgcatcca  cagggacctg   1860 gctgcccgca atgtgctggt gaccgaggac aacgtgatga agatcgcaga cttcgggctg   1920
gcccgggacg tgcacaacct cgactactac aagaagacaa ccaacggccg gctgcccgtg   1980
aagtggatgg cgcctgaggc cttgtttgac cgagtctaca ctcaccagag tgacgtctgg   2040
tcctttgggg tcctgctctg ggagatcttc acgctggggg ctccccgta  ccccggcatc   2100 cctgtggagg agctcttcaa gctgctgaag gagggccacc gcatggacaa gcccgccaac   2160
tgcacacacg acctgtacat gatcatgcgg gagtgctgga tgccgcgcc  ctcccagagg   2220 cccaccttca agcagctggt ggaggacctg gaccgtgtcc ttaccgtgac gtccaccgac   2280
gagtacctgg acctgtcggc cccttcgag  cagtactccc cggtggcca  ggacaccccc   2340 agctccagct cctcagggga cgactccgtg tttgcccacg acctgctgcc cccggcccca   2400
cccagcagtg ggggctcgcg gacgtga                                      2427
```

<210> SEQ ID NO 16
<211> LENGTH: 2427
<212> TYPE: DNA
<213> ORGANISM: Artificial Sequence
<220> FEATURE:
<223> OTHER INFORMATION: Description of Artificial Sequence:Mutant G382R
    FGFR3-IIIb:
    (Mutant 1)

<400> SEQUENCE: 16

```
atgggcgccc ctgcctgcgc cctcgcgctc tgcgtggccg tggccatcgt ggccggcgcc     60
tcctcggagt ccttggggac ggagcagcgc gtcgtgggc  gagcggcaga agtcccgggc    120
ccagagcccg ccagcagga  gcagttggtc ttcggcagcg gggatgctgt ggagctgagc    180
```

```
tgtccccgc cggggggtgg tcccatgggg cccactgtct gggtcaagga tggcacaggg    240
ctggtgccct cggagcgtgt cctggtgggg ccccagcggc tgcaggtgct gaatgcctcc   300
cacgaggact ccggggccta cagctgccgg cagcggctca cgcagcgcgt actgtgccac   360
ttcagtgtgc gggtgacaga cgctccatcc tcgggagatg acgaagacgg ggaggacgag   420
gctgaggaca caggtgtgga cacagggggcc ccttactgga cacggcccga gcggatggac  480
aagaagctgc tggccgtgcc ggccgccaac accgtccgct tccgctgccc agccgctggc   540
aaccccactc cctccatctc ctggctgaag aacggcaggg agttccgcgg cgagcaccgc   600
attggaggca tcaagctgcg gcatcagcag tggagcctgg tcatggaaag cgtggtgccc   660
tcggaccgcg gcaactacac ctgcgtcgtg gagaacaagt ttggcagcat ccggcagacg   720
tacacgctgg acgtgctgga gcgctccccg caccggccca tcctgcaggc ggggctgccg   780
gccaaccaga cggcggtgct gggcagcgac gtggagttcc actgcaaggt gtacagtgac   840
gcacagcccc acatccagtg gctcaagcac gtggaggtga acggcagcaa ggtgggcccg   900
gacggcacac cctacgttac cgtgctcaag tcctggatca gtgagagtgt ggaggccgac   960
gtgcgcctcc gcctggccaa tgtgtcggag cgggacgggg gcgagtacct ctgtcgagcc   1020
accaatttca taggcgtggc cgagaaggcc ttttggctga gcgttcacgg gccccgagca   1080
gccgaggagc agctggtgga ggctgacgag gcgggcagtg tgtatgcagg catcctcagc   1140
tacagggtgg gcttcttcct gttcatcctg gtggtggcgg ctgtgacgct ctgccgcctg   1200
cgcagccccc ccaagaaagg cctgggctcc ccaccgtgc acaagatctc ccgcttcccg    1260
ctcaagcgac aggtgtccct ggagtccaac gcgtccatga gctccaacac accactggtg   1320
cgcatcgcaa ggctgtcctc aggggagggc cccacgctgg ccaatgtctc cgagctcgag   1380
ctgcctgccg accccaaatg ggagctgtct cgggcccggc tgaccctggg caagcccctt   1440
ggggagggct gcttcggcca ggtggtcatg gcggaggcca tcggcattga caaggaccgg   1500
gccgccaagc ctgtcaccgt agccgtgaag atgctgaaag acgatgccac tgacaaggac   1560
ctgtcggacc tggtgtctga gatggagatg atgaagatga tcgggaaaca caaaaacatc   1620
atcaacctgc tgggcgcctg cacgcagggc gggcccctgt acgtgctggt ggagtacgcg   1680
gccaagggta acctgcggga gtttctgcgc gcgcggcggc ccccgggcct ggactactcc   1740
ttcgacacct gcaagccgcc cgaggagcag ctcaccttca ggacctggt gtcctgtgcc    1800 taccaggtgg cccggggcat ggagtacttg gcctcccaga agtgcatcca cagggacctg   1860
gctgcccgca atgtgctggt gaccgaggac aacgtgatga agatcgcaga cttcggctg   1920 gcccgggacg tgcacaacct cgactactac aagaagacaa ccaacggccg gctgcccgtg   1980
aagtggatgg cgcctgaggc cttgtttgac cgagtctaca ctcaccagag tgacgtctgg   2040
tcctttgggg tcctgctctg ggagatcttc acgctggggg gctccccgta ccccggcatc   2100
cctgtggagg agctcttcaa gctgctgaag gagggccacc gcatggacaa gcccgccaac   2160
tgcacacacg acctgtacat gatcatgcgg gagtgctggc atgccgcgcc ctcccagagg   2220
cccaccttca gcagctggt ggaggacctg accgtgtcc ttaccgtgac gtccaccgac    2280
gagtacctgg acctgtcggc gcctttcgag cagtactccc cgggtggcca ggacaccccc   2340
agctccagct cctcagggga cgactccgtg tttgcccacg acctgctgcc cccggccccca  2400 cccagcagtg ggggctcgcg gacgtga                                       2427
```

<210> SEQ ID NO 17
<211> LENGTH: 2427

<210> TYPE: DNA
<213> ORGANISM: Artificial Sequence
<220> FEATURE:
<223> OTHER INFORMATION: Description of Artificial Sequence:Mutant G382R
      FGFR3-IIIb:
      (Mutant 2)

<400> SEQUENCE: 17

```
atgggcgccc ctgcctgcgc cctcgcgctc tgcgtggccg tggccatcgt ggccggcgcc     60
tcctcggagt ccttggggac ggagcagcgc gtcgtggggc gagcggcaga agtcccgggc    120
ccagagcccg ccagcaggga gcagttggtc ttcggcagcg ggatgctgt ggagctgagc     180
tgtccccgc cgggggtgg tcccatgggg cccactgtct gggtcaagga tggcacaggg      240
ctggtgccct cggagcgtgt cctggtgggg ccccagcggc tgcaggtgct gaatgcctcc    300
cacgaggact ccggggccta cagctgccgg cagcggctca cgcagcgcgt actgtgccac    360
ttcagtgtgc gggtgacaga cgctccatcc tcgggagatg acgaagacgg ggaggacgag    420
gctgaggaca caggtgtgga cacaggggcc ccttactgga cacggcccga gcggatggac    480
aagaagctgc tggccgtgcc ggccgccaac accgtccgct cccgctgccc agccgctggc    540
aaccccactc cctccatctc ctggctgaag aacggcaggg agttccgcgg cgagcaccgc    600
attggaggca tcaagctgcg gcatcagcag tggagcctgg tcatggaaag cgtggtgccc    660
tcggaccgcg gcaactacac ctgcgtcgtg gagaacaagt ttggcagcat ccggcagacg    720
tacacgctgg acgtgctgga gcgctccccg caccggccca tcctgcaggc ggggctgccg    780
gccaaccaga cggcggtgct gggcagcgac gtggagttcc actgcaaggt gtacagtgac    840
gcacagcccc acatccagtg gctcaagcac gtggaggtga acggcagcaa ggtgggcccg    900
gacggcacac cctacgttac cgtgctcaag tcctggatca gtgagagtgt ggaggccgac    960
gtgcgcctcc gcctggccaa tgtgtcggag cgggacgggg gcgagtacct ctgtcgagcc   1020
accaatttca taggcgtggc cgagaaggcc ttttggctga cgttcacgg gcccgagca    1080
gccgaggagg agctggtgga ggctgacgag gcgggcagtg tgtatgcagg catcctcagc   1140
taccgggtgg gcttcttcct gttcatcctg gtggtggcgg ctgtgacgct ctgccgcctg   1200
cgcagccccc ccaagaaagg cctgggctcc cccaccgtgc acaagatctc ccgcttcccg   1260
ctcaagcgac aggtgtccct ggagtccaac gcgtccatga gctccaacac caccggtgtg   1320
cgcatcgcaa ggctgtcctc aggggagggc cccacgctgg ccaatgtctc cgagctcgag   1380
ctgcctgccg accccaaatg ggagctgtct cgggccggc tgaccctggg caagcccctt   1440
ggggagggct gcttcggcca ggtggtcatg gcggaggcca tcggcattga caaggaccgg   1500
gccgccaagc tgtcaccgt agccgtgaag atgctgaaag acgatgccac tgacaaggac   1560
ctgtcggacc tggtgtctga gatggagatg atgaagatga tcgggaaaca caaaaacatc   1620
atcaacctgc tgggcgcctg cacgcagggc gggccctgt acgtgctggt ggagtacgcg   1680
gccaagggta acctgcggga gtttctgcgg gcgcggcggc ccccgggcct ggactactcc   1740
ttcgacacct gcaagccgcc cgaggagcag ctcaccttca aggacctggt gtcctgtgcc   1800
taccaggtgg cccggggcat ggagtacttg gcctcccaga gtgcatcca gggacctg     1860
gctgcccgca atgtgctggt gaccgaggac aacgtgatga agatcgcaga cttcgggctg   1920
gcccgggacg tgcacaacct cgactactac aagaagacaa ccaacggccg gctgcccgtg   1980
aagtggatgg cgcctgaggc cttgtttgac cgagtctaca ctcaccagag tgacgtctgg   2040
tcctttgggg tcctgctctg ggagatcttc acgctggggg gctccccgta ccccggcatc   2100
```

```
cctgtggagg agctcttcaa gctgctgaag gagggccacc gcatggacaa gcccgccaac    2160
tgcacacacg acctgtacat gatcatgcgg gagtgctggc atgccgcgcc ctcccagagg    2220
cccaccttca agcagctggt ggaggacctg gaccgtgtcc ttaccgtgac gtccaccgac    2280
gagtacctgg acctgtcggc gcctttcgag cagtactccc cgggtggcca ggacaccccc    2340
agctccagct cctcagggga cgactccgtg tttgcccacg acctgctgcc cccggcccca    2400
cccagcagtg ggggctcgcg gacgtga                                        2427
```

<210> SEQ ID NO 18
<211> LENGTH: 2427
<212> TYPE: DNA
<213> ORGANISM: Artificial Sequence
<220> FEATURE:
<223> OTHER INFORMATION: Description of Artificial Sequence:Mutant G377C
      FGFR3-IIIb:

<400> SEQUENCE: 18

```
atgggcgccc ctgcctgcgc cctcgcgctc tgcgtggccg tggccatcgt ggccggcgcc     60
tcctcggagt ccttggggac ggagcagcgc gtcgtgggc gagcggcaga agtcccgggc    120
ccagagcccg gccagcagga gcagttggtc ttcggcagcg gggatgctgt ggagctgagc    180 tgtccccgc ccggggtgg tcccatgggg cccactgtct gggtcaagga tggcacaggg    240
ctggtgccct cggagcgtgt cctggtgggg ccccagcggc tgcaggtgct gaatgcctcc    300
cacgaggact ccggggccta cagctgccgg cagcggctca cgcagcgcgt actgtgccac    360
ttcagtgtgc gggtgacaga cgctccatcc tcgggagatg acgaagacgg ggaggacgag    420
gctgaggaca caggtgtgga cacaggggcc ccttactgga cacggcccga gcggatggac    480
aagaagctgc tggccgtgcc ggccgccaac accgtccgct ccgctgccc agccgctggc    540 aaccccactc cctccatctc ctggctgaag aacggcaggg agttccgcgg cgagcaccgc    600
attggaggca tcaagctgcg gcatcagcag tggagcctgg tcatggaaag cgtggtgccc    660
tcggaccgcg gcaactacac ctgcgtcgtg gagaacaagt ttggcagcat ccggcagacg    720
tacacgctgg acgtgctgga gcgctccccg caccggccca tcctgcaggc ggggctgccg    780
gccaaccaga cggcggtgct gggcagcgac gtggagttcc actgcaaggt gtacagtgac    840
gcacagcccc acatccagtg gctcaagcac gtggaggtga acggcagcaa ggtgggcccg    900
gacggcacac cctacgttac cgtgctcaag tcctggatca gtgagagtgt ggaggccgac    960
gtgcgcctcc gcctggccaa tgtgtcggag cgggacgggg cgagtacct ctgtcgagcc    1020 accaatttca taggcgtggc cgagaaggcc ttttggctga cgttcacgg ccccgagca    1080 gccgaggagg agctggtgga ggctgacgag gcgggcagtg tgtatgcatg catcctcagc    1140 tacgggtgg gcttcttcct gttcatcctg gtggtggcgg ctgtgacgct ctgccgcctg    1200
cgcagccccc ccaagaaagg cctgggctcc ccaccgtgc acaagatctc ccgcttcccg    1260
ctcaagcgac aggtgtccct ggagtccaac gcgtccatga gctccaacac accactggtg    1320
cgcatcgcaa gcctgtcctc aggggagggc cccacgctgg ccaatgtctc cgagctcgag    1380
ctgcctgccg accccaaatg ggagctgtct cgggcccggc tgaccctggg caagcccctt    1440
ggggagggct gcttcggcca ggtggtcatg gcggaggcca tcggcattga caaggaccgg    1500
gccgccaagc ctgtcaccgt agccgtgaag atgctgaaag acgatgccac tgacaaggac    1560
ctgtcggacc tggtgtctga gatggagatg atgaagatga tcgggaaaca caaaaacatc    1620
atcaacctgc tgggcgcctg cacgcagggc gggcccctgt acgtgctggt ggagtacgcg    1680
```

```
gccaagggta acctgcggga gtttctgcgg gcgcggcggc ccccgggcct ggactactcc   1740
ttcgacacct gcaagccgcc cgaggagcag ctcaccttca aggacctggt gtcctgtgcc   1800
taccaggtgg cccggggcat ggagtacttg gcctcccaga agtgcatcca cagggacctg   1860
gctgcccgca atgtgctggt gaccgaggac aacgtgatga agatcgcaga cttcgggctg   1920
gcccgggacg tgcacaacct cgactactac aagaagacaa ccaacggccg gctgcccgtg   1980
aagtggatgg cgcctgaggc cttgtttgac cgagtctaca ctcaccagag tgacgtctgg   2040
tcctttgggg tcctgctctg ggagatcttc acgctggggg gctccccgta ccccggcatc   2100
cctgtggagg agctcttcaa gctgctgaag gagggccacc gcatggacaa gcccgccaac   2160
tgcacacacg acctgtacat gatcatgcgg gagtgctggc atgccgcgcc ctcccagagg   2220
cccaccttca gcagctggt ggaggacctg gaccgtgtcc ttaccgtgac gtccaccgac   2280
gagtacctgg acctgtcggc gcctttcgag cagtactccc cgggtggcca ggacaccccc   2340
agctccagct cctcagggga cgactccgtg tttgcccacg acctgctgcc cccggcccca   2400
cccagcagtg ggggctcgcg gacgtga                                       2427

<210> SEQ ID NO 19
<211> LENGTH: 2427
<212> TYPE: DNA
<213> ORGANISM: Artificial Sequence
<220> FEATURE:
<223> OTHER INFORMATION: Description of Artificial Sequence:Mutant A393E
      FGFR3-IIIb:

<400> SEQUENCE: 19
atgggcgccc ctgcctgcgc cctcgcgctc tgcgtggccg tggccatcgt ggccggcgcc    60
tcctcggagt ccttggggac ggagcagcgc gtcgtgggc gagcggcaga agtcccgggc   120
ccagagcccg gccagcagga gcagttggtc ttcggcagcg gggatgctgt ggagctgagc   180
tgtcccccgc ccgggggtgg tcccatgggg cccactgtct gggtcaagga tggcacaggg   240
ctggtgccct cggagcgtgt cctggtgggg ccccagcggc tgcaggtgct gaatgcctcc   300
cacgaggact ccggggccta cagctgccgg cagcggctca cgcagcgcgt actgtgccac   360
ttcagtgtgc gggtgacaga cgctccatcc tcgggagatg acgaagacgg ggaggacgag   420
gctgaggaca caggtgtgga cacaggggcc ccttactgga cacggcccga gcggatggac   480
aagaagctgc tggccgtgcc ggccgccaac accgtccgct tccgctgccc agccgctggc   540
aaccccactc cctccatctc ctggctgaag aacggcaggg agttccgcgg cgagcaccgc   600
attggaggca tcaagctgcg gcatcagcag tggagcctgg tcatggaaag cgtggtgccc   660
tcggaccgcg gcaactacac ctgcgtcgtg gagaacaagt ttggcagcat ccggcagacg   720
tacacgctgg acgtgctgga cgctccccg caccggccca tcctgcaggc ggggctgccg   780
gccaaccaga cggcggtgct gggcagcgac gtggagttcc actgcaaggt gtacagtgac   840
gcacagcccc acatccagtg gctcaagcac gtggaggtga acggcagcaa ggtgggcccg   900
gacggcacac cctacgttac cgtgctcaag tcctggatca gtgagagtgt ggaggccgac   960
gtgcgcctcc gcctggccaa tgtgtcggag cgggacgggg gcgagtacct ctgtcgagcc  1020
accaatttca taggcgtggc cgagaaggcc ttttggctga gcgttcacgg gccccgagca  1080
gccgaggagg agctggtgga ggctgacgag gcgggcagtg tgtatgcagg catcctcagc  1140
tacgggggtg gcttcttcct gttcatcctg gtggtggagg ctgtgacgct ctgccgcctg  1200
cgcagccccc ccaagaaagg cctgggctcc cccaccgtgc acaagatctc ccgcttcccg  1260
```

-continued

```
ctcaagcgac aggtgtccct ggagtccaac gcgtccatga gctccaacac accactggtg    1320
cgcatcgcaa ggctgtcctc agggagggc cccacgctgg ccaatgtctc cgagctcgag     1380
ctgcctgccg accccaaatg ggagctgtct cgggcccggc tgaccctggg caagccctt    1440 ggggagggct gcttcggcca ggtggtcatg gcggaggcca tcggcattga caaggaccgg    1500
gccgccaagc tgtcaccgt agccgtgaaa atgctgaaag acgatgccac tgacaaggac     1560
ctgtcggacc tggtgtctga gatggagatg atgaagatga tcgggaaaca caaaaacatc    1620
atcaacctgc tgggcgcctg cacgcagggc gggcccctgt acgtgctggt ggagtacgcg    1680
gccaagggta acctgcggga gtttctgcgc gcgcggcggc ccccgggcct ggactactcc    1740
ttcgacacct gcaagccgcc cgaggagcag ctcaccttca aggacctggt gtcctgtgcc    1800
taccaggtgg cccggggcat ggagtacttg gcctcccaga gtgcatcca caggacctg      1860 gctgcccgca atgtgctggt gaccgaggac aacgtgatga agatcgcaga cttcgggctg    1920
gcccgggacg tgcacaacct cgactactac aagaagacaa ccaacggccg gctgccggtg    1980
aagtggatgg cgcctgaggc cttgtttgac cgagtctaca ctcaccagag tgacgtctgg    2040
tcctttgggg tcctgctctg ggagatcttc acgctggggg gctccccgta ccccggcatc    2100
cctgtggagg agctcttcaa gctgctgaag gagggccacc gcatggacaa gcccgccaac    2160
tgcacacacg acctgtacat gatcatgcgg gagtgctggc atgccgcgcc ctcccagagg    2220
cccaccttca gcagctggt ggaggacctg accgtgtcc ttaccgtgac gtccaccgac      2280
gagtacctgg acctgtcggc gcctttcgag cagtactccc cggtggcca ggacaccccc    2340 agctccagct cctcagggga cgactccgtg tttgcccacg acctgctgcc cccggcccca    2400
cccagcagtg ggggctcgcg gacgtga                                         2427
```

<210> SEQ ID NO 20
<211> LENGTH: 2427
<212> TYPE: DNA
<213> ORGANISM: Artificial Sequence
<220> FEATURE:
<223> OTHER INFORMATION: Description of Artificial Sequence:Mutant P250R FGFR3-IIIb:

<400> SEQUENCE: 20

```
atgggcgccc ctgcctgcgc cctcgcgctc tgcgtggccg tggccatcgt ggccggcgcc     60
tcctcggagt ccttggggac ggagcagcgc gtcgtgggc gagcggcaga agtcccgggc    120
ccagagcccg ccagcagga gcagttggtc ttcggcagcg gggatgctgt ggagctgagc    180
tgtcccccgc ccgggggtgg tcccatgggg cccactgtct gggtcaagga tggcacaggg    240
ctggtgccct cggagcgtgt cctggtgggg ccccagcggc tgcaggtgct gaatgcctcc    300
cacgaggact ccgggcccta cagctgccgg cagcggctca cgcagcgcgt actgtgccac    360
ttcagtgtgc gggtgacaga cgctccatcc tcgggagatg acgaagacgg ggaggacgag    420
gctgaggaca caggtgtgga cacaggggcc ccttactgga cacggcccga gcggatggac    480
aagaagctgc tggccgtgcc ggccgccaac accgtccgct tccgctgccc agccgctggc    540
aaccccactc cctccatctc ctggctgaag aacggcaggg agttccgcgg cgagcaccgc    600
attggaggca tcaagctgcg gcatcagcag tggagcctgg tcatggaaag cgtggtgccc    660
tcggaccgcg gcaactacac ctgcgtcgtg gagaacaagt ttggcagcat ccggcagacg    720
tacacgctgg acgtgctgga gcgctcccgg caccggccca tcctgcaggc ggggctgccg    780
gccaaccaga cggcggtgct gggcagcgac gtggagttcc actgcaaggt gtacagtgac    840
```

```
gcacagcccc acatccagtg gctcaagcac gtggaggtga acggcagcaa ggtgggcccg      900
gacggcacac cctacgttac cgtgctcaag tcctggatca gtgagagtgt ggaggccgac      960
gtgcgcctcc gcctggccaa tgtgtcgagc cgggacgggg gcgagtacct ctgtcgagcc     1020
accaatttca taggcgtggc cgagaaggcc ttttggctga gcgttcacgg gccccgagca     1080
gccgaggagg agctggtgga ggctgacgag gcggcagtg tgtatgcagg catcctcagc     1140
tacgggtgg gcttcttcct gttcatcctg gtggtggcgg ctgtgacgct ctgccgcctg     1200
cgcagccccc ccaagaaagg cctgggctcc ccaccgtgc acaagatctc ccgcttcccg     1260
ctcaagcgac aggtgtccct ggagtccaac gcgtccatga gctccaacac accactggtg     1320
cgcatcgcaa ggctgtcctc aggggagggc cccacgctgg ccaatgtctc cgagctcgag     1380
ctgcctgccg accccaaatg ggagctgtct cgggcccggc tgaccctggg caagcccctt     1440
ggggagggct gcttcggcca ggtggtcatg gcggaggcca tcggcattga caaggaccgg     1500
gccgccaagc tgtcaccgt agccgtgaag atgctgaaag acgatgccac tgacaaggac     1560
ctgtcggacc tggtgtctga gatggagatg atgaagatga tcgggaaaca caaaaacatc     1620
atcaacctgc tgggcgcctg cacgcagggc gggcccctgt acgtgctggt ggagtacgcg     1680
gccaagggta acctgcggga gtttctgcgg gcgcggcggc cccgggcct ggactactcc     1740
ttcgacacct gcaagccgcc cgaggagcag ctcaccttca aggacctggt gtcctgtgcc     1800
taccaggtgg cccggggcat ggagtacttg gcctcccaga gtgcatcca cagggacctg     1860
gctgcccgca atgtgctggt gaccgaggac aacgtgatga gatcgcaga cttcgggctg     1920
gcccgggacg tgcacaacct cgactactac aagaagacaa ccaacggccg gctgcccgtg     1980
aagtggatgg cgcctgaggc cttgtttgac cgagtctaca ctcaccagag tgacgtctgg     2040
tcctttgggg tcctgctctg ggagatcttc acgctggggg gctccccgta ccccggcatc     2100
cctgtggagg agctcttcaa gctgctgaag gagggccacc gcatggacaa gcccgccaac     2160
tgcacacacg acctgtacat gatcatgcgg gagtgctggc atgccgcgcc ctcccagagg     2220
cccaccttca gcagctggt ggaggacctg gaccgtgtcc ttaccgtgac gtccaccgac     2280
gagtacctgg acctgtcggc gcctttcgag cagtactccc cgggtggcca ggacaccccc     2340
agctccagct cctcagggga cgactccgtg tttgcccacg acctgctgcc cccggcccca     2400
cccagcagtg ggggctcgcg gacgtga                                         2427
```

<210> SEQ ID NO 21
<211> LENGTH: 18
<212> TYPE: DNA
<213> ORGANISM: human
<220> FEATURE:
<221> NAME/KEY: mutation
<222> LOCATION: (7)
<223> OTHER INFORMATION: Normal N=C; tumour N=T

<400> SEQUENCE: 21
acagagngct ccccgcac                                                    18

<210> SEQ ID NO 22
<211> LENGTH: 18
<212> TYPE: DNA
<213> ORGANISM: human
<220> FEATURE:
<221> NAME/KEY: mutation
<222> LOCATION: (10)
<223> OTHER INFORMATION: Normal N=G, Tumour N=T

<400> SEQUENCE: 22

-continued

```
gacgaggcgn gcagtgtg                                              18

<210> SEQ ID NO 23
<211> LENGTH: 18
<212> TYPE: DNA
<213> ORGANISM: human
<220> FEATURE:
<221> NAME/KEY: mutation
<222> LOCATION: (11)
<223> OTHER INFORMATION: Normal N=C, Tumour N=G

<400> SEQUENCE: 23
acagagcgct ncccgcac                                              18

<210> SEQ ID NO 24
<211> LENGTH: 18
<212> TYPE: DNA
<213> ORGANISM: human
<220> FEATURE:
<221> NAME/KEY: mutation
<222> LOCATION: (10)
<223> OTHER INFORMATION: Normal N=A, Tumour N=G

<400> SEQUENCE: 24
tactacaagn agacaacc                                              18

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: S249C
      primer

<400> SEQUENCE: 25
cagcaccgcc gtctggttgg                                            20

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: S249C
      primer

<400> SEQUENCE: 26
agtggcggtg gtggtgaggg ag                                         22

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: R248C
      primer

<400> SEQUENCE: 27
tgtgcgtcac tgtacaccctt gcag                                      24

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: R248C
      primer
```

```
<400> SEQUENCE: 28
agtggcggtg gtggtgaggg ag                                        22

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: K652E
      primer

<400> SEQUENCE: 29
tggtgaccga ggacaacgtg atg                                       23

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: K652E
      primer

<400> SEQUENCE: 30
agggtgtggg aaggcggtgt tg                                        22

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: G372C
      primer

<400> SEQUENCE: 31
cctcaacgcc catgtctttt cagc                                      24

<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence: G372C
      primer

<400> SEQUENCE: 32
cttgagcggg aagcgggaga tcttg                                     25

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Y375C
      primer

<400> SEQUENCE: 33
cctcaacgcc catgtctttt cagc                                      24

<210> SEQ ID NO 34
<211> LENGTH: 25
<212> TYPE: DNA
<213> ORGANISM: Artificial Sequence
<220> FEATURE:
```

```
-continued

<223> OTHER INFORMATION: Description of Artificial Sequence: Y375C
      primer

<400> SEQUENCE: 34
cttgagcggg aagcgggaga tcttg                                            25
```